United States Patent
Ghosh

(10) Patent No.: US 10,653,749 B2
(45) Date of Patent: May 19, 2020

(54) TARGETING GIV-GEF-GI SIGNALING FOR TREATING DIVERSE DISEASES

(71) Applicants: The Regents of the University of California, Oakland, CA (US); Pradipta Ghosh, San Diego, CA (US)

(72) Inventor: Pradipta Ghosh, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/565,192

(22) PCT Filed: Apr. 15, 2016

(86) PCT No.: PCT/US2016/027897
§ 371 (c)(1),
(2) Date: Oct. 9, 2017

(87) PCT Pub. No.: WO2016/168702
PCT Pub. Date: Oct. 20, 2016

(65) Prior Publication Data
US 2018/0104307 A1    Apr. 19, 2018

Related U.S. Application Data

(60) Provisional application No. 62/148,278, filed on Apr. 16, 2015.

(51) Int. Cl.
| | | |
|---|---|---|
| *A61K 38/17* | (2006.01) | |
| *A61K 38/00* | (2006.01) | |
| *C07K 7/06* | (2006.01) | |
| *C07K 7/08* | (2006.01) | |
| *C07K 14/47* | (2006.01) | |
| *A61P 35/04* | (2006.01) | |
| *C07K 14/005* | (2006.01) | |
| *C07K 19/00* | (2006.01) | |
| *C12N 15/63* | (2006.01) | |

(52) U.S. Cl.
CPC ............ *A61K 38/179* (2013.01); *A61K 38/00* (2013.01); *A61K 38/1741* (2013.01); *A61P 35/04* (2018.01); *C07K 7/06* (2013.01); *C07K 7/08* (2013.01); *C07K 14/005* (2013.01); *C07K 14/4703* (2013.01); *C07K 14/4705* (2013.01); *C07K 19/00* (2013.01); *C12N 15/63* (2013.01); *C07K 2319/02* (2013.01); *C07K 2319/03* (2013.01); *C07K 2319/10* (2013.01); *C07K 2319/21* (2013.01); *C07K 2319/23* (2013.01); *C07K 2319/33* (2013.01); *C07K 2319/43* (2013.01); *C07K 2319/74* (2013.01); *C07K 2319/81* (2013.01)

(58) Field of Classification Search
CPC ............ C12Q 1/6886; C12Q 2600/112; C12Q 2600/158; G01N 2800/56; G01N 2440/14; G01N 33/57484; C12N 15/63
See application file for complete search history.

(56) References Cited

U.S. PATENT DOCUMENTS

| | | | |
|---|---|---|---|
| 2003/0050243 A1* | 3/2003 | Tymianski | A61K 38/08 514/8.3 |
| 2003/0118610 A1 | 6/2003 | Stern et al. | |
| 2010/0061942 A1 | 3/2010 | Ma et al. | |
| 2014/0234872 A1 | 8/2014 | Ghosh | |

OTHER PUBLICATIONS

Garcia-Marcos et al. GIV is a nonreceptor GEF for G alpha i with a unique motif that regulates Akt signaling. Proc Natl Acad Sci U S A. Mar. 3, 2009;106(9):3178-83. (Year: 2009).*
Ma et al. Therapeutic effects of cell-permeant peptides that activate G proteins downstream of growth factors. Proc Natl Acad Sci U S A. May 19, 2015;112(20):E2602-10. (Year: 2015).*
Sakai et al. Transduction of TAT fusion proteins into the human and bovine trabecular meshwork. Invest Ophthalmol Vis Sci. Oct. 2006;47(10):4427-34. (Year: 2006).*
Hiromura et al. Inhibition of Akt Kinase Activity by a Peptide Spanning the bA Strand of the Proto-oncogene TCL1. J. Biol. Chem. 2004, 279:53407-53418. (Year: 2004).*
PCT International Search Report and Written Opinion for PCT Application No. PCT/US2016/027897 dated Aug. 9, 2016 (13 pages).
Ghosh et al., "A Gαi-GIV Molecular Complex Binds Epidermal Growth Factor Receptor and Determines Whether Cells Migrate or Proliferate," Molecular Biology of the Cell, 2010, 21:2338-2354.
Lin et al., "Structural Basis for Activation of Trimeric Gi Proteins by Multiple Growth Factor Receptors via GIV/Girdin," Molecular Biology of the Cell, 2014, 25:3654-3671.

(Continued)

*Primary Examiner* — Marcela M Cordero Garcia
*Assistant Examiner* — Jia-Hai Lee
(74) *Attorney, Agent, or Firm* — Eversheds Sutherland (US) LLP

(57) ABSTRACT

The invention provides cell-permeable Ga-Interacting Vesicle associated protein (GIV)-derived peptides and their use for treatment of diverse diseases. The invention further provides C-terminus of Ga-Interacting Vesicle associated protein (GIV-CT)-based peptides and GIV-CT encoding vectors and methods of use thereof, for successfully manipulating the diverse pathophysiologic processes in which GIV has been implicated. In one aspect, the invention provides cell-permeable peptides PTD-GIV-CT comprising (i) a peptide transduction domain (PTD) and (ii) a C-terminus of Ga-Interacting Vesicle associated protein (GIV-CT) or a mutant thereof. In one embodiment, said peptides are capable of activating Gi downstream of receptor tyrosine kinases (RTKs). The invention also provides pharmaceutical compositions comprising one or more of the peptides of the invention as well as vectors encoding such peptides.

29 Claims, 22 Drawing Sheets
Specification includes a Sequence Listing.

(56) References Cited

OTHER PUBLICATIONS

Lin et al., "Tyrosine Phosphorylation of the Guanine Nucleotide Exchange Factor GIV Promotes Activation of PI3K During Cell Migration," Sci Signal, 2011, 4(192):1-32.
Lopez-Sanchez et al., "Protein Kinase C-theta (PKCθ) Phosphorylates and Inhibits the Guanine Exchange Factor, GIV/Girdin," PNAS, 2013, 110(14):5510-5515.
Ma e al., "Therapeutic Effects of Cell-Permeant Peptides that Activate G Proteins Downstream of Growth Factors," PNAS, 2015, E2602-E2610.
Midde et al., "Multimodular Biosensors Reveal a Novel Platform for Activation of G Proteins by Growth Factor Receptors," PNS, 2015, E937-E946.
Mittal et al., "Src Homology Domain 2-Containing Protein-Tyrosine Phsophatase-1 (SHP-1) Binds and Dephosphorylates Gα-Interacting, Vesicle-Associated Protein (GIV)/Girdin and Attenuates the GIV-Phosphatidylinositol 3-Kinase (PI3K)-Akt Signaling Pathway," Journal of Biological Chemistry, 2011, 286(37):32404-32415.

\* cited by examiner

A

B

TARGETING GIV-GEF-Gi SIGNALING FOR TREATING DIVERSE DISEASES

CROSS REFERENCE TO RELATED APPLICATIONS

This application claims the priority benefit of PCT/US2016/027897 filed on Apr. 15, 2016 which claims priority to a U.S. Provisional Patent Application No. 62/148,278, filed Apr. 16, 2015. The entire contents of which are hereby incorporated by reference.

STATEMENT AS TO FEDERALLY SPONSORED RESEARCH

This invention was made with government support under Grant Nos. CA160911 and DK099226, awarded by National Institute of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 15, 2016, is named 247106.000035_SL.txt and is 26,296 bytes in size.

FIELD OF THE INVENTION

The invention relates to cell-permeable Gα-Interacting Vesicle associated protein (GIV)-derived peptides and their use for treatment of diverse diseases.

BACKGROUND OF THE INVENTION

Receptor Tyrosine Kinases (RTK) and G-protein coupled receptors (GPCR) are the two most widely studied cell signaling hubs in eukaryotes. For several decades these two pathways were believed to operate in a discrete mode by transducing signals through their respective downstream intermediates; upon ligand stimulation RTKs propagate the signals to the interior of the cell via adaptor proteins that are recruited to phosphotyrosines on the receptor tail (1), whereas GPCRs, which are 7-transmembrane (TM) receptors with an intrinsic Guanine nucleotide Exchange Factor (GEF) activity recruit and activate G proteins by triggering the exchange of GDP with GTP nucleotide (2). Gathering evidence over time has unraveled a complex cross-talk between these two pathways at multiple tiers (3, 4). For example, transactivation of RTKs by GPCRs via scaffolding proteins such as β-arrestins (5) is a well-documented and widely-accepted phenomenon. Numerous studies have also provided evidence to support the reverse concept, i.e., transactivation of heterotrimeric G proteins by growth factors (6). However, it was not until recently that this concept gained traction with the discovery and characterization of Gα-Interacting Vesicle associated protein (GIV; a.k.a Girdin), an unusual signal transducer that can bind both RTKs and G proteins.

GIV is a multi-modular (FIG. 1A) signal transducer and a GEF for Gαi (7). Working downstream of a variety of growth factors [EGF (8, 9), IGF (10), VEGF (11), Insulin (7, 12, 13) and PDGFR (14)] GIV modulates, i.e., either enhances, or suppresses a variety of signaling pathways, all via its ability to activate Gαi in the close proximity of a ligand-activated RTK (7). Multiple studies (summarized in FIG. 5 (15)) employing a selective GEF-deficient GIV mutant (F1685A) have demonstrated that the signaling network downstream of RTKs in cells with wild-type GIV is a mirror image of the network in cells expressing a GEF-deficient mutant GIV. It is because cells can alter (increase or decrease) the levels of GIV mRNA/protein or selectively modulate GIV's GEF activity to modulate growth factor signaling pathways across a range of intensities (16), GIV is considered as a cellular "rheostat" for signal transduction (17). Consistent with its ability to integrate signals downstream of multiple receptors, GIV modulates growth factor signaling during diverse biological processes (17), e.g., cell migration, chemotaxis (13), invasion (18), development (19), self-renewal (20), apoptosis (14, 21) and autophagy (12). Increasing evidence also supports the clinical significance of GIV-dependent signaling during diverse disease processes (17); e.g., pathologic angiogenesis (11), liver fibrosis (14), nephrotic syndrome (21), vascular repair (22) and tumor metastasis (23).

The molecular mechanisms that govern how GIV influences a diverse range of pathophysiologic processes and how it may couple activation of G protein to multiple receptors have come to light only recently, at least in the context of a numerous RTKs that signal via GIV. GIV-dependent growth factor signaling appears to rely heavily on the unique multi-modular nature of its C-terminus (CT), within which two unlikely domains coexist—1) a previously defined GEF motif via which GIV binds and activates Gi (7) and 2) a newly defined ~110 a stretch which folds into a SH2-like domain in the presence of phosphotyrosine ligands; the latter is necessary and sufficient to recognize and bind specific sites of autophosphorylation on the receptor tail (9, 24). Thus, GIV serves as a platform that links RTKs to G proteins within RTK-GIV-Gαi ternary complexes only when both its GEF and SH2-like modules are intact. In the absence of either of these modules, ligand-activated RTKs and Gαi are uncoupled, and the recruitment of Gαi to RTKs and subsequent activation of G proteins is impaired.

Most common diseases, e.g., cancer, inflammation, diabetes are driven by multiple cell surface receptors that trigger and sustain a pathologic signaling network. The largest fraction of therapeutic agents that target individual receptors/pathways often eventually fails due to the emergence of compensatory mechanisms. In eukaryotes, receptor tyrosine kinases (RTKs) and trimeric G proteins are two major signaling hubs. Signal transduction via trimeric G proteins has long been believed to be triggered exclusively by G-protein-coupled receptors (GPCRs). This paradigm has recently been challenged by several studies on a multi-modular signal transducer, Gα-Interacting Vesicle associated protein (GIV/Girdin). It was recently demonstrated that GIV's C-terminus (CT) serves as a platform for dynamic association of ligand-activated RTKs with Gαi, and for non-canonical transactivation of G proteins. However, exogenous manipulation of this platform has remained beyond reach.

The discovery of coexisting SH2-like and GEF modules in-tandem within GIV-CT supported the idea that GIV's C-terminus has the necessary modular make-up to serve as a platform for convergent signaling downstream of multiple RTKs via G proteins. However, it was not possible to visualize this platform until recently, when genetically encoded fluorescent biosensors comprised of these two modules within GIV-CT were developed. These biosensors revealed that the evolutionarily conserved C-terminus of GIV represents the smallest, functionally autonomous unit that retains most key properties of full length GIV (25), i.e., 1) they can bind and activate Gαi in cells in a GEF dependent manner; 2) they retain the properties of receptor recruitment and signal transduction characteristic of full length GIV; 3) they serve as a bona fide platform for assembly of RTK-Gαi complexes at the PM and for non-canonical activation of Gαi in response to growth factors; and 4) they are sufficient to trigger cell migration/invasion through basement membrane matrix. Thus, comprised of the essential modules (GEF and SH2-like domains), GIV-CT is sufficient for linking G proteins to RTKs, for triggering G protein activation in the vicinity of ligand-activated RTKs, for modulation of growth factor signaling, and for triggering complex cellular processes like cell invasion.

Despite the emergence of GIV-CT as the long-sought platform for non-canonical transactivation of G proteins by multiple growth factor RTKs, exogenous manipulation of this platform has remained out of reach. There is currently no existing art of disrupting GIV-Gi axis of signaling exogenously; no current knowledge of how such disruption may affect signaling and cell behavior; and/or no current method of modulating multi-receptor driven pathologic signaling.

Insulin resistance (IR) is a metabolic disorder in which adipocytes and muscle cells fail to take up and metabolize glucose in response to the hormone insulin. Although IR is a hallmark of Type II Diabetes Mellitus (T2DM), IR alone in the absence of T2DM significantly increases the risk for stroke, heart failure and atherosclerosis (Carter, 2005; Rundek et al, 2010).

Although multiple etiologic factors contribute to the pathogenesis of IR (Saltiel & Kahn, 2001), they all ultimately converge to suppress critical components of metabolic insulin signaling. Insulin binds its receptors (InsR, IGF1R), which triggers receptor autophosphorylation, and subsequent tyrosine phosphorylation of insulin receptor substrate 1 (IRS1), amongst others. This leads to the recruitment and activation of Src-Homology-2 (SH2) proteins such as p85α(PI3K) and downstream activation of Akt (Taniguchi et al, 2006). Akt triggers the translocation of the 12-transmembrane glucose transporter 4 (GLUT4) to the plasma membrane (PM) by phosphoinhibiting the Rab GTPase activating protein (GAP) AS160 (Miinea et al, 2005). Among the many adaptors that relay signals within the insulin cascade, IRS1 is widely believed to serve as the major node for orchestrating metabolic insulin signaling (Taniguchi et al, 2006).

Besides IRS1, metabolic insulin signaling relies also on the activation of heterotrimeric G proteins, another major hub in eukaryotic signal transduction. InsRs are functionally coupled to the pertussis-toxin sensitive Gαi/o proteins, e.g., insulin can trigger their activation (Ciaraldi & Maisel, 1989; Rothenberg & Kahn, 1988), localization (Gohla et al, 2007) and phosphorylation (Krupinski et al, 1988; O'Brien et al, 1987). Activation of Gi augments insulin sensitivity (Chen et al, 1997; Song et al, 2001), enhances tyrosine phosphorylation of both InsR and IRS1 (Moxham & Malbon, 1996) and triggers efficient translocation of GLUT4 storage vesicles (GSVs) to the PM (Ciaraldi & Maisel, 1989; Kanoh et al, 2000; Song et al, 2001). Although numerous clues consistently point to a critical role of Gi activation in the insulin response, who/what couples and activates Gi downstream of InsR, and how such activation may cross-talk with IRS1-dependent insulin signaling and trigger downstream metabolic events remain unknown. Additionally, little is known about how G protein pathways are altered in IR.

With regard to the pathogenesis of IR, suppression of metabolic insulin signaling via the IRS1/PI3K pathway is an invariable hallmark (Kahn & Flier, 2000; Le Roith & Zick, 2001; Pessin & Saltiel, 2000). Such suppression occurs via common mechanisms that involve cellular accumulation of lipid metabolites (acyl-CoAs, ceramides, and diacyglycerol, etc), which activate, among many other kinases, the critical protein kinase C-Theta (PKCθ) (Griffin et al, 1999; Yu et al, 2002). PKCθ dependent phosphoinhibition of IRS1 at Ser1101 (Li et al, 2004) is considered an important event that triggers lipid-induced IR. PKCθ expression levels are increased in the skeletal muscles of obese diabetics and hold an inverse relationship to insulin sensitivity (Schmitz-Peiffer et al, 1997; Yu et al, 2002), and PKCθ−/− null mice demonstrate a protective effect against IR despite a high fat diet (Kim et al, 2004). These studies and many others have shaped the paradigm that IR is triggered when IRS1 is phosphoinhibited by kinases like PKCθ. However, some recent studies have revealed inconsistencies in this paradigm [summarized in (Hoehn et al, 2008)]. Emerging evidence indicates that IRS1 is insufficient for orchestrating the insulin response (Krook et al, 1996), and that multiple RTKs can trigger IR independent of IRS1 (Hoehn et al, 2008). These studies raise the possibility that major unidentified signaling nodes exist within the insulin signaling cascade, whose inhibition via the fatty-acid/PKCθ pathway triggers IR.

GIV is a Guanine-nucleotide Exchange Factor (GEF) which activates Gαi1/2/3 (Garcia-Marcos et al, 2009), contains a SH2-like domain that directly binds InsR (Lin et al, 2014), is a direct substrate of InsR which phosphorylates GIV at Y1764 (Lin et al, 2011), is a bona-fide enhancer of the PI3K-Akt pathway downstream of InsR and other RTKs (Lin et al, 2011) and is a substrate for PKCθ; the latter phosphorylates and inhibits signaling via the GIV-Gαi axis (Lopez-Sanchez et al, 2013). Furthermore, a recent study has indicated that GIV may serve as a major regulator of the metabolic insulin response in skeletal muscles (Hartung et al, 2013); overexpression of GIV in myoblasts leads to hyperphosphorylation of IRS1 and enhanced glucose uptake, whereas depletion of GIV suppresses both. Despite these insights, the molecular mechanisms that enable GIV to enhance the metabolic insulin-IRS1 response in physiology or mechanisms that derail this pathway in the setting of IR remained unknown.

SUMMARY OF THE INVENTION

The invention provides that a non-genetic exogenous modulation of the Gα-Interacting Vesicle associated protein (GIV/Girdin)-Gi signaling interface is an effective strategy to reset pathologic signaling networks and downstream multiple receptors in a diverse array of pathophysiologic conditions. The invention further provides GIV-CT-based peptides and GIV-CT encoding vectors and methods of use thereof, for successfully manipulating the diverse pathophysiologic processes in which GIV has been implicated.

In one aspect, the invention provides cell-permeable peptides PTD-GIV-CT comprising (i) a peptide transduction domain (PTD) and (ii) a C-terminus of Gα-Interacting Vesicle associated protein (GIV-CT) or a mutant thereof. In one embodiment, said peptides are capable of activating Gi downstream of receptor tyrosine kinases (RTKs). In one embodiment, said peptides are capable of activating Gαi by enhancing nucleotide release via GEF motif and interact with ligand-activated RTKs via SH2-like motif. In one embodiment, said peptides are capable of selectively affecting the activation of Gαi1/2/3, but not Gαo. In one embodiment, said peptides are capable of inhibiting Gi downstream of receptor tyrosine kinases (RTKs). In one embodiment, the peptide PTD comprises TAT PTD sequence YGRK-KRRQRRR (SEQ ID NO: 4). Other non-limiting examples of PTDs which can be used in the peptides of the invention include, e.g., YARKARRQARR (SEQ ID NO: 5), YARAAARQARA (SEQ ID NO: 6), YARAARRAARR (SEQ ID NO: 7), YARAARRAARA (SEQ ID NO: 8), YARRRRRRRRR (SEQ ID NO: 9), and YAAARRRRRRR (SEQ ID NO: 10). In one embodiment, the PTD is connected to the GIV-CT via a linker sequence (e.g., a 7 amino acids long linker). In one specific embodiment, the linker sequence comprises the sequence GGSGHSG (SEQ ID NO: 11). In one embodiment, the peptide further comprises a detection tag sequence (e.g., hemagglutinin (HA) tag). In one embodiment, the peptide further comprises a purification tag sequence (e.g., hexa-histidine (His$_6$) tag).

In one embodiment, the GIV-CT sequence within the peptide comprises a "wild-type" sequence corresponding to amino acids 1660-1870 of human GIV protein. In one embodiment, the GIV-CT consists of the sequence corresponding to amino acids 1660-1870 of human GIV protein. In one specific embodiment, the peptide consists of the sequence (TAT-GIV-CT-WT; SEQ ID NO: 2):

M R G S H H H H H H G M A S M T G G Q Q M G R D L
Y D D D D K D R W G S K L G Y G R K K R R Q R R R
G G S T M S G Y P Y D V P D Y A G S M G G S G H S
G E T L E S R H H K I K T G S P G S E V V T L Q Q
F L E E S N K L T S V Q I K S S S Q E N L L D E V
M K S L S V S S D F L G K D K P V S C G L A R S V
S G K T P G D F Y D R R T T K P E F L R P G P R K
T E D T Y F I S S A G K P T P G T Q G K I K L V K
E S S L S R Q S K D S N P Y A T L P R A S S V I S
T A E G T T R R T S I H D F L T K D S R L P I S V
D S P P A A A D S N T T A A S N V D K V Q E S R N
S K S R S R E Q Q S S.

In another embodiment, the GIV-CT sequence within the peptide comprises a "constitutively active" mutant sequence corresponding to amino acids 1660-1870 of human GIV protein, wherein Ser-1675 is replaced by Asp (S1675D). In one specific embodiment, the GIV-CT consists of the sequence corresponding to amino acids 1660-1870 of human GIV protein, wherein Ser-1675 is replaced by Asp (S1675D).

In a further embodiment, the GIV-CT sequence within the peptide comprises a "constitutively active" mutant sequence corresponding to amino acids 1660-1870 of human GIV protein, wherein Ser-1689 is replaced by Ala (S1689A). In one specific embodiment, the GIV-CT consists of the sequence corresponding to amino acids 1660-1870 of human GIV protein, wherein Ser-1689 is replaced by Ala (S1689A).

In another embodiment, the GIV-CT sequence within the peptide comprises a "dominant-negative" mutant sequence corresponding to amino acids 1660-1870 of human GIV protein, wherein Phe-1685 is replaced by Ala (F1685A). In one embodiment, the GIV-CT consists of the sequence corresponding to amino acids 1660-1870 of human GIV protein, wherein Phe-1685 is replaced by Ala (F1685A). In one specific embodiment, the peptide consists of the sequence (TAT-GIV-CT-F1685A; SEQ ID NO: 3):

M R G S H H H H H H G M A S M T G G Q Q M G R D L
Y D D D D K D R W G S K L G Y G R K K R R Q R R R
G G S T M S G Y P Y D V P D Y A G S M G G S G H S
G E T L E S R H H K I K T G S P G S E V V T L Q Q
A L E E S N K L T S V Q I K S S S Q E N L L D E V
M K S L S V S S D F L G K D K P V S C G L A R S V
S G K T P G D F Y D R R T T K P E F L R P G P R K
T E D T Y F I S S A G K P T P G T Q G K I K L V K
E S S L S R Q S K D S N P Y A T L P R A S S V I S
T A E G T T R R T S I H D F L T K D S R L P I S V
D S P P A A A D S N T T A A S N V D K V Q E S R N
S K S R S R E Q Q S S.

In yet another embodiment, the GIV-CT sequence within the peptide comprises a "dominant-negative" mutant sequence corresponding to amino acids 1660-1870 of human GIV protein, wherein Ser-1689 is replaced by Asp (S1689D). In a specific embodiment, the GIV-CT consists of the sequence corresponding to amino acids 1660-1870 of human GIV protein, wherein Ser-1689 is replaced by Asp (S1689D).

In an additional embodiment, the GIV-CT sequence within the peptide comprises a "dominant-negative" mutant sequence corresponding to amino acids 1660-1870 of human GIV protein, wherein Ser-1675 is replaced by Ala (S1675A). In a specific embodiment, the GIV-CT consists of the sequence corresponding to amino acids 1660-1870 of human GIV protein, wherein Ser-1675 is replaced by Ala (S1675A).

In a further embodiment, the GIV-CT sequence within the peptide comprises a "dominant-negative" mutant sequence corresponding to amino acids 1660-1870 of human GIV protein, wherein Tyr-1764 and Tyr-1798 are replaced by Phe (Y1764F, Y1798F). in a specific embodiment, the GIV-CT consists of the sequence corresponding to amino acids 1660-1870 of human GIV protein, wherein Tyr-1764 and Tyr-1798 are replaced by Phe (Y1764F, Y1798F).

In conjunction with the peptides, the invention also provides pharmaceutical compositions comprising one or more of the peptides of the invention as well as vectors encoding such peptides.

In a separate aspect, the invention provides vectors encoding a C-terminus of Gα-Interacting Vesicle associated protein (GIV-CT) or a mutant thereof (without PTD being necessarily present within the encoded peptide).

In one embodiment, the invention provides a vector encoding GIV-CT, wherein the GIV-CT comprises a "wild-type" sequence corresponding to amino acids 1660-1870 of human GIV protein. In one specific embodiment, the GIV-CT consists of the sequence corresponding to amino acids 1660-1870 of human GIV protein. In one specific embodiment, the GIV-CT consists of the sequence (GIV-CT-WT; SEQ ID NO: 14):

E T L E S R H H K I K T G S P G S E V V T L Q Q F
L E E S N K L T S V Q I K S S S Q E N L L D E V M
K S L S V S S D F L G K D K P V S C G L A R S V S

```
-continued
G K T P G D F Y D R R T T K P E F L R P G P R K T

E D T Y F I S S A G K P T P G T Q G K I K L V K E

S S L S R Q S K D S N P Y A T L P R A S S V I S T

A E G T T R R T S I H D F L T K D S R L P I S V D

S P P A A A D S N T T A A S N V D K V Q E S R N S

K S R S R E Q Q S S.
```

In another embodiment, the invention provides a vector encoding GIV-CT, wherein the GIV-CT comprises a "constitutively active" mutant sequence corresponding to amino acids 1660-1870 of human GIV protein, wherein Ser-1675 is replaced by Asp (S1675D). In one specific embodiment, the GIV-CT consists of the sequence corresponding to amino acids 1660-1870 of human GIV protein, wherein Ser-1675 is replaced by Asp (S1675D).

In a further embodiment, the invention provides a vector encoding GIV-CT, wherein the GIV-CT comprises a "constitutively active" mutant sequence corresponding to amino acids 1660-1870 of human GIV protein, wherein Ser-1689 is replaced by Ala (S1689A). In one specific embodiment, the GIV-CT consists of the sequence corresponding to amino acids 1660-1870 of human GIV protein, wherein Ser-1689 is replaced by Ala (S1689A).

In yet another embodiment, the invention provides a vector encoding GIV-CT, wherein the GIV-CT comprises the "dominant-negative" mutant sequence corresponding to amino acids 1660-1870 of human GIV protein, wherein Phe-1685 is replaced by Ala (F1685A). In one specific embodiment, the GIV-CT consists of the sequence corresponding to amino acids 1660-1870 of human GIV protein, wherein Phe-1685 is replaced by Ala (F1685A).

In another embodiment, the invention provides a vector encoding GIV-CT, wherein the GIV-CT comprises a "dominant-negative" mutant sequence corresponding to amino acids 1660-1870 of human GIV protein, wherein Ser-1689 is replaced by Asp (S1689D). In a specific embodiment, the GIV-CT consists of the sequence corresponding to amino acids 1660-1870 of human GIV protein, wherein Ser-1689 is replaced by Asp (S1689D).

In yet another embodiment, the invention provides a vector encoding GIV-CT, wherein the GIV-CT comprises a "dominant-negative" mutant sequence corresponding to amino acids 1660-1870 of human GIV protein, wherein Ser-1675 is replaced by Ala (S1675A). In one specific embodiment, the GIV-CT consists of the sequence corresponding to amino acids 1660-1870 of human GIV protein, wherein Ser-1675 is replaced by Ala (S1675A).

In a further embodiment, the invention provides a vector encoding GIV-CT, wherein the GIV-CT comprises a "dominant-negative" mutant sequence corresponding to amino acids 1660-1870 of human GIV protein, wherein Tyr-1764 and Tyr-1798 are replaced by Phe (Y1764F, Y1798F). In a specific embodiment, the GIV-CT consists of the sequence corresponding to amino acids 1660-1870 of human GIV protein, wherein Tyr-1764 and Tyr-1798 are replaced by Phe (Y1764F, Y1798F).

In conjunction with the above-described peptides, pharmaceutical compositions and vectors, the invention provides various methods of using such peptides, pharmaceutical compositions and vectors.

Thus, in one aspect, the invention provides a method for modulating a GIV-dependent cellular signaling pathway in a cell, comprising administering to the cell an effective amount of one or more peptides of the invention or a pharmaceutical composition comprising such peptide(s) or a vector encoding such peptide(s) or a GIV-CT-encoding vector described above. In one embodiment, said GIV-dependent cellular signaling pathway is PTK-Gi pathway for G protein activation. In one embodiment, the cell is in a subject.

In another aspect, the invention provides a method for enhancing wound healing in a subject in need thereof, comprising administering to said subject an effective amount of one or more "wild-type" or "constitutively active" mutant peptides described above (e.g, S1675D or S1689A) or a pharmaceutical composition comprising such peptide(s) or a vector encoding such peptide(s) or a GIV-CT-encoding vector encoding "wild-type" or "constitutively active" mutant peptide(s) described above (e.g, S1675D or S1689A). In one embodiment, the peptide(s) or pharmaceutical composition is administered topically to the wound. In one embodiment, the peptide enhances epithelial cell migration into the wound and/or myofibroblast activation and/or collagen production in the wound.

In yet another aspect, the invention provides a method for treating insulin resistance (IR) in a subject in need thereof, comprising administering to the subject an effective amount of one or more "wild-type" or "constitutively active" mutant peptides described above (e.g, S1675D or S1689A) or a pharmaceutical composition comprising such peptide(s) or a vector encoding such peptide(s) or a GIV-CT-encoding vector encoding "wild-type" or "constitutively active" mutant peptide(s) described above (e.g, S1675D or S1689A). In one embodiment, the insulin resistance (IR) is in a skeletal muscle and/or adipose tissue of the subject. In one embodiment, the insulin resistance (IR) is associated with a disease selected from the group consisting of obesity, glucose intolerance, hypertension, dyslipidemia, endothelial dysfunction, atherosclerotic cardiovascular disease (CVD), hyperinsulinemia, type II diabetes, metabolic syndrome, and polycystic ovarian syndrome (PCOS). In a related aspect, the invention provides a method for enhancing metabolic insulin signaling in a subject comprising administering to the subject an effective amount of one or more "wild-type" or "constitutively active" mutant peptides described above (e.g, S1675D or S1689A) or a pharmaceutical composition comprising such peptide(s) or a vector encoding such peptide(s) or a GIV-CT-encoding vector encoding "wild-type" or "constitutively active" mutant peptide(s) described above (e.g, S1675D or S1689A), wherein the subject is suffering from a disease selected from the group consisting of obesity, glucose intolerance, hypertension, dyslipidemia, endothelial dysfunction, atherosclerotic CVD, hyperinsulinemia, type II diabetes, metabolic syndrome, and polycystic ovarian syndrome (PCOS).

In a separate aspect, the invention provides a method for inhibiting tumor metastasis in a subject in need thereof, comprising administering to the subject an effective amount of one or more "dominant-negative" mutant peptides described above (e.g, F1685A, S1689D, S1675A, or Y1764F+Y1798F) or a pharmaceutical composition comprising such peptide(s) or a vector encoding such peptide(s) or a GIV-CT-encoding vector encoding "dominant-negative" mutant peptide(s) described above (e.g, F1685A, S1689D, S1675A, or Y1764F+Y1798F).

In another aspect, the invention provides a method for inhibiting fibrosis in a subject in need thereof, comprising administering to the subject an effective amount of one or more "dominant-negative" mutant peptides described above (e.g, F1685A, S1689D, S1675A, or Y1764F+Y1798F) or a pharmaceutical composition comprising such peptide(s) or a vector encoding such peptide(s) or a GIV-CT-encoding vector encoding "dominant-negative" mutant peptide(s) described above (e.g., F1685A, S1689D, S1675A, or Y1764F+Y1798F). In a related aspect, the invention provides a method for treating a tissue fibrotic disease in a subject in need thereof comprising administering to the subject an effective amount of one or more "dominant-negative" mutant peptides described above (e.g., F1685A, S1689D, S1675A, or Y1764F+Y1798F) or a pharmaceutical composition comprising such peptide(s) or a vector encoding such peptide(s) or a GIV-CT-encoding vector encoding "dominant-negative" mutant peptide(s) described above (e.g., F1685A, S1689D, S1675A, or Y1764F+Y1798F). In one embodiment, the fibrotic disease is selected from the group consisting of liver cirrhosis, liver fibrosis, non-alcoholic fatty liver disease (NAFLD), non-alcoholic steatohepatitis (NASH), alcoholic fatty liver disease, alcoholic steatohepatitis, hepatic steatosis, skeletal muscle fibrosis, skin fibrosis, scleroderma, skin fibrosis secondary to burns, keloids, hypertrophic post-surgical wounds, renal fibrosis, glomerulosclerosis, interstitial-tubular fibrosis, esophageal or gastro-intestinal fibrosis, bone marrow fibrosis, myelodysplastic syndrome, pulmonary fibrosis, peritoneal fibrosis, pancreatic fibrosis, post-radiation fibrosis, cardiac fibrosis and remodeling after myocardial infarction, brain fibrosis secondary to ischemia or infarcts, post-traumatic brain fibrosis, post-traumatic muscle fibrosis, and synovial/joint fibrosis.

In one specific embodiment of any of the above methods of the invention, the peptide(s) or pharmaceutical composition is administered topically, mucosally or by inhalation. In one specific embodiment of any of the above methods of the invention, the peptide(s) or pharmaceutical composition or vector is administered systemically.

In one embodiment of any of the above methods of the invention, the subject is human.

These and other aspects of the present invention will be apparent to those of ordinary skill in the art in the following description, claims and drawings.

BRIEF DESCRIPTION OF THE DRAWINGS

FIG. 1(A). Top: Schematic representation of the domain organization of GIV. From left to right, the functional domains include a microtubule-binding hook domain (black), a coiled-coil homodimerization domain (yellow), a Gα-binding domain (GBD, blue), a phosphoinositide (PI4P) binding motif (purple), a GEF motif (red), and finally, a SH2-like domain (red and blue) that is located within the Akt and Actin-binding domains at the extreme C-terminus. The numbers denote the amino-acids marking the boundaries of each domain. Bottom: Schematic showing how GIV's C-terminal ~210 amino acids link Gαi to ligand-activated RTKs. Homology model of Gαi3 in complex with GIV aa 1678-1689 (left) was generated using the structure of the synthetic peptide KB-752 bound to Gαi1 [Protein Data Bank ID 1Y3A] as a template as done previously (7). Green, Gαi3 subunit; red, TAT-GIV CT's GEF motif. Model of GIV's SH2-like domain bound to a EGFR-derived phosphotyrosine peptide (purple) corresponding to pTyr1148 and its flanking residues is shown (right) (30). The acidic, neutral, and basic potentials are displayed in red, white and blue, respectively. FIG. 1(B). A schematic representation of the modular makeup of cell-permeable TAT-GIV-CT peptides is shown. TAT peptide transduction domain (TAT-PTD) was fused to His and HA tags, and coupled, via a linker (7 residues), to the C-terminus of GIV (1660-1870 residues). A GEF-deficient mutant TAT-GIV-CT was generated by substituting a Phe 1685 into an Ala (F1685A). FIGS. 1C & 1D. Expression and purification of bacterially expressed TAT-GIV CT peptides. The purity and size of TAT-GIV-CT was confirmed by coomassie staining (FIG. 1C) and by immunoblotting (FIG. 1D) with anti-His and anti-GIV-CT antibodies.

FIG. 2A. Pulldown assays were carried out with recombinant TAT-GIV-CT-WT or FA proteins and GST-Gαi3 (GDP loaded) immobilized on glutathione beads. Bound (upper) and input (lower) proteins were analyzed for TAT-GIV-CT proteins by immunoblotting with His mAb. WT, but not FA peptides binds Gαi3. FIG. 2B. Monolayers of HeLa cells were transduced with either vehicle (mock) or ~400 nM TAT-control or TAT-GIV-CT peptides, fixed and co-stained with phalloidin-Texas red (F-actin, red), DAPI (DNA, blue), anti-His antibody (TAT-GIV-CT, green) and analyzed by confocal microscopy. TAT-GIV-CT-FA, but not WT peptides suppressed the formation of actin stress fibers. Red and green channels of the boxed areas on left are magnified and displayed in grayscale on the right. Bar=10 µm. FIGS. 2C & 2D. HeLa cells depleted of endogenous GIV (by ~85%; FIG. S3) were cotransfected with Gαi1-intYFP, Gβ1-CFP and untagged Gγ2 were serum starved, transduced with TAT-GIV-CT WT or FA peptides, or vehicle (mock) and then stimulated with 50 nM EGF for 5 min. Cells were analyzed for changes in FRET by confocal live-cell microscopy. Representative freeze-frame images (FIG. 2C) from live cell movies are shown, which display intensities of acceptor emission due to FRET in each pixel. Loss of FRET at the plasma membrane (PM) indicate dissociation of trimeric Gi1 (see FIG. 8A) due to transactivation of G protein exclusively after ligand stimulation (compare t0 and t5 images in cells transduced with TAT-GIV-CT WT). FIG. 2D. Bar graphs display EGF-triggered changes in FRET intensities observed in (FIG. 2C). Error bars represent mean+/−S.E.M of 5-6 randomly chosen ROIs at the PM per cell, from 4-5 cells per experiment, from 6 independent experiments. Individual YFP and CFP panels and representative region of interest (ROI) used in the analysis is shown in FIG. 8B. FIGS. 2E & 2F. HeLa cells were starved and transduced with TAT peptides and stimulated with EGF as in C prior to lysis. Equal aliquots of lysates were analyzed for activation of EGFR (autophoshorylation) was monitored using anti-phospho (p)Y1068 (FIG. 2E) and Akt signaling using an anti-phospho (p)Ser473 (FIG. 2F) by immunoblotting (IB). TAT-GIV-CT-WT enhances and TAT-GIV-CT-FA suppresses EGFR autophosphorylation and Akt signaling.

FIG. 3A. A schematic summarizing the opposing effect of GIV-WT (enhancement) and GIV-FA (suppression) on scratch-wound induced cell migration in 2D (7). FIG. 3B. Confluent monolayers of HeLa cells were transduced with TAT peptides, scratch-wounded, and assessed for wound closure by serial imaging of the wound for 12 h and 24 h. Graphs display the quantification of % wound area closed by 12 h and 24 h, expressed as migration index (y axis). TAT-GIV-CT-WT, but not FA enhances 2D cell migration. * $p<0.001$. FIG. 3C. Whole cell lysates of HeLa cells treated as in FIG. 3B and harvested at 6 h post-wounding. Equal aliquots of lysates were analyzed for activation of EGFR and Akt signaling pathway by immunoblotting (IB) exactly as in FIGS. 2E & 2F. TAT-GIV-CT-WT, but not FA enhances EGFR autophosphorylation and Akt signaling during 2D cell migration. FIG. 3D. A schematic summarizing the opposing effect of GIV-WT (enhancement) and GIV-FA (suppression) on tumor cell invasion through basement membrane (25). FIG. 3E. MDA MB231 cells transduced with TAT peptides were analyzed for their ability to invade transwell membranes coated with Matrigel in response to EGF. Images display a representative field of the matrigel-coated membrane insert showing crystal violet-stained cells (purple) that have successfully invaded. Bar graphs show quantification of the number of invasive cells/HPF. Error bars represent mean±S.D. of each TAT construct per transwell, from 3 independent experiments. P values for statistical comparison to control are displayed; * $p<0.001$ and  $p<0.01$. FIG. 3F. Equal aliquots of MDA MB231 cells transduced with TAT-peptides in E were analyzed for TAT uptake and Akt signaling immunoblotting (FIG. 3F). FIG. 3G. A schematic summarizing the opposing effect of GIV-WT (enhancement) and GIV-FA (suppression) on HSC activation and collagen production (14). FIG. 3H-J. Serum-starved Lx2 cells were treated with TGFβ1 for 24 h while simultaneously being serially transduced with TAT peptides every 8 h. Cells were analyzed for Collagen al (FIG. 3H) and α-SMA (I) qPCR. Results are displayed as fold change in response to TGFβ1 (y axis). Values are normalized to the fold change observed in control cells. Error bars represent mean±S.D; n=3;  $p<0.01$ for collagen and * $p<0.05$ for αSMA. (FIG. 3J) Equal aliquots of lysates of TAT-transduced Lx2 cells were analyzed for uptake of TAT-GIV-CT proteins and phosphorylation of SMAD2/3 by immunoblotting (IB).

FIG. 4A. A schematic summarizing GIV's role in modulating functions of a variety of cell types that trigger key aspects of tissue response after wounding (7, 8, 11, 13-15, 17, 18, 22, 35), all of which coordinately facilitate wound healing. The supporting literature is cited in each context. FIG. 4B. Schematic showing the randomized blinded study protocol for dermal wound healing in mice. Two punch biopsy wounds per mice were made on day 0 were treated with 15 µg (~500 pmol) TAT proteins every 24 h for 8 days. N=10 wounds per treatment arm. FIG. 4C. Representative photographs of wounds obtained every 48 h from each treatment arm are displayed. FIG. 4D. Graphs show quantification of % wound area (y axis) at various times. Compared to TAT-control, TAT-GIV-CT-WT accelerates and FA retards wound healing. Error bars represent mean±S.D. **** $p<0.0001$.

FIG. 9(A) Left: Lysates of L6 myotubes treated either with control (Scr) or with GIV siRNA were analyzed for GIV and tubulin by immunoblotting (IB). Right: Bar graph displays efficiency of GIV depletion. FIG. 9(B) Control (Scr siRNA) and GIV-depleted (GIV siRNA) L6 myotubes were analyzed for glucose uptake after insulin stimulation by fluorometric assay. Bar graphs display fold change in uptake compared to starved controls (Y axis). Error bars represent mean±S.D. n=3. FIG. 9(C) Control L6 myotubes or those stably expressing siRNA-resistant GIV-WT, GIV-FA or GIV-SD were treated (+) or not (−) with either control (Scr) or GIV siRNA prior to lysis. Equal aliquots of whole cell lysates were analyzed for GIV-FLAG expression by immunoblotting (IB) for GIV and tubulin. FIG. 9(D) L6 myotubes stably expressing siRNA-resistant GIV-WT, GIV-FA or GIV-SD were depleted of endogenous GIV by siRNA as in panel C and analyzed for glucose uptake after insulin stimulation by fluorometric assay. Bar graphs display fold change in uptake compared to starved controls (Y axis). Error bars represent mean±S.D. n=3. FIG. 9E &9F. L6 myotubes stably expressing Gαi3-WT and Gαi3-WF were analyzed for Gαi3 and tubulin by immunoblotting (IB; FIG. 9E) and for glucose uptake (FIG. 9F). Bar graphs display fold change in uptake compared to starved controls (Y axis). Error bars represent mean±S.D. n=3.

FIG. 10(A) Lysates of serum starved L6 myotubes stimulated with insulin were analyzed for various components of metabolic insulin signaling by immunoblotting (IB). FIG. 10(B) Lysates of serum starved or insulin stimulated L6 myotubes stably expressing GIV-WT or GIV-SD were analyzed for activation of GIV, IRS1, InsRβ and Akt by immunoblotting (IB). FIG. 10(C) Immunoprecipitation was carried out on lysates (right panel) of insulin-treated L6 myotubes with anti-pInsRβ or control IgG. Bound immune complexes (left panel) were analyzed for activated GIV, IRS1 and InsRβ by immunoblotting (IB). (D-E) Serum starved Cos7 cells were stimulated with insulin, fixed and subsequently stained for active GIV (pY1764-GIV (FIG. 10D), active IRS1 (pY632-IRS1; FIG. 10E), active InsRβ (pY1150/51-InsRβ; and DAPI/DNA. Scale bar=10 Bar=10 FIG. 10(F) Serum starved control (Scr shRNA) or GIV-depleted (GIV shRNA) Cos7 cells were stimulated with insulin, fixed and stained for active InsRβ (pY1150/51-InsRβ; green) and Gαi3 (red) and analyzed by dSTORM microscopy. High degree of colocalization was observed, as determined by the presence of yellow pixels in the merged images. FIG. 10(G) Lysates of starved and insulin stimulated L6 myotubes stably expressing GIV-WT or GIV-SD were analyzed for activation of IRS1, AS160, Akt and tubulin by immunoblotting (IB). FIG. 10(H) Schematic illustrating how the presence or absence of a functional GIV-GEF, via which GIV links and activates Gi in the vicinity of InsRβ, dictates the intensity of metabolic insulin signaling, beginning with the activation and autophosphorylation of InsRβ.

FIG. 11(A). A schematic for the biosensor phocus-2nes is shown. Energy transfer from CFP to YFP occurs only when Y941 is phosphorylated and the N—SH2 domain of p85α binds the phosphotyrosine ligand. FIGS. 11B & 11C. Serum starved Cos7 cells coexpressing phocus-2nes with either GIV-WT-FLAG or GIV-SD-FLAG were stimulated with insulin, fixed, stained for FLAG and analyzed for FRET using confocal microscopy. Images panels display (from left to right, FIG. 11B) CFP, YFP, FLAG (GIV) and intensities of acceptor emission due to FRET in each pixel 5 min after insulin stimulation. Image panels of serum starved (0 min) cells are shown in FIG. 15A. Bar graph (FIG. 11C) displays the FRET efficiency observed in GIV-WT versus GIV-SD cells at 0 and 5 min. The analysis represents 5 regions of interest (ROIs) from 4-6 cells/experiment (3 independent experiments). Error bars=Mean±SD. FIG. 11(D). Serum starved control (sh Control) or GIV-depleted (sh GIV) Cos7 cells expressing IRS1-HA were stimulated with insulin, fixed, stained for HA (green) and DAPI/DNA (blue) and analyzed by confocal microscopy. Insets show the magnification of the boxed regions. Scale bar=10 μm. Arrowheads denote PM. FIG. 11(E) Serum starved control (sh Control) or GIV-depleted (sh GIV) Cos7 cells were stimulated with insulin, fixed, stained for endogenous pY632-IRS1 (red) and DAPI/DNA (blue) and analyzed by confocal microscopy. Insets show the magnification of the boxed regions. Scale bar=10 FIG. 11(F). Immunoprecipitation was carried out on lysates of starved or insulin stimulated control (sh Control) or GIV-depleted (sh GIV) Cos7 cells expressing InsRβ-FLAG. Bound immune complexes were analyzed for IRS1, InsRβ (FLAG) and IgG by immunoblotting (IB). IRS1 coimmunoprecipitated with InsRβ in control cells, but not in GIV-depleted cells. FIG. 11(G). GIV-depleted HeLa cells stably expressing GIV-WT or GIV-SD were transiently transfected with InsR-HA, starved and stimulated with 100 nM Insulin for 5 min prior to lysis. InsR and receptor-bound complexes were immunoprecipitated by incubating equal aliquots of lysates with anti-HA mAb or controlgG, followed by protein G beads. Immune complexes were analyzed for GIV, InsR (HA), ligand-activated InsR (pY1150, 1151 InsR), pY632 IRS1 and Gαi3 by immunoblotting (IB). Equal loading of lysates was confirmed by analyzing GIV, Gαi3 and tubulin by immunoblotting. Maximal autophosphorylation of InsR and recruitment of GIV, IRS1 and Gαi3 to the receptor was observed in cells expressing GIV-WT exclusively after insulin stimulation, but not in cells expressing GIV-SD.

FIG. 12(A). Immunoprecipitation was carried out on lysates (right) of starved or insulin-treated Cos7 cells expressing IRS1-HA. Lysates and bound immune complexes (left) were analyzed for activated GIV (pY1764-GIV), total (t)GIV, IRS1 (HA), p85a, SHP2 and Grb2 by immunoblotting (IB). FIG. 12(B) Pulldown assays were carried out with recombinant His-GIV-CT and GST-tagged domains of IRS1 (see Supplemental Information) immobilized on glutathione beads. Bound (upper) and input (lower) proteins were analyzed for His-GIV-CT by immunoblotting with His mAb. FIG. 12(C) Schematic summarizing how the presence or absence of GIV affects localization and phosphoactivation of IRS1.

FIG. 13(A). Lysates of L6 myotubes treated (+) or not (−) with PA alone, or a combination of PA and Pio were analyzed for phosphorylation of GIV at S1689 and Y1764 and total (t)GIV by immunoblotting (IB). FIG. 13(B). Lysates of L6 myotubes treated (+) or not (−) with PA alone, or a combination of PA and a pseudosubstrate PKCθ inhibitor were analyzed for phosphorylation of GIV at S1689 (pS1689 GIV), total (t)GIV and tubulin by immunoblotting (IB). FIG. 13(C). L6 myotubes stably expressing siRNA-resistant GIV-WT or GIV-SA were depleted of endogenous GIV by siRNA, treated with PA (+) or vehicle control (−) and subsequently analyzed for insulin stimulated glucose uptake by fluorometric assay. Bar graph displays fold change in glucose uptake compared to starved controls (Y axis). Error bars represent mean±S.D. n=3. FIG. 13(D). L6 myotubes stably expressing siRNA-resistant GIV-WT or GIV-SD were depleted of endogenous GIV by siRNA, treated (+) or not (−) with Pio, and subsequently stimulated with insulin prior to lysis. Lysates were analyzed for activation of GIV (pY1764 GIV) and Akt (pS473Akt) by immunoblotting (IB). FIG. 13(E). L6 myotubes stably expressing siRNA-resistant GIV-WT or GIV-SD were depleted of endogenous GIV by siRNA, treated (+) or not (−) with Pio, and subsequently analyzed for insulin stimulated glucose uptake by fluorometric assay. Bar graph displays fold change compared to starved controls (Y axis). Error bars represent mean±S.D. n=3. FIG. 13(F). Equal aliquots of lysates of vastus lateralis biopsies from obese type II diabetic subjects, obtained before (basal) or after 6 months of Pio therapy were analyzed for phosphoinhibition of GIV-GEF (pS1689 GIV) and phospho (p)Akt by immunoblotting (IB). Representative samples are shown. n=8. FIGS. 13G & 13H. Equal aliquots of lysates of vastus lateralis biopsies from patients with PCOS, obtained before (basal) and after Pio therapy were analyzed for pS1689GIV by immunoblotting. FIG. 13(G). A representative immunoblot of biopsies obtained from "responder" and "non-responder" patients are shown (n=8). Bar graph displays fold change in GIV phosphorylation at S1689 observed in normal and PCOS patients before and after Pio treatment (Y axis). FIG. 13(H). B—basal; Pio—Pioglitazone treatment. Error bars represent mean±S.D. FIG. 13(I). Schematic illustrates our proposed model for GIV's role as a pivot for the antagonistic actions of fatty acids like Palmitate that trigger IR (red arrow) and insulin sensitizers like Pioglitazone that reverse IR (green). Phosphorylation at S1689 is essential for PA to induce IR, whereas dephosphorylation is required for Pio to enhance tyrosine phosphorylation of IRS1 and GIV, restore Akt signaling and reinstate insulin sensitivity.

FIG. 14(A). Design of the cell-permeant TAT-GIV-CT peptides is shown. TAT-PTD was fused to His and HA tags, and coupled via a linker (GGSGHSG, SEQ ID NO: 11) to the C-terminus of GIV (aa 1660-1870). FIG. 14(B). Purified recombinant TAT-GIV-CT peptides were analyzed by coomassie blue staining and by immunoblotting (IB) with anti-GIV-CT and anti-His antibodies. FIG. 14(C). L6 myotubes were treated with TAT-GIV-CT-WT or FA peptides and cultured overnight in low serum conditions (0.2% FBS) prior to fixation. Fixed cells were stained for His (green), phalloidin (F-actin, red) and DAPI/DNA (blue) and analyzed by confocal microscopy. FIG. 14(D). L6 myotubes were treated with TAT-GIV-CT-WT or FA peptides, starved and stimulated with insulin prior to lysis. Equal aliquots of lysates were analyzed for transduction of TAT-peptides with anti-His antibody, activation of IRS1 (pY632-IRS1) and Akt (pS473) by immunoblotting (IB). FIG. 14(E). L6 myotubes were treated with TAT-GIV-CT-WT or FA peptides, starved and subsequently analyzed for insulin stimulated glucose uptake by fluorometric assay. Bar graph displays fold change in uptake compared to starved controls (Y axis). Error bars represent mean±S.D. FIG. 14(F). L6 myotubes were treated (+) or not (−) with PA to induce IR, then transduced with TAT-GIV-CT-WT or FA peptides, and subsequently analyzed for insulin stimulated glucose uptake by fluorometric assay. Bar graph displays fold change in uptake compared to starved controls (Y axis). Error bars represent mean±S.D. FIG. 14(G). L6 myotubes were treated (+) or not (−) with PA to induce IR, then either treated with Pio or transduced with TAT-GIV-CT-WT peptides (as indicated), and subsequently analyzed for insulin stimulated glucose uptake by fluorometric assay. Bar graph displays fold change in uptake compared to starved controls (Y axis). Error bars represent mean±S.D.

FIG. 16(A). Confirmation of the efficacy of GIV depletion in HeLa cells. Lysates of HeLa cells treated either with control (Scr) or with GIV siRNA were analyzed for GIV and tubulin by immunoblotting (IB). FIG. 16(B). Bar graph displays efficiency of GIV depletion. FIG. 16(C). Depletion of GIV reduces glucose uptake in response to insulin in HeLa cells. Control (si Scr) or GIV-depleted (si GIV) HeLa cells were analyzed for glucose uptake after insulin stimulation (100 nM, 1 h) by fluorometric assay. Bar graph displays fold change in glucose uptake compared to starved controls (Y axis). Error bars represent mean±S.D. n=3. Statistical significance was assessed with two-tailed Student's t-test. FIG. 16(D). Glucose uptake in response to insulin was efficient in HeLa cells expressing GIV-WT, but not in cells expressing GIV-FA or GIV-SD mutants. HeLa cell lines stably expressing siRNA-resistant GIV-WT-FLAG, GIV-FA-FLAG or GIV-SD-FLAG were depleted of endogenous GIV and analyzed for glucose uptake after insulin stimulation (100 nM, 1 h) by fluorometric assay. Bar graph displays fold change in glucose uptake compared to starved controls (Y axis). Error bars represent mean±S.D. n=3. Statistical significance was assessed with two-tailed Student's t-test.

FIG. 17(A). HeLa cells expressing GIV-FA and GIV-SD showed decreased activation of IRS1 and Akt in response to insulin compared to control HeLa cells expressing GIV-WT. Control HeLa cells or those stably expressing GIV-WT-FLAG, GIV-FA-FLAG or GIV-SD-FLAG were starved in the presence of 0.2% FBS overnight and stimulated with insulin prior to lysis. Equal aliquots of whole cell lysates were analyzed for activation of IRS1 (pY632) and Akt (pS473) by immunoblotting (IB). FIG. 17(B). HeLa-GIV-WT, but not HeLa-GIV-SD cells enhance the phosphoinhibition of the RabGAP AS160 by Akt after insulin stimulation. HeLa cells stably expressing GIV-WT-FLAG or GIV-SD-FLAG were starved in the presence of 0.2% FBS overnight and stimulated with insulin prior to lysis. Equal aliquots of whole cell lysates were analyzed for phosphorylation (pT642) of AS160 by immunoblotting (IB).

FIG. 18(A). Serum starved Cos7 cells coexpressing phocus-2nes with either GIV-WT-FLAG or GIV-SD-FLAG were stimulated with insulin, fixed, stained for FLAG (far red) and analyzed for FRET using confocal microscopy. Images panels display (from left to right) CFP, YFP, FLAG (GIV) and intensities of acceptor emission due to FRET in each pixel in serum starved cells. Image panels of insulin stimulated (5min) cells are shown in FIG. 11B. FIG. 18(B). Depletion of GIV does not affect the levels of InsRβ or IRS1 proteins. Equal aliquots of whole cell lysates of control (sh Control) or GIV-depleted (sh GIV) Cos7 cells were analyzed for GIV, InsRβ, IRS1, Gαi3 and tubulin by immunoblotting (IB). FIG. 18(C). GIV-depleted Cos7 cells show decreased activation of IRS1 in response to insulin compared to control Cos7 cells. Serum starved control (sh Control) and GIV-depleted (sh GIV) Cos7 cells were stimulated with insulin prior to lysis. Equal aliquots of whole cell lysates were analyzed for GIV, pY632-IRS1 and tubulin by immunoblotting (IB). FIG. 18(D). Insulin triggers the recruitment of IRS1 to the PM in Cos7 cells expressing GIV-WT, but not in those expressing the GEF-deficient GIV-SD mutant. Serum starved Cos7 cells coexpressing IRS1-HA and either GIV-WT-FLAG or GIV-SD-FLAG were stimulated with insulin (5min, 100 nM) prior to fixation. Fixed cells were then stained for HA (IRS1, red), FLAG (GIV, green) and DAPI/DNA (blue) and analyzed by confocal microscopy. Scale bar=10 μm.

FIG. 19(A). The N-terminus of IRS1 (IRS1-N) binds equally to GIV-CT-WT and GIV-CT-SD in vitro. Pulldown assays were carried out with recombinant His-tagged GIV-CT-WT or GIV-CT-SD proteins and GST-tagged IRS1-N immobilized on glutathione beads. Bound proteins were analyzed by immunoblotting (IB) for His (His-GIV-CT). Equal loading of GST proteins was confirmed by Ponceau S staining. Equal amounts of His-GIV-CT proteins were confirmed by analyzing the inputs by immunoblotting (IB). FIG. 19(B). IRS1 constitutively interacts with full length GIV-WT and GIV-SD proteins in cells.

Serum starved Cos7 cells coexpressing IRS1-HA and either GIV-WT-FLAG or GIV-SD-FLAG were stimulated with insulin prior to lysis. Immunoprecipitation was carried out using equal aliquots of lysates using anti-HA mAb and protein G beads. Bound immune complexes were analyzed for HA (IRS1), FLAG (GIV) and IgG by immunoblotting (IB).

Figure 5:
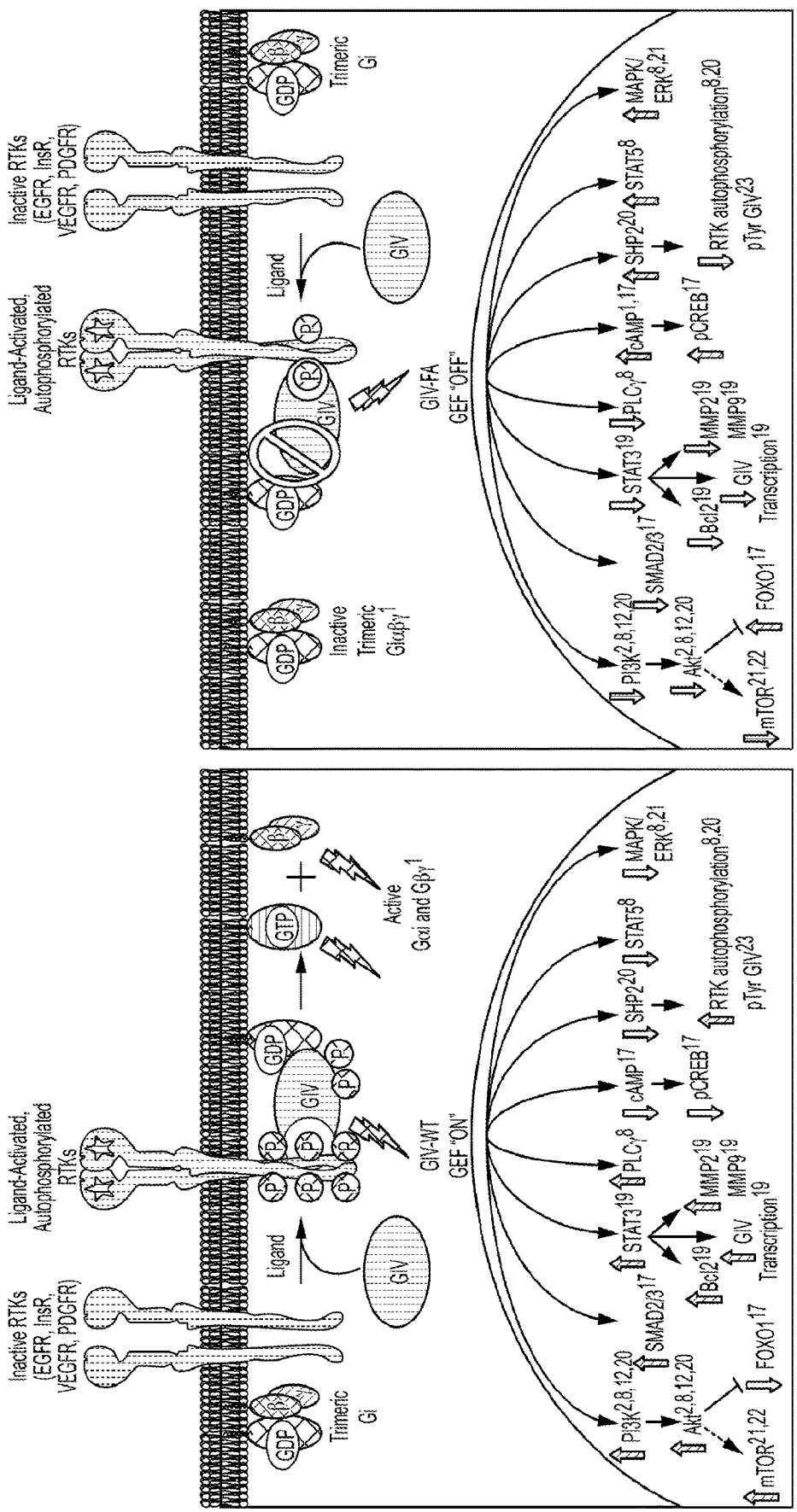
FIG. 5. Presence (GEF "ON") or absence (GEF "OFF") of a functional GEF motif in GIV is a key determinant of several signaling pathways downstream of ligand-activated RTKs. A schematic summary of the mirror-image growth factor signaling profile observed in cells expressing wild-type (GIV-WT) or GEFdeficient (GIV-FA). A variety of signaling pathways (1, 2, 8, 12, 17, 19-23) are either enhanced (green upward arrow) or suppressed (red downward arrow).
Figures 20A, 20B, 20C, 20D:
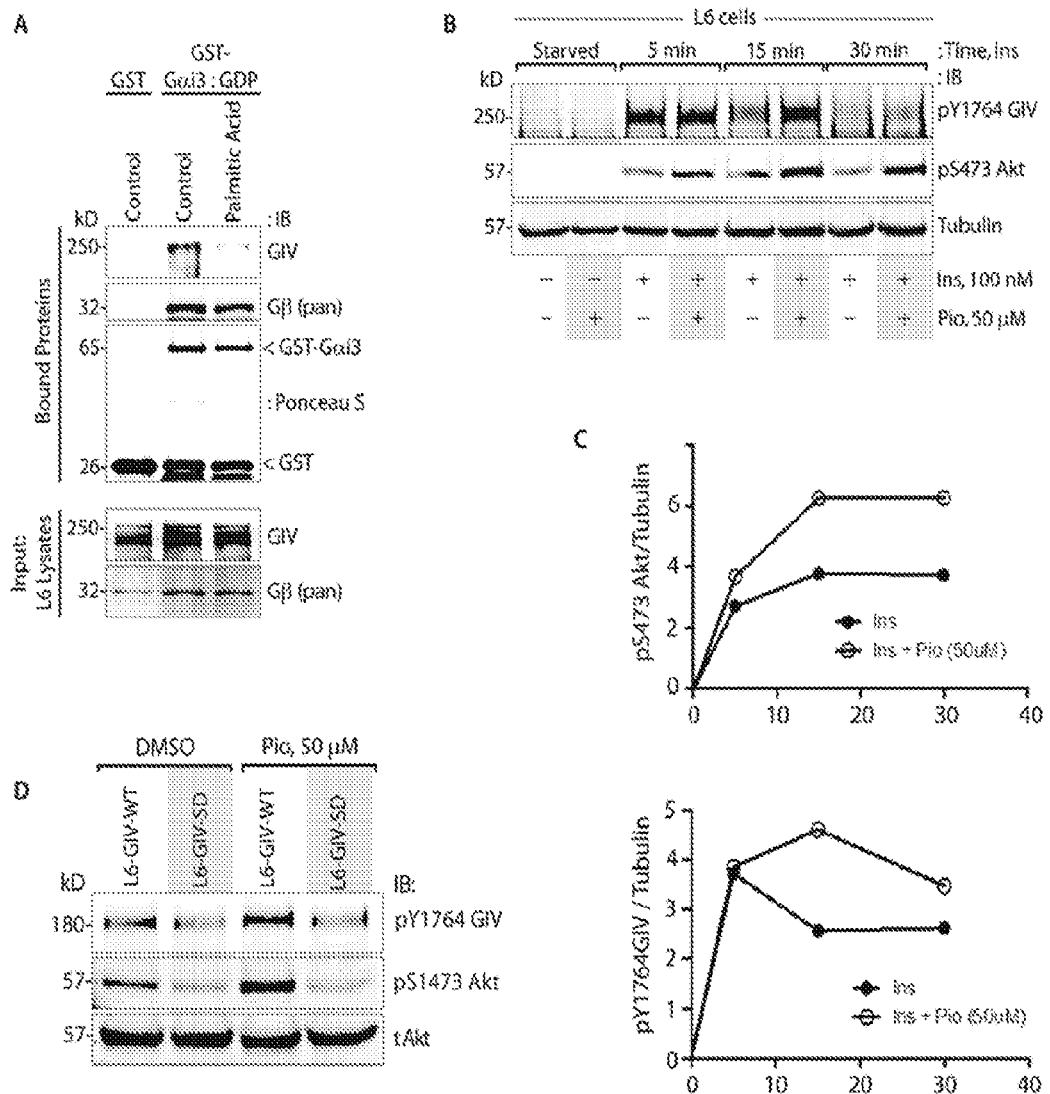

FIGS. 20A-20D. Effect of fatty acids (Sodium Palmitate; PA) and insulin sensitizer (Pioglitazone) on GIV. FIG. 20(A). PA-induced IR in L6 myoblasts is associated with a loss of GIV's ability to bind Gαi3. Pulldown assays were carried out using equal aliquots of GST or GST-Gαi3 [preloaded with GDP] immobilized on glutathione beads and lysates of L6 myoblasts that were treated with either PA (0.5 mM, 16 h) or vehicle (control). The duration and concentration of PA used to treat L6 cells was confirmed as sufficient to induce IR (see FIG. 5A-C). Equal aliquots of input lysates and bound proteins were analyzed by immunoblotting (IB) for GIV and Gβγ. Equal loading of GST proteins was confirmed by Ponceau S staining. Treatment with PA was associated with a loss of binding of GIV to Gαi3. By contrast, binding of Gβγ to Gαi3 (used as negative control) remained unchanged regardless of PA-treatment. FIGS. 20B & 20C. Tyrosine phosphorylation of GIV and Akt activation after insulin stimulation were enhanced by the insulin sensitizer Pioglitazone (Pio). FIG. 20(B). Equal aliquots of serum starved L6 cells treated with Pio (50 μM, 18 h) and subsequently stimulated with insulin (100 nM) were analyzed for activation of GIV (as determined by phosphorylation of GIV at Y1764; pY1764) and Akt (as determined by phosphorylation of Akt at S473; pS473) by immunoblotting (IB). FIG. 20(C). Graphs display the quantification of activated Akt (upper) and GIV (lower) normalized to tubulin (Y axis) at various time points after insulin stimulation (X axis). Immunoblots and graphs displayed are representative of 3 independent experiments. FIG. 20(D). Insulin sensitizer Pioglitazone (Pio) enhances tyrosine phosphorylation of GIV and Akt signaling at steady-state in L6 myoblasts expressing GIV-WT, but not in those expressing the GIV-SD mutant. GIV-depleted L6 cells stably expressing GIV-WT or GIV-SD were treated with Pio (50 μM, 18 h) or vehicle (DMSO) control prior to lysis. Equal aliquots of whole cell lysates were analyzed for activation of GIV (as determined by phosphorylation of GIV at Y1764; pY1764) and Akt (as determined by phosphorylation of Akt at S473; pS473) by immunoblotting (IB).

Figure 21:
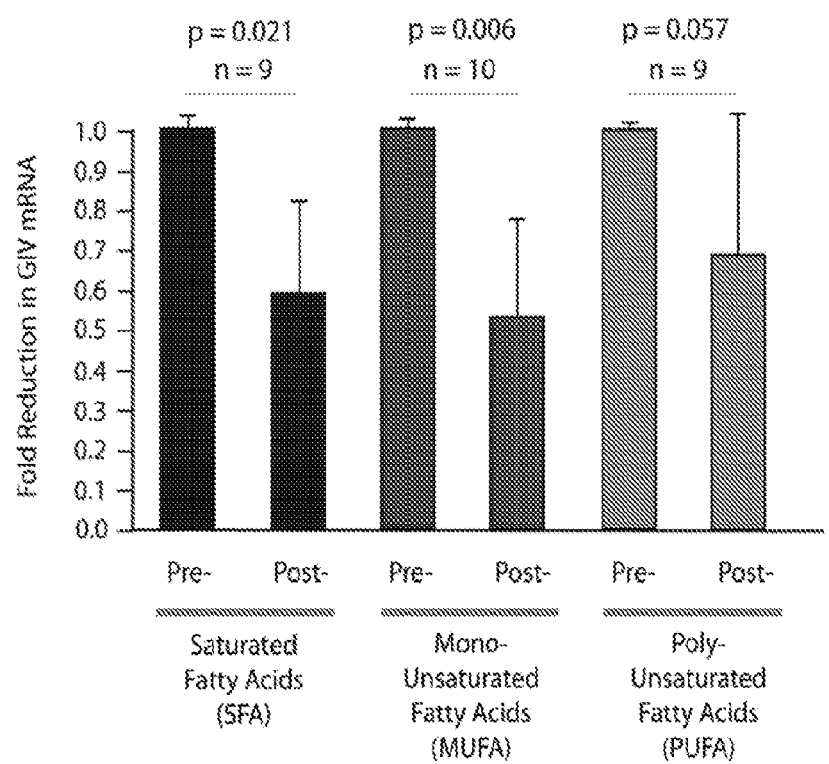

FIG. 21. Effect of acute lipotoxicity on the level of GIV mRNA in skeletal muscles of insulin resistant patients. Bar graph displays the fold decrease in the levels of GIV mRNA reported in gene expression analysis carried out on vastus lateralis samples from insulin resistant men before (pre-) and after (post-) meal induced lipotoxicity (Jans et al., 2012). Briefly, GEO profiles of CCDC88A gene expression in skeletal muscles from insulin resistant men 4 hrs after consumption of meals high in saturated FA (SFA), monounsaturated FA (MUFA), or polyunsaturated FA (PUFA) were analyzed. While GIV mRNA levels are significantly suppressed after SFA and MUFA-rich diets, no significant suppression was noted after ingestion of PUFA-enriched meals. The study also reported that PUFAs, but not SFA and MUFA reduced triacylglycerol-derived skeletal muscle fatty acid uptake, which was accompanied by higher postprandial insulin sensitivity. Our finding that GIV levels are suppressed by SFA and MUFA, but not PUFA are consistent with the fact that SFA and certain MUFAs have been implicated in causing insulin resistance, whereas PUFAs largely do not appear to have adverse effects on insulin action (Lovejoy, 2002).

DETAILED DESCRIPTION OF THE INVENTION

Definitions

Unless defined otherwise, all technical and scientific terms used herein have the same meaning as commonly understood by one of ordinary skill in the art to which the invention pertains. Other specifically defined terms are to be construed in a manner consistent with the definition provided herein. Although any methods and materials similar or equivalent to those described herein can be used in the practice for testing of the present invention, the preferred materials and methods are described herein. In describing and claiming the present invention, the following terminology will be used.

As used in this specification and the appended claims, the singular forms "a", "an" and "the" include plural referents unless the content clearly dictates otherwise. Thus, for example, reference to "a construct" includes a combination of two or more nucleic acid constructs, and the like.

As used herein, the term "subject" refers to humans, mammals and/or veterinary animals (e.g., cats, dogs, cows, horses, sheep, pigs, etc.), and experimental animal models. In certain embodiments, the subject refers to a human patient, including both genders in adult and child populations.

In the context of the present invention insofar as it relates to any of the disease conditions recited herein, the terms "treat", "treatment", and the like mean to relieve or alleviate at least one symptom associated with such condition, or to slow or reverse the progression of such condition. Within the meaning of the present invention, the term "treat" also denotes to arrest, delay the onset (i.e., the period prior to clinical manifestation of a disease) and/or reduce the risk of developing or worsening a disease. The terms "treat", "treatment", and the like regarding a state, disorder or condition may also include (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms.

The practice of the present invention employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J. Additional techniques are explained, e.g., in U.S. Pat. No. 7,912,698 and U.S. Patent Appl. Pub. Nos. 2011/0202322 and 2011/0307437.

Peptides of the Invention and their Uses

The invention provides a method for manipulating a signaling pathway, i.e., activation or inhibition of Gαi subunits downstream of multiple growth factors in different cell types and in a diverse array of pathophysiologic conditions. More specifically, the invention provides therapeutic effects of cell-permeant peptides that activate or inhibit G proteins downstream of growth factors. In certain embodiments, the invention provides cell-permeant peptides, such as, e.g., wild-type and mutant TAT-GIV-CT peptides, and/or therapeutic agents derived therefrom (e.g., pharmaceutical compositions and expression vectors), and methods of use thereof, including for wound healing, reversing insulin resistance, inhibiting metastasis and fibrosis. The invention also provides genetic modalities of expressing GIV-CT constructs for gene therapy in diverse disease conditions.

In certain embodiments, the invention provides the rationale, validation and effectiveness of a non-genetic technique for manipulating an emerging signaling pathway/paradigm, i.e., transactivation of Gαi subunits by growth factors via the GIV platform. The GIV-CT-containing "activating" peptides of the invention were designed to retain two fundamental properties of the full-length GIV, i.e., activate Gαi by enhancing nucleotide release via. its GEF motif and also interacting with ligand-activated RTKs via its SH2-like motif. As described in the Examples. section, below, it was determined that appending a peptide transduction domain (PTD) such as, e.g., TAT leader sequence, was able to make the GIV-CT peptides cell permeable without altering their functional properties. Additional PTDs useful in the peptides of the invention, include, e.g., PTDs described in Ho et al., Cancer Res, 2001.

Non-limiting examples of additional peptide transduction domains (PTD)/cell penetrating peptides (CPPs) which can be used to impart cell-permeability on the GIV-CT peptides of the invention include those described in Kerkis et al., IUBMB Life, 2006, 58(1):7-13 and Matsumoto et al., Scientific Reports, 2015, 5, Article number: 12884.

Alternatively, the peptides of the invention can be delivered to target cells using viral (e.g., retroviral, lentiviral, etc.) and non-viral (e.g., liposomes, bioballistics etc.) vectors or lipid particles or nanoparticles.

In certain embodiments, the cell-permeable GIV-CT peptides were developed by fusing a TAT-peptide transduction domain (TAT-PTD) to the minimal modular elements of GIV that are necessary and sufficient for activation of Gi downstream of RTKs. In certain embodiments, the minimal modular elements of GIV corresponds to the C-terminus of GIV comprising amino acid residues at 1660-1870 position of human GIV protein ("TAT-GIV-CT peptides"). GenBank provides the following sequence for human GIV protein (GenBank Accession No. BAE44387.1 I/GI:74356043; Accession # AB201172.1; SEQ ID NO: 1): >gi|74356043|dbj|BAE44387.1|girdin [*Homo sapiens*]

MENEIFTPLLEQFMTSPLVTWVKTFGPLAAGNGTNLDEYVALVDGVFLN
QVMLQINPKLESQRVNKKVNNDASLRMHNLSILVRQIKFYYQTLQQLIM
MSLPNVLIIGKNPFSEQGTEEVKKLLLLLLGCAVQCQKKEEFIERIQGL
DFDTKAAVAAHIQEVTHNQENVFDLQWMEVTDMSQEDIEPLLKNMALHL
KRLIDERDEHSETIIELSEERDGLHFLPHASSSAQSPCGSPGMKRTESR
QHLSVELADAKAKIRRLRQELEEKTEQLLDCKQELEQMEIELKRLQQEN
MNLLSDARSARMYRDELDALREKAVRVDKLESEVSRYKERLHDIEFYKA
RVEELKEDNQVLLETKTMLEDQLEGTRARSDKLHELEKENLQLKAKLHD
MEMERDMDRKKIEELMEENMTLEMAQKQSMDESLHLGWELEQISRTSEL
SEAPQKSLGHEVNELTSSRLLKLEMENQSLTKTVEELRTTVDSVEGNAS
KILKMEKENQRLSKKVEILENEIVQEKQSLQNCQNLSKDLMKEKAQLEK
TIETLRENSERQIKILEQENEHLNQTVSSLRQRSQISAEARVKDIEKEN
KILHESIKETSSKLSKIEFEKRQIKKELEHYKEKGERAEELENELHHLE
KENELLQKKITNLKITCEKIEALEQENSELERENRKLKKTLDSFKNLTF
QLESLEKENSQLDEENLELRRNVESLKCASMKMAQLQLENKELESEKEQ
LKKGLELLKASFKKTERLEVSYQGLDIENQRLQKTLENSNKKIQQLESE
LQDLEMENQTLQKNLEELKISSKRLEQLEKENKSLEQETSQLEKDKKQL
EKENKRLRQQAEIKDTTLEENNVKIGNLEKENKTLSKEIGIYKESCVRL
KELEKENKELVKRATIDIKTLVTLREDLVSEKLKTQQMNNDLEKLTHEL
EKIGLNKERLLHDEQSTDDRYKLLESKLESTLKKSLEIKEEKIAALEAR
LEESTNYNQQLRQELKTVKKNYEALKQRQDEERMVQSSPPISGEDNKWE
RESQETTRELLKVKDRLIEVERNNATLQAEKQALKTQLKQLETQNNNLQ
AQILALQRQTVSLQEQNTTLQTQNAKLQVENSTLNSQSTSLMNQNAQLL
IQQSSLENENESVIKEREDLKSLYDSLIKDHEKLELLHERQASEYESLI
SKHGTLKSAHKNLEVEHRDLEDRYNQLLKQKGQLEDLEKMLKVEQEKML
LENKNHETVAAEYKKLCGENDRLNHTYSQLLKETEVLQTDHKNLKSLLN
NSKLEQTRLEAEFSKLKEQYQQLDITSTKLNNQCELLSQLKGNLEEENR
HLLDQIQTLMLQNRTLLEQNMESKDLFHVEQRQYIDKLNELRRQKEKLE
EKIMDQYKFYDPSPPRRRGNWITLKMRKLIKSKKDINRERQKSLTLTPT
RSDSSEGFLQLPHQDSQDSSSVGSNSLEDGQTLGTKKSSMVALKRLPFL
RNRPKDKDKMKACYRRSMSMNDLVQSMVLAGQWTGSTENLEVPDDISTG
KRRKELGAMAFSTTAINFSTVNSSAGFRSKQLVNNKDTTSFEDISPQGV
SDDSSTGSRVHASRPASLDSGRTSTSNSNNNASLHEVKAGAVNNQSRPQ
SHSSGEFSLLHDHEAWSSSGSSPIQYLKRQTRSSPVLQHKISETLESRH
HKIKTGSPGSEVVTLQQFLEESNKLTSVQIKSSSQENLLDEVMKSLSVS
SDFLGKDKPVSCGLARSVSGKTPGDFYDRRTTKPEFLRPGPRKTEDTYF
ISSAGKPTPGTQGKIKLVKESSLSRQSKDSNPYATLPRASSVISTAEGT
TRRTSIHDFLTKDSRLPISVDSPPAAADSNTTAASNVDKVQESRNSKSR
SREQQSS

In certain embodiments, the cell-permeable GIV-CT peptides were developed by fusing a TAT-peptide transduction domain (TAT-PTD) to the minimal modular elements of GIV that are necessary and sufficient for activation of Gi downstream of RTKs. In certain embodiments, the minimal modular elements of GIV corresponds to the C-terminus of GIV comprising amino acid residues at 1660-1870 position ("TAT-GIV-CT peptides"). The TAT-GIV-CT peptides comprise TAT-tag, which provide a reliable means for direct protein transduction into the cell. The TAT-GIV-CT peptides also comprise a linker between TAT and GIV to allow for flexibility. The TAT-GIV-CT peptides also comprise a hexa-histidine tag to allow for affinity purification and a hemagglutinin (HA) tag to allow for detection in cells. Furthermore, the TAT-GIV-CT wild-type peptides comprise the GEF and SH2-like motifs, representing the cross-road between GPCR/G and PTK signaling pathways. The TAT-GIV-CT wild-type peptides also comprise two tyrosines (Y1764 and Y1798) that serve as docking site for p85α (PI3K).

In one specific embodiment, the invention provides TAT-GIV-CT-WT peptide (SEQ ID NO: 2).

```
MetRGSHHHHHHGMetASMetTGGQQMetGRDLYDDDDKDR

WGSKLGYGRKKRRQRRRGGSTMetSGYPYDVPDYAG

SMetGGSGHSGETLESRHHKIKTGSPGSEVVTLQQFLEESN

KLTSVQIKSSSQENLLDEVMetKSLSVSSDFLGKDKPVSCG

LARSVSGKTPGDFYDRRTTKPEFLRPGPRKTEDTYFISSA

GKPTPGTQGKIKLVKESSLSRQSKDSNPYATLPRASSVIST

AEGTTRRTSIHDFLTKDSRLPISVDSPPAAADSNTTAASN

VDKVQESRNSKSRSREQQSStop

HHHHHH (SEQ ID NO: 12) = His tag (6 His aa)

HA Tag (YPYDVPDYA; SEQ ID NO: 13)

GGSGHSG (SEQ ID NO: 11) = Linker

YGRKKRRQRRR (SEQ ID NO: 4) = TAT PTD (11 aa)

GIV-CT (amino acids 1660-1870 of human GIV):
(SEQ ID NO: 14)
ETLESRHHKIKTGSPGSEVVTLQQFLEESNKLTSVQIKSSSQEN LLDEVMetKSLSVSSDFLGKDKPVSCGLARSVSGKTPGDFYDRR

TTKPEFLRPGPRKTEDTYFISSAGKPTPGTQGKIKLVKESSLSR

QSKDSNPYATLPRASSVISTAEGTTRRTSIHDFLTKDSRLPISV

DSPPAAADSNTTAASNVDKVQESRNSKSRSREQQSS.
```

The cell-permeable peptides can be used to engineer signaling networks and alter cell behavior. In the presence of an intact GEF motif, TAT-GIV-CT peptides enhanced diverse processes such as, e.g., 2D cell migration after scratch-wounding, myofibroblast activation and collagen production, and metabolic insulin response in skeletal muscles. Furthermore, topical application of TAT-GIV-CT peptides enhanced wound repair in a GEF-dependent manner. Therefore, the cell-permeable GIV-CT peptides of the invention, e.g., (1) modulate two dimensional cell migration; (2) effectively modulate signaling in human stellate cells; (3) restore insulin sensitivity in insulin resistant skeletal muscle; and (4) accelerate wound healing. The therapeutic potential of these peptides grows as the list of pathophysiologic processes that GIV modulates grows. Pharmaceutical compositions comprising the cell-permeable peptides of the inventions are also provided.

In certain embodiments, the invention provides a method for modulating GIV-dependent cellular signaling pathways in a pathophysiologic condition in a subject in need, comprising administering to said subject an effective amount of the cell permeable peptide, or the pharmaceutical composition of the invention. In certain embodiments, the GIV-dependent cellular signaling pathway is PTK-Gi pathway, wherein the cell permeable peptide serves as a peptide agonist that enhances the PTK-Gi pathway G protein activation. In certain embodiments, the pathophysiologic condition is associated with growth factor cellular response driven by GIV-GEF.

The invention further provides a method for accelerating wound healing in a subject in need thereof, comprising administering to said subject an effective amount of the cell permeable peptide of the invention or a pharmaceutical composition comprising such peptide or a vector encoding such peptide, wherein the cell-permeable peptide enhances, e.g., epithelial 2D-cell migration.

Moreover, the invention provides a method for modulating GIV-dependent metabolic insulin signaling in skeletal muscles and/or adipose tissue in a subject in need thereof, comprising administering to the subject an effective amount of the cell permeable peptide, or a pharmaceutical composition comprising such peptide or a vector encoding such peptide, wherein the cell-permeable peptide effectively reverses insulin resistance (IR) in skeletal muscles and/or adipose tissue. Further, the invention provides a method for regulating glucose uptake on insulin response in skeletal muscles in a subject in need, comprising targeting GIV-GEF motif to control its ability to bind to ligand-activated InsRβ-IRS1 complexes and/or to activate InsR-Gαi protein complexes after insulin simulation. The invention further provides a method for reversing insulin resistance and sensitizing myotubes to the insulin action in skeletal muscles in a subject in need thereof, by increasing the copies of functional GIV-GEF molecules that can overcome the phosphoinhibition of serine residue at position 1689 (Ser1689) of endogenous GIV. The invention also provides mutant GIV-CT peptides in which Serine at position 1689 (Ser1689) is mutated to Alanine (Ala); such a peptide can no longer be phosphoinhibited, and therefore, will maintain GIV-GEF in active state.

In addition to the cell-permeable peptides based on the sequence of wild-type GIV-CT, the invention also provides constitutively active mutants of GIV-CT such as, e.g., S1675D (Bhandari et al., Proc Natl Acad Sci USA, 2015, 112(35):E4874-83).

The invention also provides a method for inhibiting tumor cell invasion (e.g., through the basement membrane matrix) and a method for inhibiting fibrosis in a subject in need thereof, comprising administering to the subject an effective amount of the cell permeable peptide(s) of the invention, which peptide(s) are dominant-negative mutants of wild-type GIV-CT (or a pharmaceutical composition comprising such peptide or a vector encoding such peptide). Non-limiting examples of useful dominant-negative mutants of wild-type GIV-CT include, e.g., F1685A (GEF-deficient), S1689D (GEF-deficient), S1675A (GEF-deficient), and Y1764F+Y1798F (non-phosphorylatable).

The invention further provides a method for modulating GIV-dependent signaling in myofibroblasts in various organs during fibrosis (e.g., in liver-resident myofibroblasts (hepatic stellate cells [HSCs]) during liver fibrosis as well as in myofibroblasts in the muscle and heart) in a subject in need thereof, comprising administering to the subject an effective amount of the cell permeable peptide of the invention or a pharmaceutical composition comprising such peptide or a vector encoding such peptide. Accordingly, the peptides of the invention can be used for treating (halting/reversing) organ fibrosis diseases, including without limitation, liver cirrhosis, liver fibrosis (e.g., non-alcoholic fatty liver disease [NAFLD], non-alcoholic steatohepatitis [NASH], alcoholic fatty liver disease, alcoholic steatohepatitis, hepatic steatosis), skeletal muscle fibrosis, skin fibrosis (e.g., scleroderma, skin fibrosis secondary to burns, keloids, hypertrophic post-surgical wounds), renal fibrosis (e.g., glomerulosclerosis, interstitial-tubular fibrosis), esophageal or gastro-intestinal fibrosis, bone marrow fibrosis (e.g., myelodysplastic syndrome), pulmonary fibrosis, peritoneal fibrosis, pancreatic fibrosis, post-radiation fibrosis, cardiac fibrosis and remodeling after myocardial infarction, brain fibrosis secondary to ischemia or infarcts, post-traumatic brain fibrosis, post-traumatic muscle fibrosis, and synovial/joint fibrosis.

The implications of the invention also include other genetic modalities expressing GIV-CT constructs, such as gene therapy in diverse disease conditions. Non-genetic exogenous modulation of the GIV-Gi signaling interface using cell-penetrable GIV-derived peptides is an effective strategy to reset pathologic signaling networks downstream multiple receptors in a diverse array of pathophysiologic conditions. Thus, TAT-GIV-CT peptides provide a novel and versatile tool to modulate the function of GIV resulting in manipulation of Gαi activation downstream of multiple growth factors in different cell types and in a diverse array of pathophysiologic conditions.

In certain embodiments, the invention provides that the cell-permeable GIV-CT peptides are effective in exogenous modulation of Gi and EGFR signaling, and that TAT-GIV-CT peptides can be used as a versatile strategy to assemble RTKs-Gαi complexes in diverse cell types and trigger activation of Gi downstream of a variety of growth factors. In contrast, the dominant negative GEF-deficient mutant FA peptides which inhibit the formation of RTK-Gαi complexes, offer a strategy for inhibiting aberrant signaling via this pathway. Thus, TAT-GIV-CT-WT serves as a peptide agonist that enhances the RTK-Gi pathway for G protein activation, whereas the FA mutant peptide antagonizes it. Further, in other embodiments, the invention provides that the cell permeable GIV-CT peptides allow manipulation of a diverse array of complex GIV-dependent cellular process.

The impact of these findings is two-fold. First, it confirms that heterotrimeric G-proteins are activated exclusively by GPCRs. The recent work has revealed that RTKs can indeed interact with and activate Gαi (30) during a variety of pathophysiologic processes (7, 14, 21) utilizing the C-terminus of GIV as a platform for such RTK-G protein crosstalk (25). The findings described here using TAT-GIV-CT peptides represent a significant advancement in an ability to access, interrogate and manipulate that platform, and thereby, modulate the cross-talk it facilitates. Second, G-proteins are an ideal target for therapeutic intervention because they serve as signal amplification switches, and potent and pathway-selective activators/inhibitors of a G protein can serve multiple purposes ranging from being a research tool to pharmacologic probe for use in experimental and clinical therapeutics (36). The technique defined here allows exogenous manipulation of the RTK-GIV-Gi pathway by enhancing or suppressing coupling of G protein with RTKs and their subsequent transactivation, in a dose dependent manner while minimizing the risk of tampering with other physiologic functions/interactions of G proteins/or other components within the network of modulators of G protein signaling (37).

The therapeutic advantages of using cell-permeable GIV-CT peptides for activation/inactivation of Gαi are also many-fold. First, it circumvents the need to target individual receptors in diseases that are driven by multiple receptors. Second, GIV's SH2 like domain can directly bind multiple ligand-activated RTKs and re-wire several components of downstream signaling (FIG. 5), and therefore, these peptides offer a versatile tool to simultaneously modulate multiple pathways downstream of many RTKs (i.e., broad), even in diseases/processes where upstream and downstream events are incompletely understood (i.e., circumvents the limitations of unknown). Third, because GIV binds preferentially to Gi subfamily members but can discriminate within this subfamily by binding to Gαi subunits but not to the close homologue Gαo (~75% overall similarity to Gαi1/2/3 subunits) (38), TAT-GIV-CT peptides selectively affect the activation of Gαi1/2/3, but not Gαo (i.e., specific). Fourth, these peptides circumvent the limitation that no promising 'druggable' pockets have been identified within GIV's C-terminus, and that small molecules that can selectively block this platform can be identified. Last, these GIV-CT peptides can be used to directly address the upstream component of RTK-related signaling in cases of mutations, polymorphisms, and expression-related defects often seen in disease.

Thus, the invention provides cell-permeable peptides that allow exogenous modulation of the fundamental function of GIV, i.e., activation of Gi downstream of growth factor RTKs. These peptides provide a versatile tool to manipulate Gαi activation downstream of multiple growth factors in different cell types and in a diverse array of pathophysiologic conditions.

Peptide Modifications and Administration

The peptides of the invention can be modified in various ways to improve their pharmacokinetic and other properties. Peptides can be modified at the amino (N-)terminus, and/or carboxy (C-)terminus and/or by replacement of one or more of the naturally occurring genetically encoded amino acids with an unconventional amino acid, modification of the side chain of one or more amino acid residues, peptide phosphorylation, and the like.

Amino terminus modifications include methylation (e.g., —NHCH$_3$ or —N(CH$_3$)$_2$), acetylation (e.g., with acetic acid or a halogenated derivative thereof such as α-chloroacetic acid, α-bromoacetic acid, or α-iodoacetic acid), adding a benzyloxycarbonyl (Cbz) group, or blocking the amino terminus with any blocking group containing a carboxylate functionality defined by RCOO— or sulfonyl functionality defined by R—SO$_2$—, where R is selected from alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound.

Carboxy terminus modifications include replacing the free acid with a carboxamide group or forming a cyclic lactam at the carboxy terminus to introduce structural constraints. One can also cyclize the peptides of the invention, or incorporate a desamino or descarboxy residue at the termini of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the 20 genetically encoded amino acids (or the stereoisomeric D-amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. For example, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

Common examples of conventional amino acid replacements include stereoisomers (e.g., D-amino acids) and unnatural amino acids such as, for example, L-ornithine, L-homocysteine, L-homoserine, L-citrulline, 3-sulfino-L-alanine, N-(L-arginino)succinate, 3,4-dihydroxy-L-phenylalanine, 3-iodo-L-tyrosine, 3,5-diiodo-L-tyrosine, triiodothyronine, L-thyroxine, L-selenocysteine, N-(L-arginino)taurine, 4-aminobutylate, (R,S)-3-amino-2-methylpropanoate, a,a-disubstituted amino acids, N-alkyl amino acids, lactic acid, β-alanine, 3-pyridylalanine, 4-hydroxyproline, O-phosphoserine, N-methylglycine, N-acetylserine, N-formylmethionine, 3-methylhistidine, 5-hydroxylysine, nor-leucine, and other similar amino acids and imino acids. A general method for site-specific incorporation of unnatural amino acids into proteins and peptides is described in Noren et al., Science, 244:182-188 (April 1989).

One can also readily modify peptides by phosphorylation, and other methods (e.g., as described in Hruby, et al. (1990) Biochem J. 268:249-262).

The peptide compounds of the invention also serve as structural models for non-peptidic compounds with similar biological activity. Those of skill in the art recognize that a variety of techniques are available for constructing compounds with the same or similar desired biological activity as the lead peptide compound, but with more favorable activity than the lead with respect to solubility, stability, and susceptibility to hydrolysis and proteolysis (see, e.g., Morgan and Gainor (1989) Ann. Rep. Med. Chem. 24:243-252). These techniques include replacing the peptide backbone with a backbone composed of phosphonates, amidates, carbamates, sulfonamides, secondary amines, and N-methylamino acids.

The present invention also provides conjugates of the disclosed peptide monomers. Thus, according to a preferred embodiment, the monomeric peptides of the present invention are dimerized or oligomerized, thereby enhancing their biological activity.

In one embodiment, the peptide monomers of the invention may be oligomerized using the biotin/streptavidin system. Biotinylated analogs of peptide monomers may be synthesized by standard techniques. For example, the peptide monomers may be C-terminally biotinylated. These biotinylated monomers are then oligomerized by incubation with streptavidin [e.g., at a 4:1 molar ratio at room temperature in phosphate buffered saline (PBS) or HEPES-buffered RPMI medium (Invitrogen) for 1 hour]. In a variation of this embodiment, biotinylated peptide monomers may be oligomerized by incubation with any one of a number of commercially available anti-biotin antibodies [e.g., goat anti-biotin IgG from Kirkegaard & Perry Laboratories, Inc. (Washington, D.C.)].

Linkers.

In other embodiments, the peptide monomers of the invention can be dimerized by covalent attachment to at least one linker moiety. The linker ($L_K$) moiety can be a $C_{1-12}$ linking moiety optionally terminated with one or two —NH— linkages and optionally substituted at one or more available carbon atoms with a lower alkyl substituent (e.g., —NH—R—NH— wherein R is a lower ($C_{1-6}$) alkylene substituted with a functional group such as a carboxyl group or an amino group, such as, for example, a lysine residue or a lysine amide).

In an additional embodiment, polyethylene glycol (PEG) may serve as the linker $L_K$ that dimerizes two peptide monomers: for example, a single PEG moiety may be simultaneously attached to the N-termini of both peptide chains of a peptide dimer.

In yet another additional embodiment, the linker ($L_K$) moiety is preferably, but not necessarily, a molecule containing two carboxylic acids and optionally substituted at one or more available atoms with an additional functional group such as an amine capable of being bound to one or more PEG molecules. Such a molecule can be depicted as:

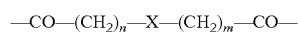

where n is an integer from 0 to 10, m is an integer from 1 to 10, X is selected from O, S, $N(CH_2)_pNR_1$, $NCO(CH_2)_pNR_1$, and $CHNR_1$, $R_1$ is selected from H, Boc, Cbz, etc., and p is an integer from 1 to 10.

Linkers can be incorporated into the peptide during peptide synthesis. For example, where a linker $L_K$ moiety contains two functional groups capable of serving as initiation sites for peptide synthesis and a third functional group (e.g., a carboxyl group or an amino group) that enables binding to another molecular moiety, the linker may be conjugated to a solid support. Thereafter, two peptide monomers may be synthesized directly onto the two reactive nitrogen groups of the linker $L_K$ moiety in a variation of the solid phase synthesis technique.

In alternate embodiments where a peptide dimer is dimerized by a linker $L_K$ moiety, said linker may be conjugated to the two peptide monomers of a peptide dimer after peptide synthesis. Such conjugation may be achieved by methods well established in the art. In one embodiment, the linker contains at least two functional groups suitable for attachment to the target functional groups of the synthesized peptide monomers. For example, a linker with two free amine groups may be reacted with the C-terminal carboxyl groups of each of two peptide monomers. In another example, linkers containing two carboxyl groups, either preactivated or in the presence of a suitable coupling reagent, may be reacted with the N-terminal or side chain amine groups, or C-terminal lysine amides, of each of two peptide monomers.

Spacers.

A peptide monomer or dimer may further comprise one or more spacer moieties. Such spacer moieties may be attached to a peptide monomer or to a peptide dimer (e.g., such spacer moieties may be attached to the linker $L_K$ moiety that connects the monomers of a peptide dimer). For example, such spacer moieties may be attached to a peptide via the carbonyl carbon of a lysine linker, or via the nitrogen atom of an iminodiacetic acid linker. Such a spacer may connect a peptide to an attached water soluble polymer moiety or a protecting group.

In one embodiment, the spacer moiety is a $C_{1-12}$ linking moiety optionally terminated with —NH— linkages or carboxyl (—COOH) groups, and optionally substituted at one or more available carbon atoms with a lower alkyl substituent. In one embodiment, the spacer is R—COOH wherein R is a lower ($C_{1-6}$) alkylene optionally substituted with a functional group such as a carboxyl group or an amino group that enables binding to another molecular moiety. For example, the spacer may be a glycine (G) residue, or an amino hexanoic acid.

In other embodiments, the spacer is —NH—R—NH— wherein R is a lower ($C_{1-6}$) alkylene substituted with a functional group such as a carboxyl group or an amino group that enables binding to another molecular moiety. For example, the spacer may be a lysine (K) residue or a lysine amide (K—$NH_2$, a lysine residue wherein the carboxyl group has been converted to an amide moiety —$CONH_2$).

A spacer can be incorporated into the peptide during peptide synthesis. For example, where a spacer contains a free amino group and a second functional group (e.g., a carboxyl group or an amino group) that enables binding to another molecular moiety, the spacer may be conjugated to the solid support. Thereafter, the peptide may be synthesized directly onto the spacer's free amino group by standard solid phase techniques.

For example, a spacer containing two functional groups is first coupled to the solid support via a first functional group. Next a linker $L_K$ moiety having two functional groups capable of serving as initiation sites for peptide synthesis and a third functional group (e.g., a carboxyl group or an amino group) that enables binding to another molecular moiety is conjugated to the spacer via the spacer's second functional group and the linker's third functional group. Thereafter, two peptide monomers may be synthesized directly onto the two reactive nitrogen groups of the linker $L_K$ moiety in a variation of the solid phase synthesis technique. For example, a solid support coupled spacer with a free amine group may be reacted with a lysine linker via the linker's free carboxyl group.

In alternate embodiments where the peptide compounds contain a spacer moiety, said spacer may be conjugated to the peptide after peptide synthesis. Such conjugation may be achieved by methods well established in the art. In one embodiment, the linker contains at least one functional group suitable for attachment to the target functional group of the synthesized peptide. For example, a spacer with a free amine group may be reacted with a peptide's C-terminal carboxyl group. In another example, a linker with a free carboxyl group may be reacted with the free amine group of a peptide's N-terminus or of a lysine residue. In yet another example, a spacer containing a free sulfhydryl group may be conjugated to a cysteine residue of a peptide by oxidation to form a disulfide bond.

Water Soluble Polymer Moieties.

The peptide monomers, dimers, or multimers of the invention may further comprise one or more water soluble polymer moieties. Preferably, these polymers are covalently attached to the peptide compounds of the invention. Included with the below description, the U.S. patent application Ser. No. 10/844,933 and International Patent Application No. PCT/US04/14887, filed May 12, 2004, are incorporated by reference herein in their entirety.

In recent years, water-soluble polymers, such as polyethylene glycol (PEG), have been used for the covalent modification of peptides of therapeutic and diagnostic importance. Attachment of such polymers is thought to enhance biological activity, prolong blood circulation time, reduce immunogenicity, increase aqueous solubility, and enhance resistance to protease digestion (see, e.g., J. M. Harris, Ed., "Biomedical and Biotechnical Applications of Polyethylene Glycol Chemistry," Plenum, N.Y., 1992; Knauf, et al. (1988) J. Biol. Chem. 263; 15064; Tsutsumi, et al. (1995) J. Controlled Release 33:447; Kita, et al. (1990) Drug Des. Delivery 6:157; Abuchowski, et al. (1977) J. Biol. Chem. 252:582; Beauchamp, et al. (1983) Anal. Biochem. 131:25; Chen, et al. (1981) Biochim. Biophy. Acta 660:293).

The water soluble polymers useful for the peptide compounds of the invention may be, for example, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl pyrrolidone)polyethylene glycol, propropylene glycol homopolymers, polypropylene oxide/ethylene oxide copolymers, and polyoxyethylated polyols.

The water soluble polymer may be of any molecular weight, and may be branched or unbranched. A preferred PEG for use in the present invention comprises linear, unbranched PEG having a low molecular weight. It is understood that in a given preparation of PEG, the molecular weights will typically vary among individual molecules. Some molecules will weight more, and some less, than the stated molecular weight. Such variation is generally reflect by use of the word "about" to describe molecular weights of the PEG molecules.

Peptides, peptide dimers and other peptide-based molecules of the invention can be attached to water-soluble polymers (e.g., PEG) using any of a variety of chemistries to link the water-soluble polymer(s) to the receptor-binding portion of the molecule (e.g., peptide+spacer). A typical embodiment employs a single attachment junction for covalent attachment of the water soluble polymer(s) to the receptor-binding portion, however in alternative embodiments multiple attachment junctions may be used, including further variations wherein different species of water-soluble polymer are attached to the receptor-binding portion at distinct attachment junctions, which may include covalent attachment junction(s) to the spacer and/or to one or both peptide chains. In some embodiments, the dimer or higher order multimer will comprise distinct species of peptide chain (i.e., a heterodimer or other heteromultimer). By way of example and not limitation, a dimer may comprise a first peptide chain having a PEG attachment junction and the second peptide chain may either lack a PEG attachment junction or utilize a different linkage chemistry than the first peptide chain and in some variations the spacer may contain or lack a PEG attachment junction and said spacer, if PEGylated, may utilize a linkage chemistry different than that of the first and/or second peptide chains. An alternative embodiment employs a PEG attached to the spacer portion of the receptor-binding portion and a different water-soluble polymer (e.g., a carbohydrate) conjugated to a side chain of one of the amino acids of the peptide portion of the molecule.

A wide variety of polyethylene glycol (PEG) species may be used for PEGylation of the receptor-binding portion (peptides+spacer). Substantially any suitable reactive PEG reagent can be used. In preferred embodiments, the reactive PEG reagent will result in formation of a carbamate or amide bond upon conjugation to the receptor-binding portion. Suitable reactive PEG species include, but are not limited to, those which are available for sale in the Drug Delivery Systems catalog (2003) of NOF Corporation (Yebisu Garden Place Tower, 20-3 Ebisu 4-chome, Shibuya-ku, Tokyo 150-6019) and the Molecular Engineering catalog (2003) of Nektar Therapeutics (490 Discovery Drive, Huntsville, Ala. 35806). For example and not limitation, the following PEG reagents are often preferred in various embodiments: mPEG2-NHS, mPEG2-ALD, multi-Arm PEG, mPEG (MAL)2, mPEG2(MAL), mPEG-NH2, mPEG-SPA, mPEG-SBA, mPEG-thioesters, mPEG-Double Esters, mPEG-BTC, mPEG-ButyrALD, mPEG-ACET, heterofunctional PEGs (NH2-PEG-COOH, Boc-PEG-NHS, Fmoc-PEG-NHS, NHS-PEG-VS, NHS-PEG-MAL), PEG acrylates (ACRL-PEG-NHS), PEG-phospholipids (e.g., mPEG-DSPE), multiarmed PEGs of the SUNBRITE series including the GL series of glycerine-based PEGs activated by a chemistry chosen by those skilled in the art, any of the SUNBRITE activated PEGs (including but not limited to carboxyl-PEGs, p-NP-PEGs, Tresyl-PEGs, aldehyde PEGs, acetal-PEGs, amino-PEGs, thiol-PEGs, maleimido-PEGs, hydroxyl-PEG-amine, amino-PEG-COOH, hydroxyl-PEG-aldehyde, carboxylic anhydride type-PEG, functionalized PEG-phospholipid, and other similar and/or suitable reactive PEGs as selected by those skilled in the art for their particular application and usage.

The number of polymer molecules attached may vary; for example, one, two, three, or more water soluble polymers may be attached to a peptide of the invention. The multiple attached polymers may be the same or different chemical moieties (e.g., PEGs of different molecular weight). In some cases, the degree of polymer attachment (the number of polymer moieties attached to a peptide and/or the total number of peptides to which a polymer is attached) may be influenced by the proportion of polymer molecules versus peptide molecules in an attachment reaction, as well as by the total concentration of each in the reaction mixture. In general, the optimum polymer versus peptide ratio (in terms of reaction efficiency to provide for no excess unreacted peptides and/or polymer moieties) will be determined by factors such as the desired degree of polymer attachment (e.g., mono, di-, tri-, etc.), the molecular weight of the polymer selected, whether the polymer is branched or unbranched, and the reaction conditions for a particular attachment method.

There are a number of PEG attachment methods available to those skilled in the art (see, e.g., Goodson, et al. (1990) Bio/Technology 8:343; EP 0 401 384; Malik, et al., (1992) Exp. Hematol. 20:1028-1035; PCT Pub. No. WO 90/12874; U.S. Pat. Nos. 5,757,078; and 6,077,939). For example, activated PEG may be covalently bound to amino acid residues via a reactive group, such as a free amino group in N-terminal amino acid residues and lysine (K) residues or a free carboxyl group in C-terminal amino acid residues. Sulfhydryl groups (e.g., as found on cysteine residues) may also be used as a reactive group for attaching PEG. In addition, enzyme-assisted methods for introducing activated groups (e.g., hydrazide, aldehyde, and aromatic-amino groups) specifically at the C-terminus of a polypeptide have been described (Schwarz, et al. (1990) Methods Enzymol. 184:160; Rose, et al. (1991) Bioconjugate Chem. 2:154; Gaertner, et al. (1994) J. Biol. Chem. 269:7224).

For example, PEG molecules may be attached to peptide amino groups using methoxylated PEG ("mPEG") having different reactive moieties. Such polymers include mPEG-succinimidyl succinate, mPEG-succinimidyl carbonate, mPEG-imidate, mPEG-4-nitrophenyl carbonate, and mPEG-cyanuric chloride. Similarly, PEG molecules may be attached to peptide carboxyl groups using methoxylated PEG with a free amine group ($mPEG-NH_2$).

Where attachment of the PEG is non-specific and a peptide containing a specific PEG attachment is desired, the desired PEGylated compound may be purified from the mixture of PEGylated compounds. For example, if an N-terminally PEGylated peptide is desired, the N-terminally PEGylated form may be purified from a population of randomly PEGylated peptides (i.e., separating this moiety from other monoPEGylated moieties).

Site-specific PEGylation at the N-terminus, side chain, and C-terminus can be performed through (i) solid-phase synthesis (see, e.g., Felix, et al. (1995) Int. J. Peptide Protein Res. 46:253) or (ii) attaching a peptide to extremities of liposomal surface-grafted PEG chains in a site-specific manner through a reactive aldehyde group at the N-terminus generated by sodium periodate oxidation of N-terminal threonine (see, e.g., Zalipsky, et al. (1995) Bioconj. Chem. 6:705; this method is limited to polypeptides with N-terminal serine or threonine residues), or (iii) via a hydrazone, reduced hydrazone, oxime, or reduced oxime bond is described in U.S. Pat. No. 6,077,939.

In one method, selective N-terminal PEGylation may be accomplished by reductive alkylation which exploits differential reactivity of different types of primary amino groups (lysine versus the N-terminal) available for derivatization in a particular protein. Under the appropriate reaction conditions, a carbonyl group containing PEG is selective attached to the N-terminus of a peptide. For example, one may selectively N-terminally PEGylate the protein by performing the reaction at a pH which exploits the $pK_a$ differences between the ε-amino groups of a lysine residue and the α-amino group of the N-terminal residue of the peptide. By such selective attachment, PEGylation takes place predominantly at the N-terminus of the protein, with no significant modification of other reactive groups (e.g., lysine side chain amino groups). Using reductive alkylation, the PEG should have a single reactive aldehyde for coupling to the protein (e.g., PEG proprionaldehyde may be used).

Site-specific mutagenesis is a further approach which may be used to prepare peptides for site-specific polymer attachment. By this method, the amino acid sequence of a peptide is designed to incorporate an appropriate reactive group at the desired position within the peptide. For example, WO 90/12874 describes the site-directed PEGylation of proteins modified by the insertion of cysteine residues or the substitution of other residues for cysteine residues.

Where PEG is attached to a spacer or linker moiety, similar attachment methods may be used. In this case, the linker or spacer contains a reactive group and an activated PEG molecule containing the appropriate complementary reactive group is used to effect covalent attachment. In preferred embodiments the linker or spacer reactive group contains a terminal amino group (i.e., positioned at the terminus of the linker or spacer) which is reacted with a suitably activated PEG molecule to make a stable covalent bond such as an amide or a carbamate. Suitable activated PEG species include, but are not limited to, mPEG-para-nitrophenylcarbonate (mPEG-NPC), mPEG-succinimidyl carbonate (mPEG-SC), and mPEG-succinimidyl propionate (mPEG-SPA). In other preferred embodiments, the linker or spacer reactive group contains a carboxyl group capable of being activated to form a covalent bond with an amine-containing PEG molecule under suitable reaction conditions. Suitable PEG molecules include mPEG-NH$_2$ and suitable reaction conditions include carbodiimide-mediated amide formation or the like.

The peptides of the invention may be prepared by classical methods known in the art. These standard methods include exclusive solid phase synthesis, automated solid phase synthesis, partial solid phase synthesis methods, fragment condensation, classical solution synthesis, and recombinant DNA technology (See, e.g., Merrifield J. Am. Chem. Soc. 1963 85:2149 and Merrifield et al., 1982, Biochemistry, 21:502).

A preferred method for peptide synthesis is solid phase synthesis. Solid phase peptide synthesis procedures are well-known in the art (see, e.g., Stewart, *Solid Phase Peptide Syntheses*, Freeman and Co.: San Francisco, 1969; 2002/2003 General Catalog from Novabiochem Corp, San Diego, USA; Goodman, *Synthesis of Peptides and Peptidomimetics*, Houben-Weyl, Stuttgart 2002). In solid phase synthesis, synthesis is typically commenced from the C-terminal end of the peptide using an α-amino protected resin. A suitable starting material can be prepared, for instance, by attaching the required α-amino acid to a chloromethylated resin, a hydroxymethyl resin, a polystyrene resin, a benzhydrylamine resin, or the like. One such chloromethylated resin is sold under the trade name BIO-BEADS SX-1 by Bio Rad Laboratories (Richmond, Calif.). The preparation of the hydroxymethyl resin has been described (Bodonszky, et al. (1966) Chem. Ind. London 38:1597). The benzhydrylamine (BHA) resin has been described (Pietta and Marshall, 1970, Chem. Commun., 650), and the hydrochloride form is commercially available from Beckman Instruments, Inc. (Palo Alto, Calif.). For example, an α-amino protected amino acid may be coupled to a chloromethylated resin with the aid of a cesium bicarbonate catalyst, according to the method described by Gisin (1973, Helv. Chim. Acta 56:1467).

After initial coupling, the α-amino protecting group is removed, for example, using trifluoroacetic acid (TFA) or hydrochloric acid (HCl) solutions in organic solvents at room temperature. Thereafter, α-amino protected amino acids are successively coupled to a growing support-bound peptide chain. The α-amino protecting groups are those known to be useful in the art of stepwise synthesis of peptides, including: acyl-type protecting groups (e.g., formyl, trifluoroacetyl, acetyl), aromatic urethane-type protecting groups [e.g., benzyloxycarboyl (Cbz) and substituted Cbz], aliphatic urethane protecting groups [e.g., t-butyloxycarbonyl (Boc), isopropyloxycarbonyl, cyclohexyloxycarbonyl], and alkyl type protecting groups (e.g., benzyl, triphenylmethyl), fluorenylmethyl oxycarbonyl (Fmoc), allyloxycarbonyl (Alloc), and 1-(4,4-dimethyl-2, 6-dioxo-cyclohex-1-ylidene)ethyl (Dde).

The side chain protecting groups (typically ethers, esters, trityl, PMC (2,2,5,7,8-pentamethyl-chroman-6-sulphonyl), and the like) remain intact during coupling and is not split off during the deprotection of the amino-terminus protecting group or during coupling. The side chain protecting group must be removable upon the completion of the synthesis of the final peptide and under reaction conditions that will not alter the target peptide. The side chain protecting groups for Tyr include tetrahydropyranyl, tert-butyl, trityl, benzyl, Cbz, Z—Br—Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting groups for Arg include nitro, Tosyl (Tos), Cbz, adamantyloxycarbonyl mesitoylsulfonyl (Mts), 2,2,4,6,7-pentamethyldihydrobenzofurane-5-sulfonyl (Pbf), 4-methoxy-2,3,6-trimethyl-benzenesulfonyl (Mtr), or Boc. The side chain protecting groups for Lys include Cbz, 2-chlorobenzyloxycarbonyl (2-Cl-Cbz), 2-bromobenzyloxycarbonyl (2-Br-Cbz), Tos, or Boc.

After removal of the α-amino protecting group, the remaining protected amino acids are coupled stepwise in the desired order. Each protected amino acid is generally reacted in about a 3-fold excess using an appropriate carboxyl group activator such as 2-(1H-benzotriazol-1-yl)-1,1,3,3 tetramethyluronium hexafluorophosphate (HBTU) or dicyclohexylcarbodiimide (DCC) in solution, for example, in methylene chloride (CH$_2$Cl$_2$), N-methyl pyrrolidone, dimethyl formamide (DMF), or mixtures thereof.

After the desired amino acid sequence has been completed, the desired peptide is decoupled from the resin support by treatment with a reagent, such as trifluoroacetic acid (TFA) or hydrogen fluoride (HF), which not only cleaves the peptide from the resin, but also cleaves all remaining side chain protecting groups. When a chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides. In preparing the esters of the invention, the resins used to prepare the peptide acids are employed, and the side chain protected peptide is cleaved with base and the appropriate alcohol (e.g., methanol). Side chain protecting groups are then removed in the usual fashion by treatment with hydrogen fluoride to obtain the desired ester. The resultant peptide can be further purified using HPLC.

These procedures can also be used to synthesize peptides in which amino acids other than the 20 naturally occurring, genetically encoded amino acids are substituted at one, two, or more positions of any of the compounds of the invention. Synthetic amino acids that can be substituted into the peptides of the present invention include, but are not limited to, N-methyl, L-hydroxypropyl, L-3, 4-dihydroxyphenylalanyl, δ amino acids such as L-☐ δ-hydroxylysyl and D-☐ δ-methylalanyl, L-δ-methylalanyl, β amino acids, and isoquinolyl. D-amino acids and non-naturally occurring synthetic amino acids can also be incorporated into the peptides of the present invention.

In addition to chemical synthesis, the peptides of the present invention may be synthesized by employing recombinant DNA technology by expressing one or more polynucleotide comprising a peptide coding region. Thus, provided herein are isolated polynucleotides that encode the peptides of the present invention as well as recombinant vectors and host cells (both eukaryotic and prokaryotic) that have been genetically modified to express or overexpress the peptides of the present invention.

In one embodiment, the invention provides isolated polynucleotides (e.g., vectors) comprising nucleotide sequences encoding the peptides of the invention.

Expression may be achieved in any conventional expression system known in the art by isolating a DNA fragment encoding the peptide of interest and cloning into an expression vector.

Useful compounds of the present invention are not limited to peptides incorporating natural and/or non-natural amino acids. The invention also encompasses various peptidomimetics such as, e.g., peptoids (a class of peptidomimetics whose side chains are appended to the nitrogen atom of the peptide backbone, rather than to the α-carbons). A number of non-peptide molecules having similar functional properties to the peptides of the invention can be developed to incorporate disparate chemical functional groups within a single molecule. These molecules are often referred to as scaffolding molecules, or scaffolds, since they can accommodate a wide range of chemical functionality and can be designed to present the chemical functional groups in a wide array of relative geometric orientations in space. Molecular scaffold systems include, but are not limited to, carbohydrates (see, e.g., Tamaruya et al., Angew Chem. Int. Ed. Engl., 2004, 43(21):2834-7), peptide nucleic acids (PNA's), (see, e.g., Peptide Nucleic Acids: Protocols and Applications, 2nd ed., Peter E. Nielsen, ed., Horizon Bioscience, 2004) and molecules not derived from biological precursors (see, e.g., Savinov and Austin, Org. Lett., 2002, 4(9):1419-22). The incorporation of this diverse a set of chemistries may require chemical protection of reactive functionality during synthesis. These techniques are well known in the art and can be found in references such as T. W. Green, P. G. M. Wuts, Protective Groups in Organic Synthesis, Wiley-Interscience, New York, 1999.

Peptides and their derivatives disclosed herein may be formulated as compositions together with a pharmaceutically acceptable carrier (such as an adjuvant or vehicle) and/or excipient, and/or diluents. Compositions of this invention may include pharmaceutically acceptable salts of the components therein. Pharmaceutically acceptable salts include the acid addition salts (formed with the free amino groups of the peptide) that are formed with inorganic acids such as, for example, hydrochloric or phosphoric acids, or such organic acids as acetic, tartaric, mandelic and the like. Salts formed with the free carboxyl groups can be derived from inorganic bases such as, for example, sodium, potassium, ammonium, calcium or ferric hydroxides, and such organic bases as isopropylamine, trimethylamine, 2-ethylamino ethanol, histidine, procaine and the like.

Pharmaceutically acceptable carriers are familiar to those skilled in the art and can include sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin. For compositions formulated as liquid solutions, acceptable carriers and diluents include saline and sterile water, and may optionally include antioxidants, buffers, bacteriostats, and other common additives. The compositions can also be formulated as pills, capsules, granules, or tablets which may contain, in addition to a peptide of this invention, diluents, dispersing and surface active agents, binders, and lubricants. Proper formulation is dependent upon the route of administration chosen.

The optimal therapeutically effective amount of a compound or composition of this invention may be determined experimentally, taking into consideration the exact mode of administration, the form in which the drug is administered, the indication toward which the administration is directed, the subject involved (e.g., body weight, health, age, sex, etc.), and the preference and experience of the physician or veterinarian in charge.

The efficacy of the peptides and compositions of this invention can be determined using the in vitro and in vivo assays described in the Examples section, below.

Following methodologies which are well-established in the art, effective doses and toxicity of the peptides and compositions of the present invention, which performed well in in vitro tests, can be determined in studies using small animal models (e.g., mice, rats or dogs) in which they have been found to be therapeutically effective and in which these drugs can be administered by the same route proposed for the human trials.

For any pharmaceutical composition used in the methods of the invention, dose-response curves derived from animal systems can be used to determine testing doses for administration to humans. In safety determinations for each composition, the dose and frequency of administration should meet or exceed those anticipated for use in any clinical trial.

As disclosed herein, the dose of the compound in the compositions of the present invention is determined to ensure that the dose administered continuously or intermittently will not exceed an amount determined after consideration of the results in test animals and the individual conditions of a patient. A specific dose naturally varies (and is ultimately decided according to the judgment of the practitioner and each patient's circumstances) depending on the dosage procedure, the conditions of a patient or a subject animal such as age, body weight, sex, sensitivity, feed, dosage period, drugs used in combination, seriousness of the disease, etc.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$.

All known peptide delivery methods can be used to deliver the peptides of the present invention to the target tissues. The specific type of delivery useful for a given peptide is determined by its specific size, flexibility, conformation, biochemical properties of constituent amino acids, and amino acid arrangement. Peptide composition also determines, in part, the degree of protein binding, enzymatic stability, cellular sequestration, uptake into non-target tissue, clearance rate, and affinity for protein carriers. Other aspects independent of peptide composition must also be considered, such as cerebral blood flow, diet, age, sex, species (for experimental studies), dosing route, and effects of existing pathological conditions.

The peptides and/or the pharmaceutical composition comprising the peptides of the invention can be administered to a subject (e.g., human or animal) in need via various administration routes, including, but not limited to, systemic administration, inhalation, topical, sublingual, oral, intranasal, and/or direct instillation (e.g, intratracheal instillation for lung treatment). Non-limiting examples of useful administration routes for the peptides and peptide-encoding vectors of the invention include, e.g., systemic (including tumor-targeted) administration, topical or local administration, administration to mucosal surfaces of mouth or bowel (e.g., by enema), and inhalation.

The peptides of the invention can be formulated for any suitable administration, with or without any pharmaceutically acceptable carrier, excipients, solvents, and/or solutions, and in certain proper dosage.

Examples of delivery methods useful for obtaining effective tissue delivery of the peptides of the invention (and effective passage through the blood-brain-barrier [BBB] in case of brain tissues), include, without limitation (reviewed, e.g., in Witt and Davis, AAPS Journal, 2006; 8(1): E76-E88):
(i) invasive procedures (e.g., direct injection [e.g., using an external pump or i.v. line], transient osmotic opening, shunts, and biodegradable implants);
(ii) pharmacologically-based approaches to increase the tissue delivery by chemical modification of the peptide molecule itself, or by the attachment or encapsulation of the peptide in a substance that increases permeability, stability, bioavailability, and/or receptor affinity; in addition, modification of a peptide structure and/or addition of constituents (e.g., lipophilicity enhancers, polymers, antibodies) may enhance local peptide concentration in the target tissue;
(iii) physiologic-based strategies which exploit various carrier mechanisms; these strategies can be combined, dependent of the nature of a given peptide, creating "hybrid" peptides, resulting in synergistic delivery and end-effect.

Specific examples of peptide modifications and methods useful for improving delivery of the peptides of the invention include, without limitation, lipidization (e.g., methylation, dimethylation, or halogenation of constituent amino acids or acylation or alkylation of the N-terminal amino acid), structural modification to enhance stability (e.g., use of D-amino acids, N-acylation, or cyclization, e.g., via a disulfide-bridge or via a hydrazide bridge), glycosylation (e.g., adding simple sugars such as, e.g., glucose or xylose), increasing affinity for nutrient transporters (e.g., adding hexose or large neutral amino acid carriers which facilitate delivery of substrates to the brain), forming a prodrug by conjugating a peptide to a molecule with a known transporter activity or to a lipophilicity enhancer, which is cleaved at or near the site of action (e.g., using esterification [with, e.g., aromatic benzoyl esters or branched chain tertiary butyl esters] or amidation of amino, hydroxyl, or carboxylic acid-containing peptides; also, redox system-mediated delivery to the brain may be facilitated using conjugation to a methyldihydropyridine carrier and subsequent oxidation by NADH-linked dehydrogenases in the brain, which results in a quaternary ammonium salt, which does not cross back through the BBB endothelium), vector-based delivery (e.g., by coupling a peptide to a substance that increases the affinity to and transport across biological membranes via receptor-mediated or absorptive-mediated endocytosis followed by peptide release via enzymatic cleavage [e.g., conjugation of a peptide to murine monoclonal antibody (OX26) to the transferrin or conjugation to cationized albumin to increase brain uptake]), cationization to increase membrane entry via absorptive-mediated endocytosis, and polymer conjugation/encapsulation (e.g., conjugation to poly(ethylene glycol) [PEG] or poly(styrene maleic acid) or encapsulation via micro- or nano-particles [e.g., polymeric nanoparticles ranging in size between 10 and 1000 nm, which have a polysorbate overcoating such as, e.g., polysorbate-80], liposomes [e.g., surface-modified long-circulating liposomes grafted with a flexible hydrophilic polymer such as, e.g., PEG and/or liposomes composed of a phospholipid bilayer such as, e.g., pluronic copolymer P85, that act as a carrier for both hydrophilic and hydrophobic peptides], micelles [e.g., stable polymeric micelles prepared from amphiphilic PEG-phospholipid conjugates], or cell ghosts). Reviewed in Torchilin and Lukyanov, D D T, 2003, 8(6): 259-266; Egleton and Davis, NeuroRx, 2005, 2: 44-53; Witt and Davis, AAPS Journal, 2006; 8(1): E76-E88.

Regardless of the delivery method used, an important aspect of the present invention is to keep the size of the resulting delivered peptide sufficiently small (e.g., by using cleavable conjugates).

Oral Delivery.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include a peptide of the invention (or chemically modified forms thereof) and inert ingredients which allow for protection against the stomach environment, and release of the biologically active material in the intestine.

Also contemplated for use herein are liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

As discussed above, the peptides may be chemically modified so that oral delivery of the derivative is efficacious. Generally, the chemical modification contemplated is the attachment of at least one moiety to the component molecule itself, where said moiety permits (a) increase in peptide stability (e.g., by inhibition of proteolysis) and (b) efficient uptake into the blood stream from the stomach or intestine. As discussed above, common delivery-improving peptide modifications include PEGylation or the addition of moieties such as propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane (see, e.g., Abuchowski and Davis (1981) "Soluble Polymer-Enzyme Adducts," in *Enzymes as Drugs*. Hocenberg and Roberts, eds. (Wiley-Interscience: New York, N.Y.) pp. 367-383; and Newmark, et al. (1982) J. Appl. Biochem. 4:185-189).

For oral formulations, the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the peptide (or derivative) or by release of the peptide (or derivative) beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used.

The peptide (or derivative) can be included in the formulation as fine multiparticulates in the form of granules or pellets of particle size about 1 mm. The formulation of the material for capsule administration could also be as a powder, lightly compressed plugs, or even as tablets. These therapeutics could be prepared by compression.

Colorants and/or flavoring agents may also be included. For example, the peptide (or derivative) may be formulated (such as by liposome or microsphere encapsulation) and then further contained within an edible product, such as a refrigerated beverage containing colorants and flavoring agents.

One may dilute or increase the volume of the peptide (or derivative) with an inert material. These diluents could include carbohydrates, especially mannitol, lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress, and Avicel.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. The disintegrants may also be insoluble cationic exchange resins. Powdered gums may be used as disintegrants and as binders. and can include powdered gums such as agar, Karaya or tragacanth. Alginic acid and its sodium salt are also useful as disintegrants.

Binders may be used to hold the peptide (or derivative) agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the peptide (or derivative).

An antifrictional agent may be included in the formulation of the peptide (or derivative) to prevent sticking during the formulation process. Lubricants may be used as a layer between the peptide (or derivative) and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the peptide (or derivative) into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the peptide (or derivative) are for instance the fatty acids oleic acid, linoleic acid and linolenic acid.

Controlled release oral formulations may be desirable. The peptide (or derivative) could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The peptide (or derivative) could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Parenteral Delivery.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Administration by Inhalation and Intranasal Administration.

The present invention encompasses any delivery device that is suitable for administration by inhalation or intranasal administration of the compositions of the invention. Preferably, such means administers a metered dosage of the composition. The composition of the present invention may be packed in any appropriate form or container as long as a means is provided to deliver the composition to the oral or lung or nasal mucosa. Non-limiting examples of useful delivery devices include, e.g., instillation catheters, droppers, unit-dose containers, squeeze bottles pump sprays, airless and preservative-fee sprays, compressed air nebulizers, metered-dose inhalers, insufflators and pressurized metered dose inhalers. For administration of a liquid in drop form, compositions of the invention can be placed in a container provided with a conventional dropper/closure device, e.g. comprising a pipette or the like, preferably delivering a substantially fixed volume of composition/drop. For administration of an aqueous solution as a spray, the aqueous solution may be dispensed in spray form by a variety of methods known to those skilled in the art. For example, such compositions will be put up in an appropriate atomising device, e.g. in a pump-atomiser, or the like. The atomising device will be provided with appropriate means, such as a spray adaptor for delivery of the aqueous spray to the naris. Preferably it will be provided with means ensuring delivery of a substantially fixed volume of composition/actuation (i.e. per spray-unit). Examples of nasal sprays include nasal actuators produced by Ing. Erich Pfeiffer GmbH, Radolfzell, Germany (see U.S. Pat. Nos. 4,511,069, 4,778,810, 5,203,840, 5,860,567, 5,893,484, 6,227,415, and 6,364,166. Additional aerosol delivery forms may include, e.g., compressed air-, jet-, ultrasonic-, and piezoelectric nebulizers. Alternatively the spray may be bottled under pressure in an aerosol device. The propellant may be a gas or a liquid (e.g. a fluorinated and/or chlorinated hydrocarbon). The spray composition may be suspended or dissolved in a liquid propellant. Stabilizing and/or suspending agents and/or co-solvents may be present. A dry powder may be readily dispersed in an inhalation device as described in U.S. Pat. No. 6,514,496 and Garcia-Arieta et al., Biol. Pharm. Bull. 2001; 24: 1411-1416. If desired a powder or liquid may be filled into a soft or hard capsule or in a single dose device adapted for nasal administration. The powder may be sieved before filled into the capsules such as gelatine capsules. The delivery device may have means to break open the capsule. The powdery nasal composition can be directly used as a powder for a unit dosage form. The contents of the capsule or single dose device may be administered using e.g. an insufflator. Preferably it will be provided with means ensuring dosing of a substantially fixed amount of composition.

In another embodiment, the composition of the invention can be provided as a nasal insert having the peptide(s) of the invention. The insert may be retained in the naris, but flushed by the nasal mucus, and may be designed to release the Peptide, fragment or derivative of the invention at the same place in the naris. Suitable nasal insert types include nasal plugs, tampons and the like. Further examples of nasal inserts, their characteristics and preparation are described in EP 490806.

Delivery devices are important not only for delivering the peptides of the invention, but also for providing an appropriate environment for storage. This would include protection from microbial contamination and chemical degradation. The device and formulation should be compatible so as to avoid potential leaching or adsorption. The delivery device (or its packaging) can be optionally provided with a label and/or with instructions for use.

The peptides of the invention can be administered using any standard administration route and technique known in the art. The peptides can also be delivered using a vector (such as a viral vector) with the ability to express a peptide of this invention.

The Therapeutic Target and its Potential Clinical Relevance

The invention further defines activation of Gαi by GIV's GEF function as a central node that coordinately enhances the physiologic insulin response and its deregulation herald insulin resistance (IR). Because this node also serves as the point of convergence for the antagonistic actions of fatty acids and insulin sensitizers, selective modulation of this node emerges as a promising and precise strategy to treat T2DM and other conditions where IR plays a central pathophysiologic role.

In certain embodiments, the invention provides that activation of Gαi by GIV-GEF is required for glucose uptake in skeletal muscles, and cell permeant GIV-derived peptides can effectively reserve insulin resistance in skeletal muscle. In other embodiments, the invention provides that GIV binds ligand activated InsRβ kinase activity and autophosphorylation, and modulates multiple tiers of metabolic insulin signaling via its GEF function. In yet other embodiments, the invention provides that GIV directly binds and modulates the localization and functional phosphorylation of IRS1. In certain embodiments, the invention provides that GIV provides the necessary molecular basis for IRS1 to serve as a common conduit for metabolic response downstream of receptors other than InsRβ. Further, the invention provides that GIV enhances tyrosine phosphorylation of IRS1, maximizes PM-recruitment, and coordinates membrane trafficking within the insulin response cascade.

In certain embodiments, the invention provides that phosphorylation of GIV-GEF motif at S1689 position by PKCθ triggers lipid-induced insulin resistance, and TZDs, like pioglitazone, release the phosphoinhibition on GIV-GEF, suggesting that reversible phosphorylation of GIV-GEF at S1689 and inhibition of the GEF function via which GIV activates Gαi, serves as a molecular switch for flipping skeletal muscles between insulin-sensitive and resistant states. In yet other embodiments, the invention provides that GIV-GEF is a target for the antagonist actions of fatty acids and insulin sensitizers. Since many of GIV's modules, not just its C-terminal GEF motif may play a role in integrating signaling events with vesicular trafficking and cytoskeletal changes to orchestrate glucose uptake after insulin simulation, selective modulation of GIV-GEF emerges as a therapeutic strategy for reversal of IR.

Various publications, including patents, published applications, technical articles and scholarly articles are cited throughout the specification. Each of these cited publications is incorporated by reference herein, in its entirety.

Unless defined otherwise, all technical and scientific terms used herein have the same meaning as commonly understood by one of ordinary skill in the art to which the invention pertains. Other specifically defined terms are to be construed in a manner consistent with the definition provided herein. Although any methods and materials similar or equivalent to those described herein can be used in the practice for testing of the present invention, the preferred materials and methods are described herein. In describing and claiming the present invention, the following terminology will be used.

Other embodiments and uses are apparent to one skilled in the art in light of the present disclosures. Those skilled in the art will appreciate that numerous changes and modifications can be made to the embodiments of the invention and that such changes and modifications can be made without departing from the spirit of the invention. It is, therefore, intended that the appended claims cover all such equivalent variations as fall within the true spirit and scope of the invention.

Throughout the specification various citations are referenced, and the entire content of each is hereby incorporated by reference. The following example is provided to describe the invention in more detail. It is intended to illustrate, not to limit the invention.

EXAMPLES

Example 1

Therapeutic Effects of Cell-Permeant Peptides that Activate G Proteins Downstream of Growth Factors This example provides cell-permeable GIV-CT peptides and their effects to activate G proteins downstream of growth factor. Here, cell-permeable GIV-CT peptides were developed by fusing a TAT-peptide transduction domain (TAT-PTD) to the minimal modular elements of GIV that are necessary and sufficient for activation of Gi downstream of RTKs, and used them to engineer signaling networks and alter cell behavior. In the presence of an intact GEF motif, TAT-GIV-CT peptides enhanced diverse processes in which GIV's GEF function has previously been implicated; e.g., 2D cell migration after scratch-wounding, invasion of cancer cells, myofibroblast activation and collagen production and finally, metabolic insulin response in skeletal muscles. Furthermore, topical application of TAT-GIV-CT peptides enhanced wound repair in mice in a GEF-dependent manner. Thus, TAT-GIV peptides provide a novel and versatile tool to manipulate Gαi activation downstream of growth factors in a diverse array of pathophysiologic conditions.

Experimental Procedures

Reagents and Antibodies.

Unless otherwise indicated, all reagents were of analytical grade and obtained from Sigma-Aldrich. Cell culture media were purchased from Invitrogen. Epidermal growth factor (EGF), insulin was purchased from Invitrogen and Novagen, respectively. All restriction endonucleases and *Escherichia coli* strain DH5α were purchased from New England Biolabs. *E. coli* BL21 (DE3 strain) and phalloidin-Texas Red were purchased from Invitrogen. DAPI was purchased from Molecular Probes (Invitrogen). PfuUltra DNA polymerase was purchased from Stratagene. Goat anti-rabbit and goat anti-mouse Alexa Fluor 680 or IRDye 800 F(ab')2 used for Odyssey Infrared Imaging were from Li-Cor Biosciences. Mouse mAbs against hexahistidine (His) and α-tubulin were obtained from Sigma-Aldrich. Rabbit anti-GIV-CT (T-13) was from Santa Cruz Biotechnology, and phospho-Akt (S473), phosphor SMAD2/3 and phosphoEGFR (Y1068) were from Cell Signaling. Rabbit anti-PKCθ was obtained from GeneTex.

Plasmid Constructs, Mutagenesis, and Protein Expression.

Cloning of TAT-GIV-CT was carried out by amplifying a short flexible linker (FIG. 1A) and the stretch of human GIV-CT (amino acids 1660-1870) en bloc from CFP-GIV-CT (43) and inserting it between Nco1/Kpn1 of pTAT-HA. TAT-GIV-CT-FA mutant was generated using QuikChange II (Stratagene) and specific primers (sequence available upon request) following the manufacturer's instructions. Cloning of rat Gαi3 into pGEX-4T-1 has been described (44). Internally tagged Gαi1-YFP, Gαi3-YFP, Gαi3-CFP, Gβ1-CFP, and GY2 constructs were generous gifts from Moritz Bunemann (45, 46).

Lentiviral vectors for Cre-inducible stable depletion of GIV in HeLa cells lines were designed as follows. First, shRNA targets for GIV in its 3' UTR were identified using the pSicoOligomaker 1.5 software. Hairpin loops were cloned containing a sequence (hGIVsh GGAATGTAC-TATATAGCAA, SEQ ID NO: 15; GenBank Accession No. BAE44387.1, AB201172.1; Entrez Gene: CCDC88A) against human GIV into the pSico-PGK-puro vector. The numbers in parenthesis indicate the nucleotide positions in the mRNA of GIV (GenBank Accession no. AB201172.1). Cloning of control shLUC viruses (targeting luciferase) have been described (47).

TAT-constructs were expressed using BL21(DE3)-pLysS (Invitrogen) and Terrific Broth (BioPioneer) supplemented with additives as per auto-induction protocols outlined by Studier F (48). Briefly, cultures of bacteria were grown at 300 rpm at 37° C. for 5 h, then at 25° C. overnight. Cells were lysed in 10 mL of buffer [20 mM Tris, 10 mM Imidazole, 400 mM NaCl, 1% (vol:vol) Sarkosyl, 1% (vol:vol) Triton X-100, 2 mM DTT, 2 mM Na3oV4 and protease inhibitor mixture (Roche Diagnostics) (pH 7.4)], sonicated (3 Å~30 s), cleared at 12,000 Å~g for 20 min at 4° C. and affinity-purified on Ni-NTA agarose resin (Qiagen) (4 h at 4° C.). Proteins were eluted in elution buffer [20 mM Tris, 300 mM Imidazole, 400 mM NaCl, pH 7.4], dialyzed overnight against TBS containing 400 mM NaCl and stored at −80° C.

GST and GST-Gαi3 fusion constructs were expressed in *E. coli* strain BL21(DE3) (Invitrogen) and purified as described previously (44, 49, 50). Briefly, bacterial cultures were induced overnight at 25° C. with 1 mM isopropyl β-D-1-thiogalactopyranoside (IPTG). Pelleted bacteria from 1 L of culture were resuspended in 10 mL GST-lysis buffer [25 mM Tris-HCl, pH 7.5, 20 mM NaCl, 1 mM EDTA, 20% (vol:vol) glycerol, 1% (vol:vol) Triton X-100, 2×protease inhibitor mixture (Complete EDTA-free, Roche Diagnostics)] or His-lysis buffer [50 mM NaH2PO4 pH 7.4, 300 mM NaCl, 10 mM imidazole, 1% (vol:vol) Triton X-100, 2 Å~protease inhibitor mixture (Complete EDTA-free, Roche Diagnostics)] for GST or His-fused proteins, respectively. After sonication (4×20 s, 1 min between cycles), lysates were centrifuged at 12,000 g at 4° C. for 20 min. Solubilized proteins were affinity purified on glutathione-Sepharose 4B beads (GE Healthcare) or HisPur Cobalt Resin (Pierce). Proteins were eluted, dialyzed overnight against PBS and stored at −80° C.

Cell Culture, Lysis, and Quantitative Immunoblotting.

HeLa and MDA MB231 cells were cultured according to ATCC guidelines in the presence of DMEM supplemented with 10% FBS and antibiotics. The Lx2 human hepatic stellate cell line was obtained from Scott Friedman (Mount Sinai, N.Y.) and were cultured in DMEM media containing 2% FBS according to previously published guidelines (51). Unless otherwise indicated, for assays involving serum starvation, serum concentration was reduced to 0.2% overnight for HeLa cells and 0% for Lx2 cells. Whole-cell lysates were prepared after washing cells with PBS before resuspending cells in lysis buffer [20 mM Hepes, pH 7.2, 5 mM Mg acetate, 125 mM K-acetate, 0.4% Triton X-100, 1 mM DTT, supplemented with sodium orthovanadate (500 µM), phosphatase (Sigma) and protease (Roche) inhibitor mixtures], and boiling them in sample buffer.

For immunoblotting, protein samples were separated by SDS/PAGE and transferred to PVDF membranes (Millipore). Membranes were blocked with PBS supplemented with 5% nonfat milk (or with 5% BSA when probing for phosphorylated proteins) before incubation with primary antibodies. Infrared imaging with two-color detection and quantification were performed using a Li-Cor Odyssey imaging system (50, 52, 53). Primary antibodies were diluted as follows: anti-His 1:1,000; anti-GIV/Girdin (T-13) 1:500; antiphospho EGFR 1068 (1:1000); anti-phospho-Akt (Ser473) 1:250; anti-Akt 1:500; anti-Gαi3 1:333; anti-pan-GP 1:250; anti-α tubulin 1: 2,000. All Odyssey images were processed using Image J software (NIH) and assembled for presentation using Photoshop and Illustrator software (Adobe).

Lentivirus Production and Generation of HeLa Cells Stably Depleted of GIV.

The lentiviral packaging plasmid psPAX2 and envelope plasmid pMD2G were obtained from University of California (San Diego). To prepare virus stocks, 293T cells were cotransfected with shRNA LUC (luciferase) or GIV constructs (~10.5 µg), together with pCMV-VSVG envelope (3.8 µg), pMDLgp-RRE (7 µg) and pRSV-Rev (2.6 µg) constructs, using Calcium Phosphate transfection mix [2 M CaCl2, 2 Å~Hepes Buffered Saline: 280 mM NaCl, 50 mM Hepes, 1.5 mM Na2HPO4, pH 7.05]. The media was changed after 24 h, and virus-containing medium was collected after 36-48 h. The viral stocks were centrifuged and filtered through a 0.45-µm filter to remove any nonadherent 293T cells. Young passages of HeLa cells were infected with a mixture of 0.5 mL of shRNA lentivirus-containing medium and 0.5 mL DMEM with 10% FBS. The medium was changed 24 h postinfection and replaced with fresh DMEM. Selection of stable cells was initiated at 48 h with 2.5 µg/mL Puromycin (Invitrogen). Pooled stable cells were subsequently maintained in complete media supplemented with 2.5 µg/mL Puromycin. AdCre, Crerecombinase expressing adenovirus (commercially obtained from the Transfer Vector Core at the University of Iowa) was used to trigger GIV depletion 48-72 h before using the cells for experiments.

Immunofluorescence.

HeLa cell lines were fixed at room temperature with 3% paraformaldehyde for 20-25 min, permeabilized (0.2% Triton X-100) for 45 min and incubated for 1 h each with primary and then secondary antibodies as described (7). Dilutions of antibodies and reagents were as follows: His (1:500); Phalloidin (1:1,000); DAPI (1: 2,000); secondary goat anti-rabbit (594) and goat anti-mouse (488) Alexa-conjugated antibodies (1:500). Coverslips were mounted with ProLong Gold (Life Technologies). Cells were imaged on a Leica SPE confocal microscope using a 63× oil objective using 488, 561, and 405 laser lines for excitation. Images were scanned using a line-average of 3. All images were processed using ImageJ software and assembled into figure panels using Photoshop and Illustrator (Adobe).

In Vitro GST Pulldown Assays.

Purified GST-Gαi3 or GST alone (5 µg) were immobilized on glutathione-Sepharose beads and incubated with binding buffer [50 mM Tris-HCl (pH 7.4), 100 mM NaCl, 0.4% (vol:vol) Nonidet P-40, 10 mM MgCl2, 5 mM EDTA, 30 µM GDP, 2 mM DTT, protease inhibitor mixture] for 90 min at room temperature as described (49, 50, 52, 54). TAT-GIV-CT (amino acids 1,660-1,870) proteins (3 µg) were added to each tube, and binding reactions were carried out for 4 h at 4° C. with constant tumbling. Beads were washed (four times) with 1 mL of wash buffer [4.3 mM Na2HPO4, 1.4 mM KH2PO4 (pH 7.4), 137 mM NaCl, 2.7 mM KCl, 0.1% (vol:vol) Tween 20, 10 mM MgCl2, 5 mM EDTA, 30 µM GDP, 2 mM DTT] and reduced in Laemmli's sample buffer at 37° C. Immunoblot analysis was performed by infrared imaging following the manufacturer's protocols using an Odyssey imaging system (Li-Cor Biosciences).

Fret Studies.

HeLa cells stably depleted of GIV by shRNA were grown to 60-70% confluence in sterile 35 mm MatTek glass bottom dishes. One microgram each of various donor and acceptor plasmid constructs were transfected with Trans-IT-LT1 transfection reagent (Minis Bio LLC) using manufacturer's protocol. Cells were starved overnight in serum-free DMEM (Gibco), transduced the following morning with TAT proteins for 30 min, washed with PBS and subsequently the media was switched to DMEM without phenol red before live cell imaging. EGF stimulation was carried out ~4 h after TAT transduction. Fluorescence microscopy studies were conducted on single cells in mesoscopic regime to avoid inhomogeneities from samples as previously rationalized by Midde et al. (55-57). Olympus FV1000 inverted confocal laser scanning microscope was used for live cell FRET imaging (UCSD-Neuroscience core facility). The microscope is stabilized on a vibration proof platform, caged in temperature controlled (37° C.) and CO2 (5%) supplemented chamber. A 60×1.49 N. An oil immersed objective designed to minimize chromatic aberration and enhance resolution for 405-605 nm imaging was used. Olympus Fluoview inbuilt software was used for data acquisition through the method of sensitized emission. A 405 nm laser diode was used to excite ECFP and 515 nm Argon-ion laser was used to excite EYFP. The bandwidth of spectral emission was adjusted through grating to minimize bleed through. Enhanced CFP emission was collected from 425 to 500 nm and EYFP emission was collected through 535-600 nm and passed through a 50 nm confocal pinhole before being sent to photomultiplier tube to reject out of plane focused light. Every field of view is imaged sequentially through ECFPex/ECFPem, ECFPex/EYFPem and EYFPex/EYFPem (3 excitation and emission combinations) and saved as donor, transfer and acceptor image files through an inbuilt wizard.

To obtain the FRET images and efficiency of energy transfer values a RiFRET plugin in Image J software was used (58). FRET images were obtained by pixel-by-pixel ratiometric intensity method and efficiency of transfer was calculated by the ratio of intensity in transfer channel to the quenched (corrected) intensity in the donor channel. Cells transfected with CFP and YFP alone were imaged under all three previously mentioned excitation and emission combinations and are used to correct for cross-talk. Furthermore, untransfected cells and a field of view without cells were imaged to correct for background, autofluorescence and light scattering. Cells chosen for imaging were ensured for identical expression of donor and acceptor probes by the photons collected in individual channels.

Cell Migration and Invasion Assays.

Scratch-wound assays were done as described (49). Briefly, monolayer cultures (100% confluent) of HeLa cells were incubated first in a 0.2% serum media over night. The following morning, monolayers of HeLa cells were first transduced with TAT peptides for 30 min, then washed three times with PBS and placed again in a 0.2% serum media for 1 h 30 min before scratch-wounding. The wounds were created using a 20 µL pipette tip. Transduction with TAT peptides was repeated at 12 h into the wound healing assay (a total of two times). Healing wounds were monitored by phase-contrast microscopy over the next 24 h and serially photographed using a Canon digital SLR camera. To quantify cell migration (expressed as percent of wound closure) the acquired images were analyzed using Image J software to measure open wound area. Results were expressed as % closure by calculating the difference between the wound area at 0 h, 12 h and that at 24 h divided by the area at 0 h×100. Invasion assays were performed using Corning Transwell plates according to the manufacturer's protocol.

Briefly, after a serum starvation overnight, MDA MB231 cells were first transduced with TAT peptides for 30 min as above. Transduced cells were trypsinized, counted, and placed in a Corning transwell permeable support coated with Cultrex Basement Membrane Extract ($7 \times 10^4$ cells per well). Media without FBS but containing EGF ligand (50 nM) was placed within the bottom chamber of each well to trigger directional 3D invasion. As done in the 2D migration assays, transduction with TAT peptides was repeated one more time ~10-12 h into the assay (total of two times). At 22-24 h, a Q-tip was used to meticulously remove all cells from the surface of the permeable membrane facing the upper chamber. Cells that had successfully invaded to the side of the permeable membrane facing the bottom chamber were visualized by staining the membrane with crystal violet. To quantify cell invasion (expressed as number of invasive cells/high power field) ~10-12 random fields per membrane insert per condition were analyzed for number of crystal violet stained cells. Assays were repeated four times.

RNA Isolation and Quantitative PCR.

For measurement of collagen and αSMA mRNA levels in Lx2 HSCs we followed the protocols exactly as before (59). Briefly, total RNA was isolated using an RNeasy kit (QIAGEN) as per the manufacturer's protocol. First-strand cDNA was synthesized using SuperScript II reverse transcriptase (Invitrogen), followed by ribonuclease H treatment (Invitrogen) before performing quantitative realtime PCR. Reactions omitting reverse transcriptase were performed in each experiment as negative controls. Reactions were then run on a real-time PCR system (ABI StepOnePlus; Applied Biosystems). Gene expression was detected with SYBR green (Invitrogen), and relative gene expression was determined by normalizing to GAPDH using the $\Delta\Delta_T$ method. The sequences of primers used in this work are identical to what were used previously (59).

Dermal Wound Healing in Mice.

Under general anesthesia, two 6-mm diameter punch biopsy wounds were created on the shaved dorsal surface of 8 wk old female C56BL/6 wild-type mice under sterile conditions. Wounds were then treated with 15 μg (~500 pmol) of TAT proteins every 24 h for 8 d after injury, and photographed every 48 h over that period, and wound area was manually traced by placing a transparent film over the wound and tracing the outline with a permanent marker. To measure the wound area, the edges of the dermis were determined as the wound edge. This method has been shown to be superior in estimating healing rates of irregular wounds (60). The tracing was then scanned and measured using an image analysis program (NIH Image J Software). Five mice, each with 2 wounds (a total of 10 wounds) were studied in each treatment arm, and their rate of closure was analyzed. These studies were carried out in a blinded manner such that aliquots of purified TAT proteins were prepared and color coded before their arrival at the animal facility. Consequently, the personnel who performed dermal punch biopsies, daily treatment with TAT proteins, photography and measurement of wound area was blinded to the identity of the compound. The study protocol (FIG. 4B) included standard wound care as per IACUC guidelines.

TAT-Protein Expression and Purification.

Cloning of TAT-GIV-CT was carried out by amplifying a short flexible linker (see FIG. 1A) and the stretch of human GIV-CT (aa 1660-1870) en bloc from CFP-GIV-CT (25) and inserting it between Ncol/Kpn1 of pTAT-HA. TAT-GIV-CT-FA mutant was generated using QuickChange II (Stratagene) and specific primers (sequence available upon request) following the manufacturer's instructions. TAT-constructs were expressed using BL21(DE3)-pLysS (Invitrogen) and Terrific Broth (BioPioneer) supplemented with additives as per auto-induction protocols outlined by Studier F (39). Briefly, cultures of bacteria were grown at 300 rpm at 37° C. for 5 h, then at 25° C. overnight. Cells were lysed in 10 ml of buffer [20 mM Tris, 10 mM Imidazole, 400 mM NaCl, 1% (v:v) Sarkosyl, 1% (v:v) Triton X-100, 2 mM DTT, 2 mM Na3oV4 and protease inhibitor mixture (Roche Diagnostics) (pH 7.4)], sonicated (3×30 s), cleared at 12,000×g for 20 min at 4° C. and affinity-purified on Ni-NTA agarose resin (Quiagen) (4 h at 4° C.). Proteins were eluted in elution buffer [20 mM Tris, 300 mM Imidazole, 400 mM NaCl, pH 7.4], dialyzed overnight against TBS containing 400 mM NaCl and stored at −80° C.

TAT Protein Transduction.

For TAT-protein transduction, cells were incubated with 400-800 nM of the TAT-proteins for 30 min at 37° C. prior to three washes with PBS and addition of fresh growth media. For analysis of EGF signaling, subconfluent monolayers of HeLa cells were treated with TAT proteins for 30 min, washed with PBS, and subsequently stimulated with EGF (50 nM) at 4 h after TAT transduction. For scratch-wound assays, HeLa monolayers were treated with TAT proteins before and at 12 h after wounding. For cancer cell invasion assays, highly invasive MDA MB 231 breast cancer cells were plated in 6-well dishes, treated with TAT-peptides for 30 min and subsequently lifted and placed in transwell chamber in the presence of serum-free media. For Lx2 myofibroblast activation assays, cells were first treated with TAT-proteins for 30 min, starved in serum-free media, and subsequently treated with 1.5 ng/ml TGF-β for 24 h. TAT-protein transduction was repeated every 8 h during the course of TGFβ stimulation (total 3 treatments). For assays involving insulin stimulation of TAT-treated L6 myotubes, such stimulation was carried out 90 min after transduction. In each case, whole cell lysates prepared from cells in duplicate wells were analyzed for signaling pathways and TAT-protein uptake by immunoblotting.

Scratch-Wounding and Migration Index.

Scratch-wound assays were done as described previously (13). Briefly, monolayer cultures (100% confluent) of HeLa cells were incubated first in a 0.2% serum media over night. The following morning, monolayers of HeLa cells were first transduced with TAT peptides for 30 min, then washed 3 times with PBS and placed again in a 0.2% serum media for 1 h 30 min before scratch-wounding. Transduction with TAT peptides was repeated at 12 h into the wound healing assay (a total of 2 times). Healing wounds were monitored by phase-contrast microscopy over the next 24 h and migration index was quantified (expressed as % wound closure) by measuring the wounded area using Image J software.

Tumor Cell Invasion Assays:

Invasion assays were performed using Corning® Transwell plates according to the manufacturer's protocol. Transduced cells were trypsinized, counted and placed in a Corning transwell permeable support coated with Cultrex®

Basement Membrane Extract ($7\times10^4$ cells/well). Media without FBS but containing EGF ligand (50 nM) was placed within the bottom chamber of each well to trigger directional 3D invasion. transduction with TAT peptides was repeated one more time ~10-12 h into the assay (total of 2 times). Cells that had successfully invaded to the side of the permeable membrane facing the bottom chamber were visualized by staining the membrane with crystal violet. Cell invasion (expressed as number of invasive cells/high power field) was quantified by analyzing ~10-12 random fields/membrane insert/condition for number of crystal violet stained cells.

Data Analysis and Other Methods.

All experiments were repeated at least three times, and results were presented either as one representative experiment or as average±SD or S.E.M. Statistical significance was assessed with the Student's t test. *$p<0.05$;  $p<0.01$; * $p<0.001$; **** $p<0.0001$. Protein structure analysis and visualization were performed using ICM Browser Pro software (Molsoft Inc).

Results and Discussion

Generation of Cell-Permeable Peptides Comprised of Key Modules Derived from GIV.

Figures 1A, 1B, 1C, 1D:
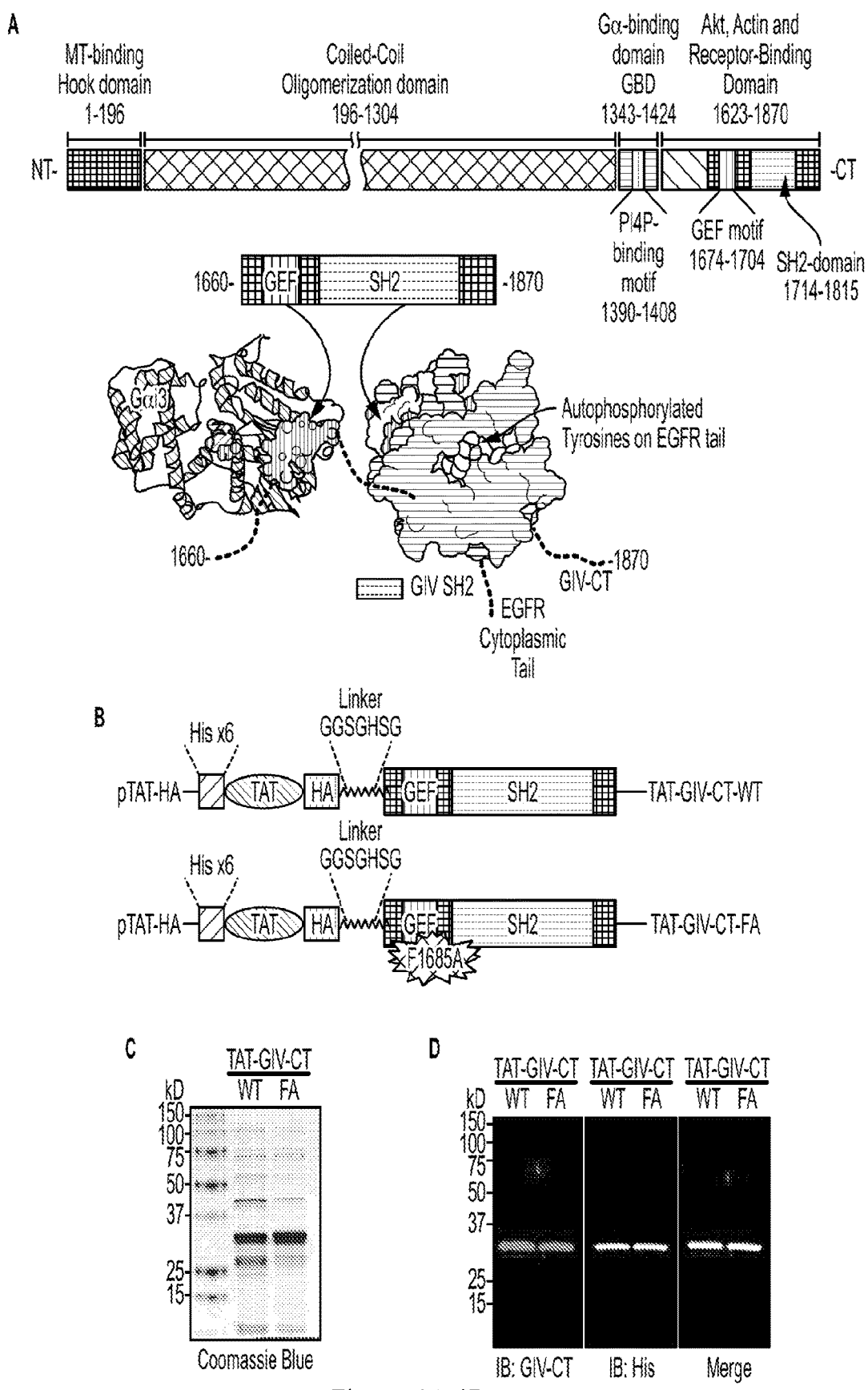
FIGS. 1A-1D. Design and purification of cell-permeable TAT-GIV CT peptides.

To generate the cell-permeable peptides, a validated strategy of building the multi-modular fluorescent GIV biosensors was followed (25). Because TAT-tags provide a reliable means for direct protein transduction into the cell, without inducing toxicity or cell death (26-28), the cell-permeable peptides were generated by fusing the C-terminus of GIV (1660-1870 residues) at its N-terminus with the TAT peptide transduction domain (TAT-PTD) (FIG. 1B). A previously described GEF-deficient F1685A mutant (7), henceforth referred to as FA (TAT-GIV-CT-FA) was created to selectively disrupt the GIV-Gαi interaction. A linker was placed between TAT and GIV to allow for flexibility. The constructs also featured a hexa-Histidine (6× His) tag to allow for affinity purification and a Hemagglutinin (HA) tag to allow detection in cells. The rationale for the design of these peptides is multi-factorial: 1) a complete phylogenetic analysis of GIV (17) has revealed that this stretch of GIV's C-terminus could be functionally autonomous because it evolved independently of its N-terminus (in fish), and both N- and C-termini fused into full length GIV only in birds; 2) the C-terminus contains the GEF and SH2-like domains (FIG. 1B), representing the cross-road between GPCR/G and RTK signaling pathways; 3) the C-terminus of GIV also contains the two critical tyrosines (Y1764 and Y1798) that serve as docking sites for p85α(PI3K) (29); 4) the coexistence of those tyrosines, the GEF motif, and the SH2-like domain is restricted only to the most complex of eukaryotes, i.e., mammals, and is highly conserved (~99%) (17, 29); 5) biochemical and functional assays (9, 25) have convincingly demonstrated that the C-terminus is the most critical domain that is necessary and sufficient for GIV to carry out its functions during signal transduction downstream of RTKs; and finally, 6) biophysical studies (25) have revealed that fluorescent GIV-CT biosensors are effective tools for visualization and manipulation of the fundamental function of GIV in signal transduction, i.e., enabling dynamic association of Gαi with RTKs and non-canonical transactivation of G proteins in cells responding to growth factors. We expressed and purified (~95-99% purity) the TAT-GIV-CT peptides and confirmed that they were expressed as proteins of expected size by immunoblotting (FIG. 1C, D). These recombinant peptides have the minimal modules that allow these peptides to induce macropinocytosis and facilitate endosomal escape in order to enter cytoplasm, and to operate autonomously and carry out most functions that have been previously attributed to the extensively characterized fluorescent GIV-CT biosensors (25) and to full length GIV [reviewed in (17)].

Cell-Permeable GIV-CT Peptides are Effective in Exogenous Modulation of Gi and EGFR Signaling.

Figures 2A, 2B, 2C, 2D, 2E, 2F:
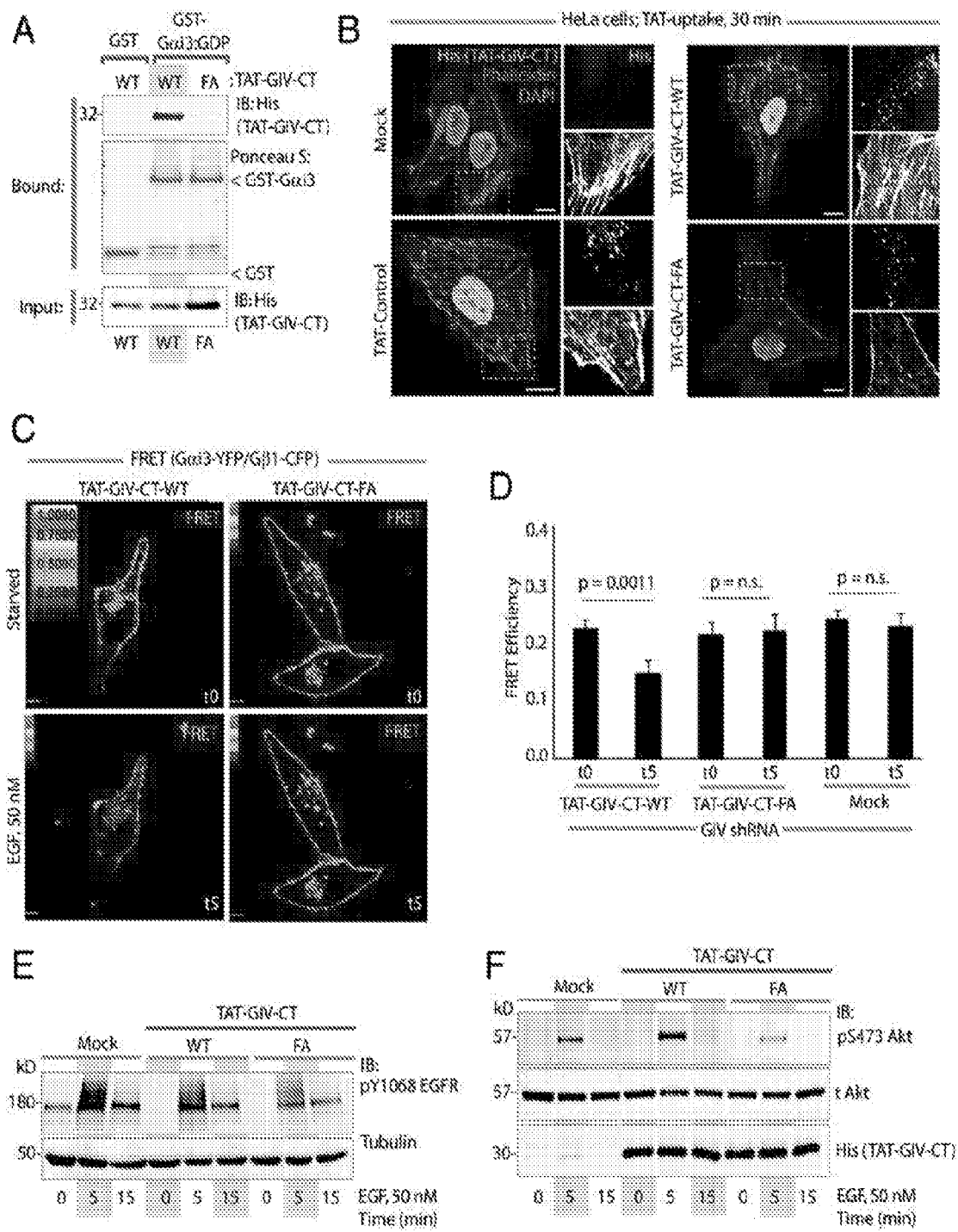
FIGS. 2A-2F. Cell-permeable TAT-GIV-CT peptides can bind and activate Gi, remodel cytoskeleton and enhance EGF signaling.
Figure 6:
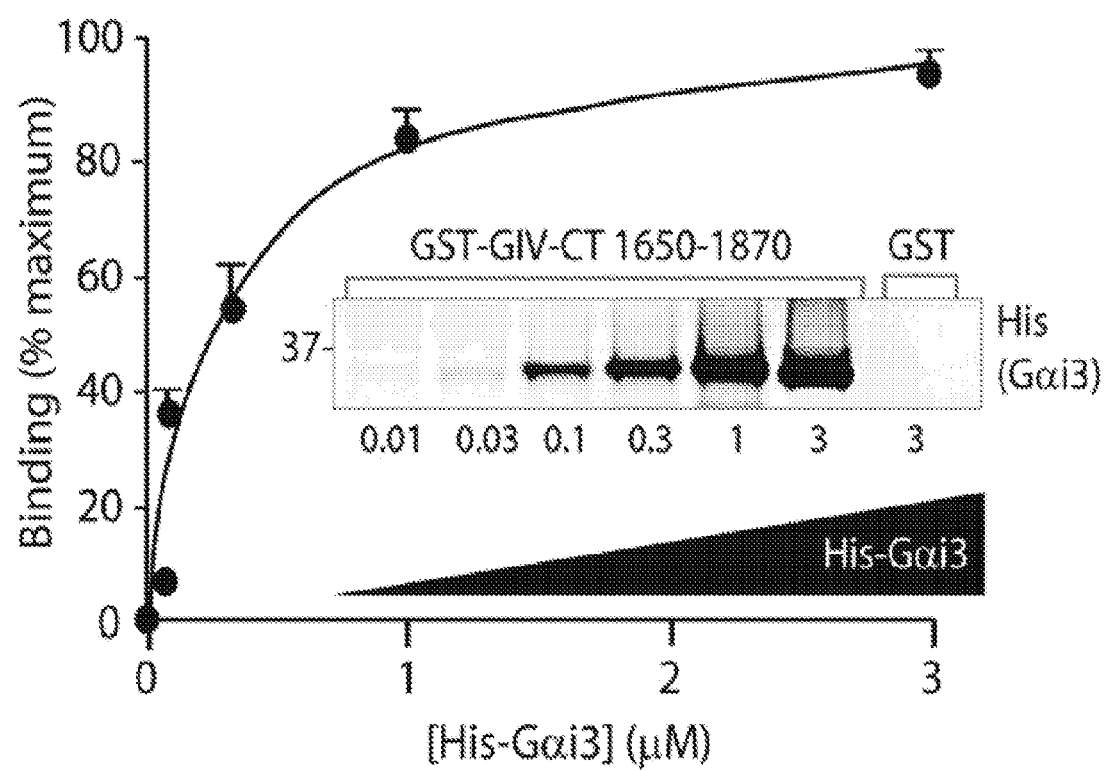
FIG. 6. GIV binds Gαi3 with submicromolar affinities. (Inset) Purified GST-GIV-CT (amino acids 1660-1870, containing the GBA motif, and the exact boundaries used in TAT-GIV-CT constructs) immobilized on glutathione-agarose beads was incubated with increasing amounts (0.01-3 µM) of purified His-Gαi3 (GDP-loaded) and binding analyzed by immunoblotting using anti-His mAb (Gαi3). No binding to GST alone was detected at the highest His-Gαi3 concentration tested. (Graph) Gαi3 binding was quantified by measuring band intensities and data fitted to a single-site binding hyperbola to determine the equilibrium dissociation constants (Kd=0.24±0.03 µM). Mean±SEM of three independent experiments.

Several biochemical and functional assays were carried out to determine if TAT-GIV-CT peptides are indeed functional. First, the ability of TAT-GIV-CT peptides binding to Gαi was assessed in vitro. Consistent with the known binding properties of GEFs, TAT-GIV-CT-WT bound inactive (i.e., GDP-loaded GST-Gαi3) (FIG. 2A). As anticipated, the GEF-deficient TAT-GIV-CT-FA peptide did not bind Gαi3 (FIG. 2A). Using a GST-tagged GIV-CT peptide (identical length as TAT-GIV-CT peptide) It was confirmed that Gαi3 binds GIV with submicromolar affinity [equilibrium dissociation constant (Kd)=0.24±0.03 µM] (FIG. 6).

To analyze the effects of TAT-GIV-CT peptide on cells, cellular uptake of these peptides was first tested in HeLa cells. HeLa cells were chosen in this study because this is a well-accepted model system and has been extensively used to characterize the role of GIV in our prior work (16, 18, 29, 30). Incubation of HeLa cells with 400-800 nM TAT-GIV-CT peptides for 30 min resulted in efficient uptake (~90-100% cells by immunofluorescence) with no observed toxicity (FIG. 2B). Consistent with the central role of GIV's GEF function in actin remodeling (7), transduction of TAT-GIV-CT-WT triggered actin remodeling (as determined by the abundance of actin stress fibers; FIG. 2B). By contrast, transduction of the TAT-GIV-CT-FA mutant suppressed stress fibers, and instead enhanced the thickness of cortical actin, identical to the observed pattern of actin cytoskeleton endogenously modulated by full length GIV-FA mutant (7).

Figure 7:
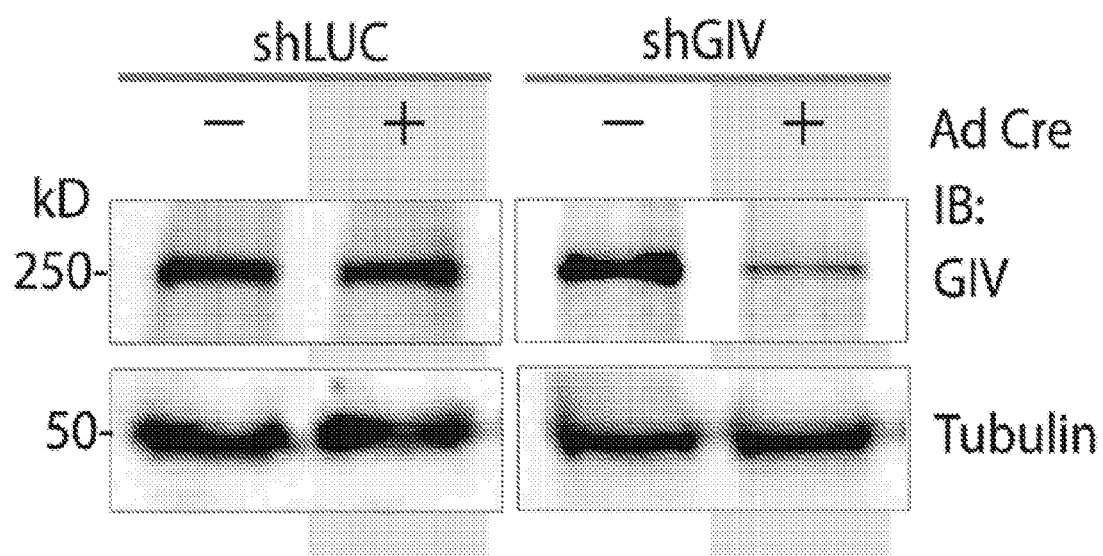
FIG. 7. Confirmation of Cre-inducible depletion of GIV in HeLa cells. Whole cell lysates of control (shLUC; targeting luciferase) or GIV-depleted (shGIV) HeLa cells were prepared with (+) or without (−) treatment with Cre recombinase adenovirus. Equal aliquots of lysates were analyzed for GIV and α-tubulin by immunoblotting (IB). Quantitative immunoblotting using LiCOR dual color Odyssey Imager confirmed ~80-85% depletion of GIV.

Next, it was determined if TAT-GIV-CT peptides can modulate Gi and epidermal growth factor (EGF) signaling in HeLa cells. Responses to EGF were studied because EGF is the ligand for EGF receptor (EGFR), the prototype member of the RTK superfamily and has been extensively used to study the cellular functions of GIV (8, 9, 25), and because the structural basis for GIV's interaction with EGFR is most well understood (24). To determine if TAT-GIV-CT peptides can exogenously modulate Gi activation downstream of EGFR, a previously validated assay was used in which activation of Gi is monitored by dissociation of fluorescently tagged Gαi and Gβγ subunits with a resultant loss of fluorescence resonance energy transfer (FRET) (31-33). To ensure that the observed changes in FRET are not due to a dominant negative effect of TAT-GIV-CT transduction and to minimize any potential interference posed by endogenous full length GIV, these assays were carried out in HeLa cells depleted of endogenous GIV by shRNA (FIG. 7).

Figures 8A, 8B:
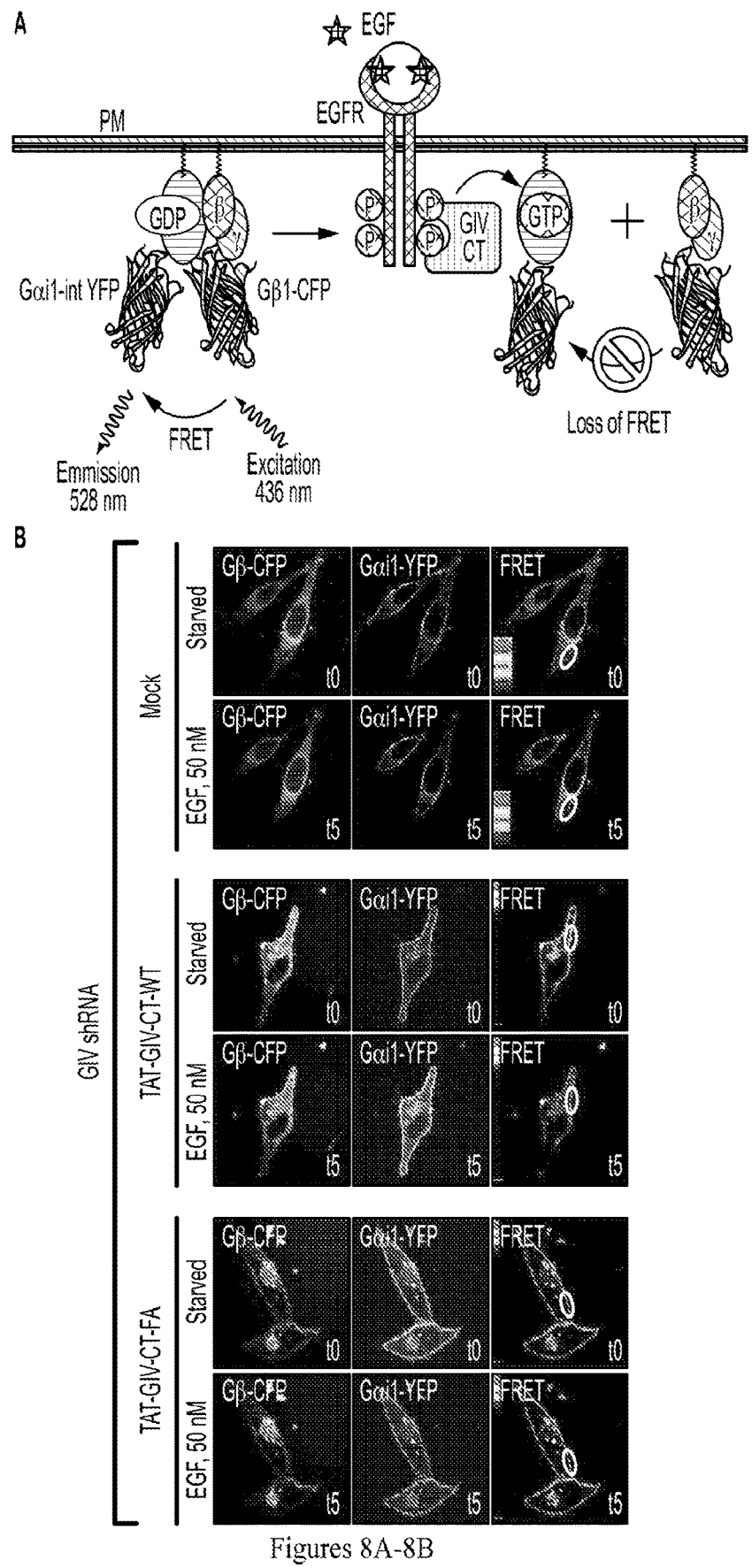
FIGS. 8A-8B. TAT-GIV-CT-WT, but not FA is sufficient to trigger dissociation of trimeric Gi at the PM after EGF stimulation. (A) Schematic for the Gαi1-intYFP and Gβ1-CFP constructs used as paired FRET probes in B. FRET indicates inactive heterotrimers, whereas a loss of FRET indicates dissociation of the trimer during activation of Gi. (B) GIV-depleted HeLa cells cotransfected with Gαi1-intYFP and Gβ1-CFP were stimulated with EGF. Representative freeze-frame YFP, CFP, and FRET images at t0 and t5 are shown (when maximal dissociation at the PM was observed; see FIGS. 2C and 2D). A representative ROI used for analysis of FRET efficiency at the PM is shown (red oval).

It was found that, when GIV-depleted HeLa cells co-expressing Gαi1-YFP (internal tag), CFP-Gβ$_i$ (N-terminal tag) and Gγ$_2$ (untagged) were stimulated with EGF, no significant loss of FRET was observed, i.e., Gi heterotrimer did not dissociate into Gαi-YFP and CFP-Gβγ subunits at the PM within 5 min (FIG. 2D; FIGS. 8A & 8B), indicating that EGF fails to trigger Gi activation in the absence of GIV. When these cells transduced with TAT-GIV-CT-WT a significant loss of FRET was observed (from 0.22±0.04 to 0.15±0.07; p=0.0011) in response to EGF. No similar loss of FRET was observed when cells were transduced with TAT-GIV-CT-FA peptides (FIGS. 2C-2D), indicating that Gi heterotrimers remained intact at the PM regardless of EGF stimulation, and that Gαi remained inactive. These results demonstrate that TAT-GIV-CT peptides are effective in exogenous modulation of Gi activity downstream of EGFR, i.e., they can bind and activate Gαi and release Gβγ in cells in a GEF dependent manner as previously demonstrated for full length GIV (7) and fluorescent GIV-CT biosensors (25). These findings also suggest that the TAT-GIV-CT-WT peptides bind Gαi in cells with high affinity that is sufficient to overcome the high affinity that Gβγ-heterodimers have for Gαi-GDP (Dissociation constant=~3-10 nM (34)).

Consistent with the central role of GIV's GEF function in the enhancement of EGFR autophosphorylation (9, 30) and PI3K-Akt signals downstream (7, 29), transduction with TAT-GIV-CT-FA inhibited receptor autophoshorylation (as determined by phosphorylation at Y1068 and Y1173 on EGFR tail (FIG. 2E) and Akt signaling (as determined by the extent of phosphorylation of Akt at Ser 473; FIG. 2F). These findings demonstrate that the TAT-GIV-CT biosensors can exogenously modulate EGF signaling characteristic of full length GIV (7, 9, 29, 30) and fluorescent GIV-CT biosensors (25).

Taken together, it was concluded that TAT-GIV-CT peptides represent the smallest, functionally autonomous units that effectively combine the cell-permeant properties of TAT to exogenously engineer many key signaling properties of GIV in cells.

Cell-Permeable GIV-CT Proteins Allow Manipulation of a Diverse Array of Complex GIV-Dependent Cellular Processes.

Figures 3A, 3B, 3C, 3D, 3E, 3F, 3G, 3H, 3I, 3J:
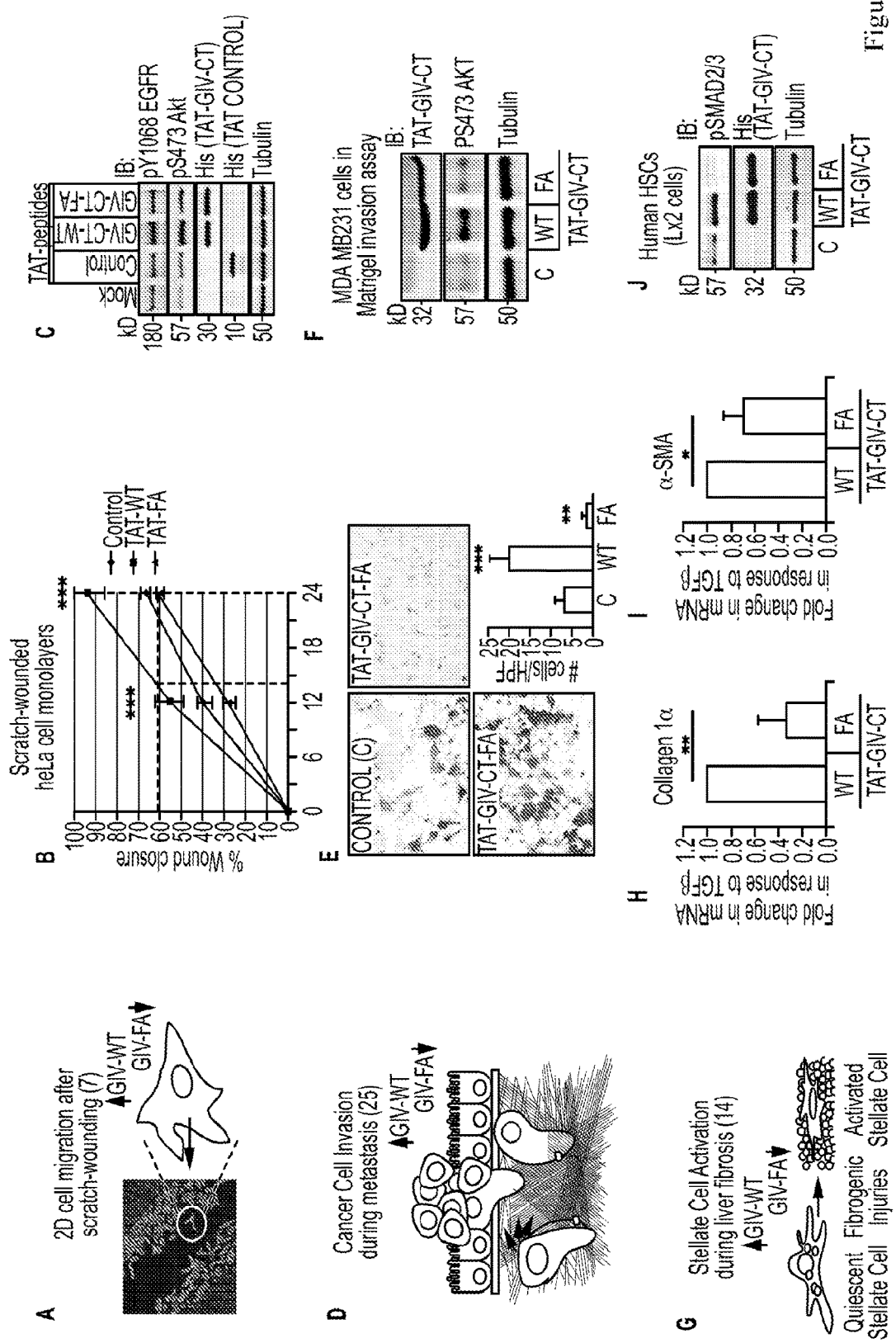
FIGS. 3A-3J. TAT-GIV-CT proteins can effectively manipulate a diverse array of GIV-dependent pathophysiologic processes.

Next, it was determined if TAT-GIV-CT peptides can exogenously modulate complex, multi-receptor driven cellular phenotypes previously attributed to full length GIV, e.g., cell migration (8, 9) (FIGS. 3A-C) and tumor cell invasion through basement membrane during cancer metastasis (10) (FIGS. 3D-F). To determine if TAT-GIV-CT peptides affect 2D-cell migration, scratch-wound assays weew carried out on confluent monolayers of HeLa cells transduced with TAT proteins (FIG. 3A). It was found that compared to mock treatment, TAT-GIV-CT-WT peptides enhanced 2D-migration and wound closure more efficiently, whereas the FA mutant peptides delayed wound closure (FIG. 3B). Consistent with the enhancement or delay in wound closure, EGFR autophosphorylation and Akt activation were enhanced in WT but not in FA-transduced cells (FIG. 3C). These results demonstrate that TAT-GIV-CT peptides are capable of exogenously modulating 2D-cell migration, and the key PI3K-Akt signaling pathway that drives such migration.

Next, the effect of TAT-GIV-CT peptides on cancer cell invasion through polypropylene membranes that are pre-coated with basement membrane protein was analyzed in a 3-D Transwell® assay (FIG. 3D-F). The highly invasive MDA MB231 triple negative breast cancer cell lines were used because they are not only known to express GIV at very high levels (8, 9, 18, 23) but also require GIV for metastatic progression in murine models (10) (FIG. 3D). Invasion of MDA MB231 cells through basement membrane matrix in response to an EGF gradient was significantly enhanced when cells were pre-treated with TAT-GIV-CT-WT peptides compared to cells transduced with TAT-control peptides (FIG. 3E, F). By contrast, invasion was virtually abolished by the TAT-GIV-CT-FA mutant peptide. Taken together, these findings indicate that TAT-GIV-CT-WT peptide is sufficient to enhance both epithelial cell migration in 2D after wounding and tumor cell invasion through the basement membrane matrix in 3D, and that peptides that lack a functionally intact GEF motif (i.e., FA) can effectively inhibit both processes.

Next, it was determined if the cell-permeable GIV peptides can modulate another recently defined function of GIV, i.e., activation of myofibroblasts and collagen synthesis in response to chronic injuries (14) (FIG. 3G-J). Using myofibroblasts of the liver (i.e., human hepatic stellate cells; HSCs) as a model system, it showed that GIV's C-terminus serves as a central hub within the signaling network initiated by TGFβR, PDGFR and other diverse classes of fibrogenic receptors. GIV triggers HSC activation by skewing the signaling network in favor of fibrosis, i.e., enhances the profibrotic (PI3K-Akt-FoxO1 and TGFβ-SMAD) and inhibits the anti-fibrotic (cAMP-PKA-pCREB) pathways, all via activation of Gαi (FIG. 3G). To determine if HSC activation in response to TGFβ can be suppressed by GEF-deficient GIV-CT peptides, it was found that compared to control cultured human HSCs (Lx2 cells) and HSCs transduced with TAT-GIV-CT-WT, transduction with TAT-GIV-CT-FA suppressed collagen production by ~70% (FIG. 3H) and reduced HSC activation by ~30%, as determined by the expression of α-SMA (FIG. 3I). These changes in fibrogenic phenotypes were accompanied by an underlying suppression of the profibrogenic TGFβ-SMAD cascade, as determined by phosphorylation of SMAD2/3 (FIG. 3J). Thus, it is concluded that cell-permeable GIV-CT-FA peptides that lack a functional GEF motif are sufficient for inhibition of TGFβ-triggered activation of HSCs. These findings also demonstrate that TAT-GIV-CT peptides can effectively modulate multi-receptor driven Gi signaling in HSCs.

Taken together, it is concluded that cell-permeable GIV-CT peptides represent a versatile strategy to modulate various growth factor responses, in diverse cell types, to modulate a wide array of cellular processes driven by GIV-GEF.

Cell-Permeable GIV-CT-WT Peptides Accelerate Wound Healing in Mice.

Figures 4A, 4B, 4C, 4D:
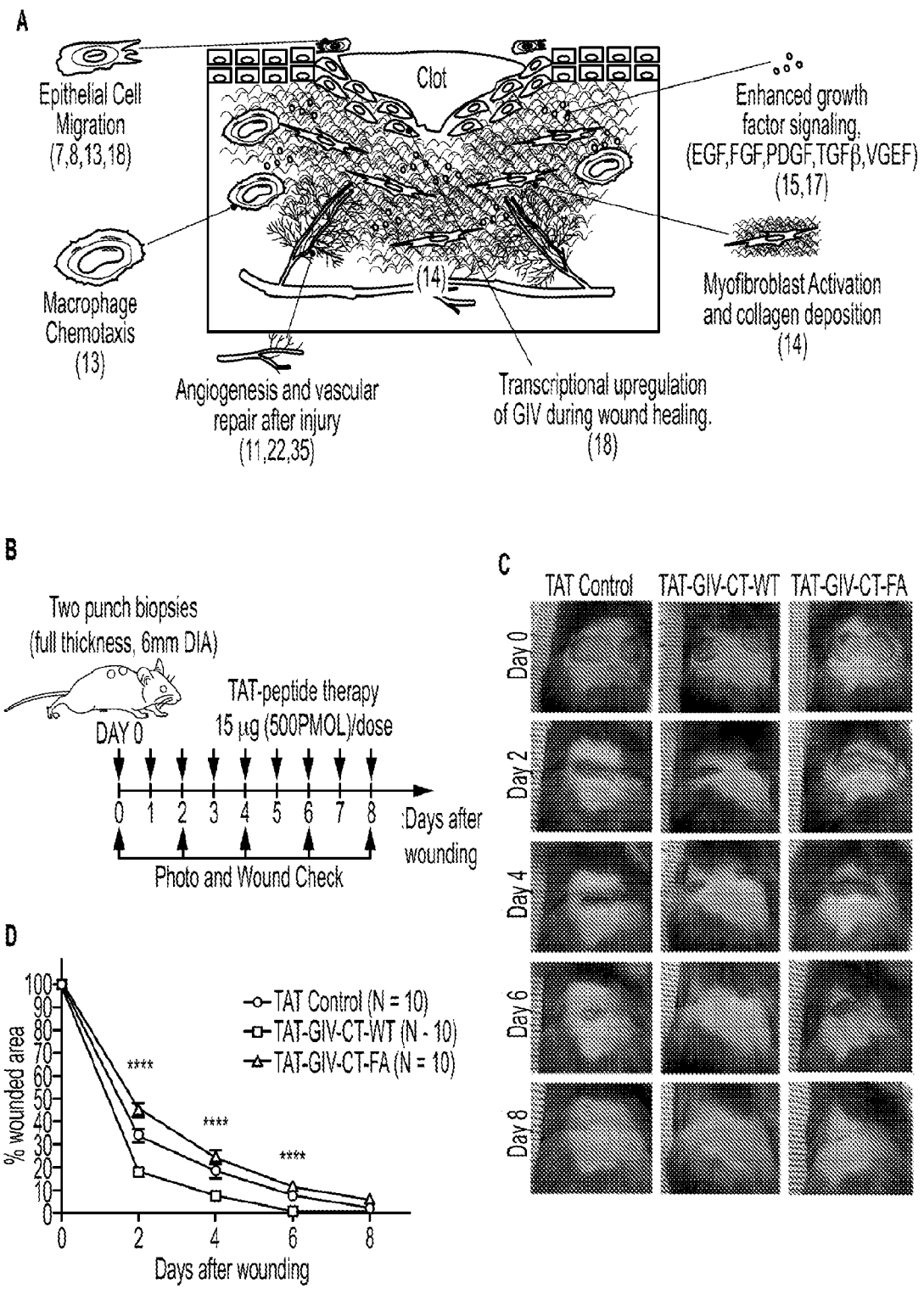
FIGS. 4A-4D. Topical application of cell-permeable GIV-CT-WT peptides accelerate dermal wound healing.

The therapeutic potential of TAT-GIV-CT peptides was analyzed in vivo in the modulation of the complex, multi-receptor driven process of dermal wound-healing in mice. The rationale to study wound healing was multi-factorial. First, wound healing is a multi-receptor driven process that involves coordination of diverse cell populations and cellular processes. Second, the ubiquitous expression of GIV in all cell types involved in healing, the transcriptional upregulation of GIV after wounding, and the role GIV-GEF in many of those cells/processes has been well documented (7, 8, 11, 13, 14, 17, 18, 22, 35) (FIG. 4A). Third, a variety of growth factors and their corresponding RTKs trigger wound closure, and GIV has been shown to bind and modulate signal transduction downstream of many of those RTKs (see FIG. 4A). Finally, wound healing remains a challenging clinical problem, and the development of new therapeutic approaches and technologies is critical.

Of the many pathophysiologic processes modulated by TAT-GIV-CT (FIG. 3), its topical application on wounds is the most feasible therapeutic application. Full-thickness 6 mm punch biopsy wounds were made on the dorsum of mice, 500 pmol TAT-GIV-CT (WT and FA) or TAT control peptides were used to treat these wounds daily, and their rates of healing were compared in blinded manner (FIG. 4B). Compared to TAT-treated controls, the treatment group exposed to TAT-GIV-CT-WT demonstrated accelerated wound healing (~2× the rate and a day earlier), whereas the group treated with the FA mutant demonstrated delayed wound healing (FIG. 4C-D). These findings demonstrate that topical application of TAT-GIV-CT peptides accelerate wound healing, and that the GEF motif is critical for this observed therapeutic effect. It is concluded that cell-permeable GIV-CT peptides retain their functionality in vivo, and that are capable of modulating complex multi-cellular pathophysiologic processes.

REFERENCES

1. Schlessinger J (2014) Receptor tyrosine kinases: Legacy of the first two decades. Cold Spring Harb Perspect Biol 6(3).
2. Gilman A G (1987) G proteins: Transducers of receptor-generated signals. Annu Rev. Biochem 56:615-649.
3. Daub H, Weiss F U, Wallasch C, Ullrich A (1996) Role of transactivation of the EGF receptor in signalling by G-protein-coupled receptors. Nature 379(6565):557-560.
4. Natarajan K, Berk B C (2006) Crosstalk coregulation mechanisms of G protein-coupled receptors and receptor tyrosine kinases. Methods Mol Biol 332:51-77.
5. Pierce K L, Luttrell L M, Lefkowitz R J (2001) New mechanisms in heptahelical receptor signaling to mitogen activated protein kinase cascades. Oncogene 20(13): 1532-1539.
6. Marty C, Ye R D (2010) Heterotrimeric G protein signaling outside the realm of seven transmembrane domain receptors. Mol Pharmacol 78(1):12-18.
7. Garcia-Marcos M, Ghosh P, Farquhar M G (2009) GIV is a nonreceptor GEF for G alpha i with a unique motif that regulates Akt signaling. Proc Natl Acad Sci USA 106(9): 3178-3183.
8. Enomoto A, et al. (2005) Akt/PKB regulates actin organization and cell motility via Girdin/APE. Dev Cell 9(3):389-402.
9. Ghosh P, et al. (2010) A Galphai-GIV molecular complex binds epidermal growth factor receptor and determines whether cells migrate or proliferate. Mol Biol Cell 21(13): 2338-2354.
10. Jiang P, et al. (2008) An actin-binding protein Girdin regulates the motility of breast cancer cells. Cancer Res 68(5):1310-1318.
11. Kitamura T, et al. (2008) Regulation of VEGF-mediated angiogenesis by the Akt/PKB substrate Girdin. Nat Cell Biol 10(3):329-337.
12. Garcia-Marcos M, Ear J, Farquhar M G, Ghosh P (2011) A GDI (AGS3) and a GEF (GIV) regulate autophagy by balancing G protein activity and growth factor signals. Mol Biol Cell 22(5):673-686.
13. Ghosh P, Garcia-Marcos M, Bornheimer S J, Farquhar M G (2008) Activation of Galphai3 triggers cell migration via regulation of GIV. J Cell Biol 182(2):381-393.
14. Lopez-Sanchez I, et al. (2014) GIV/Girdin is a central hub for profibrogenic signaling networks during liver fibrosis. Nat Commun 5:4451.
15. Garcia-Marcos M, Ghosh P, Farquhar M G (2015) GIV/Girdin transmits signals from multiple receptors by triggering trimeric G protein activation. J Biol Chem 290(11): 6697-6704.
16. Lopez-Sanchez I, et al. (2013) Protein kinase C-theta (PKCθ) phosphorylates and inhibits the guanine exchange factor, GIV/Girdin. Proc Natl Acad Sci USA 110(14): 5510-5515.
17. Ghosh P, Garcia-Marcos M, Farquhar M G (2011) GIV/Girdin is a rheostat that fine tunes growth factor signals during tumor progression. Cell Adhes Migr 5(3): 237-248.
18. Dunkel Y, et al. (2012) STAT3 protein up-regulates Gα-interacting vesicle-associated protein (GIV)/Girdin expression, and GIV enhances STAT3 activation in a positive feedback loop during wound healing and tumor invasion/metastasis. J Biol Chem 287(50):41667-41683.
19. Ohara K, et al. (2012) Involvement of Girdin in the determination of cell polarity during cell migration. PLoS ONE 7(5):e36681.
20. Natsume A, et al. (2012) Girdin maintains the stemness of glioblastoma stem cells. Oncogene 31(22):2715-2724.
21. Wang H M T, Taupin V, Eguchi A, Ghosh P, Farquhar M G (2014) GIV/Girdin links VEGF signaling to Akt survival signaling in podocytes independent of nephrin. J Am Soc Nephrol, in press.
22. Miyake H, et al. (2011) The actin-binding protein Girdin and its Akt-mediated phosphorylation regulate neointima formation after vascular injury. Circ Res 108(10): 1170-1179.
23. Garcia-Marcos M, et al. (2011) Expression of GIV/Girdin, a metastasis-related protein, predicts patient survival in colon cancer. FASEB J 25(2):590-599.
24. Lin C, et al. (2014) Structural basis for activation of trimeric Gi proteins by multiple growth factor receptors via GIV/Girdin. Mol Biol Cell 25(22):3654-3671.
25. Midde K K, et al. (2015) Multimodular biosensors reveal a novel platform for activation of G proteins by growth factor receptors. Proc Natl Acad Sci USA 112(9): E937-E946.
26. Becker-Hapak M, Dowdy S F (2003) Protein transduction: generation of full-length transducible proteins using the TAT system. Curr Protocols Cell Biol, Chapter 20: Unit 20 22.
27. van den Berg A, Dowdy S F (2011) Protein transduction domain delivery of therapeutic macromolecules. Curr Opin Biotechnol 22(6):888-893.
28. Wadia J S, Stan R V, Dowdy S F (2004) Transducible TAT-HA fusogenic peptide enhances escape of TAT-fusion proteins after lipid raft macropinocytosis. Nat Med 10(3): 310-315.
29. Lin C, et al. (2011) Tyrosine phosphorylation of the Gα-interacting protein GIV promotes activation of phosphoinositide 3-kinase during cell migration. Sci Signal 4(192):ra64.
30. Lin C, et al. (2014) Structural basis for activation of trimeric Gi proteins by multiple growth factor receptors via GIV/Girdin. Mol Biol Cell 25(22):3654-3671.
31. Janetopoulos C, Jin T, Devreotes P (2001) Receptor-mediated activation of heterotrimeric G-proteins in living cells. Science 291(5512):2408-2411.
32. Gibson S K, Gilman A G (2006) Gialpha and Gbeta subunits both define selectivity of G protein activation by alpha2-adrenergic receptors. Proc Natl Acad Sci USA 103(1): 212-217.
33. Bünemann M, Frank M, Lohse M J (2003) Gi protein activation in intact cells involves subunit rearrangement rather than dissociation. Proc Natl Acad Sci USA 100(26): 16077-16082.
34. Sarvazyan N A, Remmers A E, Neubig R R (1998) Determinants of gi1alpha and beta gamma binding. Measuring high affinity interactions in a lipid environment using flow cytometry. J Biol Chem 273 (14): 7934-7940.
35. Ito T, et al. (2013) Girdin and its phosphorylation dynamically regulate neonatal vascular development and pathological neovascularization in the retina. Am J Pathol 182(2):586-596.
36. Iiri T, Farfel Z, Bourne H R (1998) G-protein diseases furnish a model for the turn-on switch. Nature 394(6688): 35-38.
37. Siderovski D P, Willard F S (2005) The GAPs, GEFs, and GDIs of heterotrimeric G-protein alpha subunits. Int J Biol Sci 1(2):51-66.
38. Slep K C, et al. (2008) Molecular architecture of Galphao and the structural basis for RGS16-mediated deactivation. Proc Natl Acad Sci USA 105(17):6243-6248.

39. Studier F W (2005) Protein production by auto-induction in high density shaking cultures. Protein Expr Purif 41(1): 207-234.
40. Midde K, et al. (2013) Comparison of orientation and rotational motion of skeletal muscle cross-bridges containing phosphorylated and dephosphorylated myosin regulatory light chain. J Biol Chem 288(10):7012-7023.
41. Borejdo J, Rich R, Midde K (2012) Mesoscopic analysis of motion and conformation of cross-bridges. Biophys Rev 4(4):299-311.
42. Midde K, et al. (2014) Membrane topology of human presenilin-1 in SK-N-SH cells determined by fluorescence correlation spectroscopy and fluorescent energy transfer.
Cell Biochem Biophys 70(2):923-932.
43. Midde K K, et al. (2015) Multimodular biosensors reveal a novel platform for activation of G proteins by growth factor receptors. Proc Natl Acad Sci USA 112(9):E937-E946.
44. Garcia-Marcos M, Ghosh P, Farquhar M G (2009) GIV is a nonreceptor GEF for G alpha I with a unique motif that regulates Akt signaling. Proc Natl Acad Sci USA 106(9): 3178-3183.
45. Bünemann M, Frank M, Lohse M J (2003) Gi protein activation in intact cells involves subunit rearrangement rather than dissociation. Proc Natl Acad Sci USA 100(26): 16077-16082.
46. Gibson S K, Gilman A G (2006) Gialpha and Gbeta subunits both define selectivity of G protein activation by alpha2-adrenergic receptors. Proc Natl Acad Sci USA 103(1): 212-217.
47. Shah M, Baterina O Y, Jr, Taupin V, Farquhar M G (2013) ARH directs megalin to the endocytic recycling compartment to regulate its proteolysis and gene expression. J Cell Biol 202(1):113-127.
48. Studier F W (2005) Protein production by auto-induction in high density shaking cultures. Protein Expr Purif 41(1): 207-234.
49. Ghosh P, Garcia-Marcos M, Bornheimer S J, Farquhar M G (2008) Activation of Galphai3 triggers cell migration via regulation of GIV. J Cell Biol 182(2):381-393.
50. Ghosh P, et al. (2010) A Galphai-GIV molecular complex binds epidermal growth factor receptor and determines whether cells migrate or proliferate. Mol Biol Cell 21(13):2338-2354.
51. Xu L, et al. (2005) Human hepatic stellate cell lines, LX-1 and LX-2: new tools for analysis of hepatic fibrosis. Gut 54(1):142-151.
52. Garcia-Marcos M, et al. (2012) Functional characterization of the guanine nucleotide exchange factor (GEF) motif of GIV protein reveals a threshold effect in signaling. Proc Natl Acad Sci USA 109(6):1961-1966.
53. Garcia-Marcos M, Ghosh P, Ear J, Farquhar M G (2010) A structural determinant that renders G alpha(i) sensitive to activation by GIV/girdin is required to promote cell migration. J Biol Chem 285(17):12765-12777.
54. Lin C, et al. (2011) Tyrosine phosphorylation of the Gα-interacting protein GIV promotes activation of phosphoinositide 3-kinase during cell migration. Sci Signal 4(192):ra64.
55. Midde K, et al. (2013) Comparison of orientation and rotational motion of skeletal muscle cross-bridges containing phosphorylated and dephosphorylated myosin regulatory light chain. J Biol Chem 288(10):7012-7023.
56. Borejdo J, Rich R, Midde K (2012) Mesoscopic analysis of motion and conformation of cross-bridges. Biophys Rev 4(4):299-311.
57. Midde K, et al. (2014) Membrane topology of human presenilin-1 in SK-N-SH cells determined by fluorescence correlation spectroscopy and fluorescent energy transfer. Cell Biochem Biophys 70(2):923-932.
58. Roszik J, Lisboa D, Szollosi J, Vereb G (2009) Evaluation of intensity-based ratiometric FRET in image cytometry-approaches and a software solution. Cytometry 75(9): 761-767.
59. Lopez-Sanchez I, et al. (2014) GIV/Girdin is a central hub for profibrogenic signaling networks during liver fibrosis. Nat Commun 5:4451.
60. Chang A C, Dearman B, Greenwood J E (2011) A comparison of wound area measurement techniques: visitrak versus photography. Eplasty 11:e18.
61. Dunkel Y, et al. (2012) STAT3 protein up-regulates Gα-interacting vesicle-associated protein (GIV)/Girdin expression, and GIV enhances STAT3 activation in a positive feedback loop during wound healing and tumor invasion/metastasis. J Biol Chem 287(50):41667-41683.
62. Lin C, et al. (2014) Structural basis for activation of trimeric Gi proteins by multiple growth factor receptors via GIV/Girdin. Mol Biol Cell 25(22):3654-3671.
63. Garcia-Marcos M, Ear J, Farquhar M G, Ghosh P (2011) A GDI (AGS3) and a GEF (GIV) regulate autophagy by balancing G protein activity and growth factor signals. Mol Biol Cell 22(5):673-686.
64. Wang H M T, Taupin V, Eguchi A, Ghosh P, Farquhar M G (2014) GIV/Girdin links VEGF signaling to Akt survival signaling in podocytes independent of nephrin. J Am Soc Nephrol, in press.
65. Mittal Y, Pavlova Y, Garcia-Marcos M, Ghosh P (2011) Src homology domain 2-containing protein-tyrosine phosphatase-1 (SHP-1) binds and dephosphorylates G(alpha)-interacting, vesicle-associated protein (GIV)/Girdin and attenuates the GIV-phosphatidylinositol 3-kinase (PI3K)-Akt signaling pathway. J Biol Chem 286(37): 32404-32415.

Example 2

Activation of G Proteins by GIV-GEF is a Pivot Point for Insulin Resistance and Sensitivity Insulin resistance (IR) is a metabolic disorder characterized by impaired insulin signaling and cellular glucose uptake. The current paradigm for insulin signaling centers upon the insulin receptor (InsR) and its substrate IRS1; the latter is believed to be the sole conduit for post-receptor signaling. This example shows that GIV, a Guanidine Exchange Factor (GEF) for the trimeric G protein, Gαi, is another major hierarchical conduit for the metabolic insulin response. By virtue of its ability to directly bind InsR, IRS1 and PI3K, GIV serves as a key hub in the immediate post-receptor level which coordinately enhances the metabolic insulin response and glucose uptake in myotubes via its GEF function. Site-directed mutagenesis or phosphoinhibition of GIV-GEF by the fatty-acid/PKCθ pathway triggers IR. Insulin sensitizers reverse phosphoinhibition of GIV and reinstates insulin sensitivity. Evidence is provided for such reversible regulation of GIV-GEF in skeletal muscles from patients with IR. Thus, GIV is an essential upstream component that couples InsR to G-Protein signaling to enhance the metabolic insulin response, and impairment of such coupling triggers IR. Further, evidence is also provided that GIV-GEF serves as therapeutic target for exogenous manipulation of physiologic insulin response and reversal of IR in skeletal muscles.

Therefore, this example provides a single multi-modular signal transducer, GIV as a critical node in metabolic insulin signaling. Based on its ability to cross-talk with all these key mediators of metabolic insulin signaling, it is demonstrated that GIV is a key determinant of insulin sensitivity in physiology and its phosphoregulation by PKCθ triggers IR.

Experimental Procedures

Plasmids Constructs and Protein Expression.

Cloning of Gαi3 into pGEX-4T-1 (GST-Gαi3) or into pcDNA 3.1 plasmid, GIV-CT (aa 1660-1870) into pET28b (His-GIV CT) and RNA interference-resistant GIV constructs (Enomoto et al., 2005) into p3×FLAG-CMV™-14 plasmid (GIV-FLAG) have been described previously (Garcia-Marcos et al., 2010; Garcia-Marcos et al., 2009; Ghosh et al., 2008). The following constructs were gifts from other investigators: IRS1-HA from Michael Quon (U Maryland) (Kim et al., 2005); GST-tagged IRS1 domains (N: aa 2-516, M: aa 526-859 and C: 900-1235) from Xia-Jian Sun (University of Maryland) (Qiao et al., 1999) and CFP-pYIRS1-NSH2p85α-YFP (phocus-2nes) from Yoshio Umezawa (University of Tokyo) (Sato et al., 2002). Expression and purification of GST, GST-Gαi3 and His-GIV CT using Bl21(DE3) (Invitrogen) were done as described previously (Garcia-Marcos et al., 2009; Ghosh et al., 2010; Ghosh et al., 2008). Bacterial cultures were induced overnight at 25° C. with 1 mM isopropyl β-D-1-thiogalactopyranoside (IPTG). Pelleted bacteria from 1 L of culture were re-suspended in 10 ml GST-lysis buffer [25 mM Tris-HCl, pH 7.5, 20 mM NaCl, 1 mM EDTA, 20% (v:v) glycerol, 1% (v:v) Triton X-100, 2× protease inhibitor cocktail (Complete EDTA-free, Roche Diagnostics)] or His-lysis buffer [50 mM NaH$_2$PO$_4$ pH 7.4, 300 mM NaCl, 10 mM imidazole, 1% (v:v) Triton X-100, 2× protease inhibitor cocktail (Complete EDTA-free, Roche Diagnostics)] for GST or His-fused proteins, respectively. After sonication (3×30 s), lysates were centrifuged at 12,000 g at 4° C. for 20 min. Solubilized proteins were affinity purified on glutathione-Sepharose 4B beads (GE Healthcare) or HisPur Cobalt Resin (Pierce). Proteins were eluted, dialyzed overnight against PBS and stored at −80° C.

GIV and Gαi3 mutants were generated using specific primers (sequences available upon request) following the manufacturer's instructions (QuickChange II, Stratagene). TAT-GIV-CT-WT and TAT-GIV-CT-F1685A (TAT-GIV-CT-FA) constructs were prepared by cloning GIV-CT (aa 1660-1870) between NcoI and KpnI cloning sites within the pTAT-HA vector [gift from Steven Dowdy (Nagahara et al., 1998)]. A linker (GGSGHSG; SEQ ID NO: 11) was added between the HA-tag and the N-terminal sequence of GIV CT.

TAT-constructs were expressed using BL21(DE3)-pLysS (Invitrogen) and Terrific Broth (BioPioneer) supplemented with additives as per auto-induction protocols outlined by Studier F (Studier, 2005). Briefly, cultures of bacteria were grown at 300 rpm at 37° C. for 5 h, then at 25° C. overnight. Cells were lysed in 10 ml of buffer [50 mM NaH$_2$PO$_4$, 10 mM Imidazole, 400 mM NaCl, 1% (v:v) Sarkosyl, 1% (v:v) Triton X-100 and protease inhibitor mixture (Roche Diagnostics) (pH 7.4)], sonicated (3×30 s), cleared at 12,000×g for 20 min at 4° C. and affinity-purified on Ni-NTA agarose resin (Quiagen) (overnight at 4° C.). Proteins were eluted in elution buffer [50 mM NaH$_2$PO$_4$, 300 mM Imidazole, 400 mM NaCl, pH 7.4] and dialyzed overnight against TBS containing 400 mM NaCl.

Immunofluorescence and Confocal Microscopy.

Cells were fixed with 3% PFA in PBS for 25 min at room temperature, treated with 0.1 M glycine for 10 min, and subsequently blocked and permeabilized with PBS containing 3% BSA and 0.2% Triton X-100 (or only with 3% BSA in PBS buffer for surface labeling experiments where non-permeabilizing conditions were used) for 45 min at room temperature prior to antibody staining. Dilutions of antibodies are as follows: anti-phospho-GIV-Tyr1764 (1:200) (Ventana/Roche and Spring Biosciences); anti-HA (1:300) (Covance); anti-GFP, mouse anti-InsRβ and mouse anti-phospho-IRS1 (1:200) from Santa Cruz Biotechnologies; DAPI 1:1,000 (Molecular Probes); Secondary goat anti-rabbit (594) and goat anti-mouse (488) Alexa conjugated antibodies (1:500) from Molecular Probes. Coverslips were mounted with ProLong Gold (Life Technologies). Cells were imaged on a Leica SPE confocal microscope using a 63× oil objective using 488, 561 and 405 laser lines for excitation. Images were scanned using a line-average of 3. All images were processed using ImageJ software and assembled into figure panels using Photoshop and Illustrator (Adobe).

Cell Culture, Transfection, Immunoblotting, Immunofluorescence and Protein-Protein Interaction Assays.

These assays were carried out exactly as described before (Ghosh et al, 2010; Ghosh et al, 2008). All Odyssey images were processed using ImageJ software (NIH) and assembled for presentation using Photoshop and Illustrator software (Adobe). HeLa, Cos7 and L6 cells were cultured according to ATCC guidelines. Low passage (~3 to 8) L6 myoblasts were cultured under non-differentiating conditions in α-MEM (Invitrogen) media supplemented with 10% FBS and differentiated into myotubes by switching to 2% FBS media for 6-7 days.

Transfection was carried out with GeneJuice (Novagen) for DNA plasmids or Oligofectamine (Invitrogen) for siRNA oligos according to manufacturer's protocols. Silencer negative Control scrambled (Scr) siRNA used as control was purchased from Ambion and the previously validated (Enomoto et al., 2005) GIV siRNA sequence used was custom-ordered from Dharmacon. For TAT-construct transduction, cells were incubated with 300-800 nM of the TAT-proteins for 30 min at 37° C. prior to three washes with PBS and addition of fresh growth media. For assays involving insulin (Novagen) stimulation of TAT-treated cells, such stimulation was carried out 90 min after transduction.

Generation of Stable Cell Lines.

HeLa cell lines stably expressing GIV-3×FLAG-WT, FA or SD mutants were extensively used in previous work (Lopez-Sanchez et al., 2013). GIV-3×FLAG expression was ~1-2 fold compared to the levels of endogenous GIV. L6 stable cell lines expressing GIV-3×FLAG constructs or L6 stable cell lines expressing Gαi3 WT or Gαi3-W258F (Gαi3-WF) constructs were selected as previously described (Garcia-Marcos et al., 2009; Lopez-Sanchez et al., 2013) with the neomycin analog G418 (Cellgro) at 500 µg/ml. Expression of various GIV constructs in L6 cells were confirmed as ~1-1.5 fold above the endogenous levels by immunoblotting. In all experiments using stable cells, the endogenous GIV was depleted using GIV siRNA such that the cells exclusively expressed the desirable siRNA-resistant GIV mutant at near-physiologic levels. Similarly, Gαi3 expression was confirmed by immunoblotting with anti-Gαi3 antibody and expression was ~1.5-2 fold above the endogenous levels. Control shRNA and GIV shRNA Cos7 stable cell lines were selected with 2 µg/ml of Puromycin (GIBCO). The shGIV sequence used was previously validated (Enomoto et al., 2005) and is identical to the sequence of GIV siRNA. Depletion of GIV was verified using GIV-CT antibody with an efficiency of ~95%.

Sodium Palmitate, Pioglitazone and Other Treatments.

Unless otherwise indicated, serum starvation of cells for use in experiments involving insulin stimulation was carried out by growing cells overnight in the presence of no serum (i.e., 0% FBS) in the case of Cos7 and L6 cells, or in the presence of 0.2% FBS in the case of HeLa cells. To induce IR, cells were pre-treated with Sodium Palmitate (PA; Sigma-Aldrich) (0.5 mM, stock solution at 5 mM/5% FFA-free BSA in ethanol) or vehicle control (5% FFA-free BSA in ethanol) for 16 h. To reverse IR with TZDs, cells were treated with 50 μM Pioglitazone (Pio) (Sigma-Aldrich) or DMSO (vehicle control) for 18 h prior to stimulation with 100 nM insulin. Treatment with PKCθ pseudo-substrate inhibitor (Santa Cruz Biotechnologies) was performed at 10 μM for 16 h.

Cell Lysis and Immunoblot Analysis.

Whole cell lysates were prepared after washing cells with cold PBS prior to resuspending and boiling them in sample buffer. Cell lysates used as a source of proteins for pulldown assays or immunoprecipitation were prepared by breaking cells during passage through a 28-gauge needle in the presence of lysis buffer [20 mM Hepes (pH 7.2), 5 mM Mg-acetate, 125 mM K-acetate, 0.4% Triton X-100, 1 mM DTT, supplemented with sodium orthovanadate (500 μM), phosphatase (Sigma), and Protease (Roche) inhibitor cocktails] at 4° C. Crude lysates were cleared of insoluble particles/debris by centrifugation at 10,000×g for 10 minutes.

Protein samples for immunoblotting were run on SDS/PAGE gels and transferred onto PVDF membranes (Millipore). Membranes were blocked with PBS containing 5% non-fat milk (or with 5% BSA when probing for phosphorylated proteins) before incubation with primary antibodies. GIV was detected using rabbit anti-GIV coiled-coil (Millipore) (1:500); GIV-CT (Santa Cruz Biotechnologies) (1:500); phospho-Tyr1764-GIV (1:500) and phospho-Ser1689-GIV (21$^{st}$ Century Biochemicals) (1:250) antibodies. Other antibodies used in this work include rabbit polyclonal antibodies against Gαi3 (1:333), pan-GP (1:250) and phospho-IRS1 (1:500) from Santa Cruz Biotechnologies; and phospho-Akt (1:250); total Akt (1:250); phospho-ERK (1:250); phospho-AS160 (1:250); total InsRβ (1:500) and total IRS1 (1:500) from Cell signaling. Mouse monoclonal Abs against phospho-InsRβ (1:250), His (1:1000), β-tubulin (1:1000), GFP (1:500) from Santa Cruz Biotechnologies, and control IgG (Bio-Rad Laboratories) were commercially obtained. Goat anti-rabbit and goat anti-mouse Alexa Fluor 680 or IRDye 800 F(ab')$_2$ secondary antibodies were purchased from Li-Cor Biosciences. Images were processed with ImageJ software (NIH) and assembled as figure panels using Photoshop and Illustrator software (Adobe).

Glucose Uptake Assay.

Glucose uptake assays were performed without the use of radioisotopes as described previously (Yamamoto et al., 2006). HeLa and L6 cells grown in 6-well plates were stimulated with insulin in KRH Buffer [50 mM HEPES, 137 mM NaCl, 4.7 mM KCl, 1.85 mM CaCl$_2$, 1.3 mM MgSO$_4$, and 0.1% (w/v) BSA-FFA free, pH 7.4]. Cells were incubated with 1 mM 2-deoxyglucose (2-DG) for 20 min, washed, and subsequently lysed with 0.1 N NaOH. The lysates were transferred into eppendorf tubes and samples were incubated in a water bath maintained at 80° C. for 45 min to degrade endogenous NAD(P)H and NAD(P)$^+$. An equal volume each of 0.1 N HCl and Triethanolamine (200 mM TEA, pH 8.1) buffer were added to each tube. Samples were subsequently mixed with assay solution [50 mM TEA, 0.02% BSA-FFA free, 10 μM NAD(P)$^+$, 0.2 U/ml Diaphorase, 6 nM Resazurin sodium, 15 U/ml G6PDH (Santa Cruz Biotechnologies)] and incubated at 37° C. for 90 min. Fluorescence intensity ($\lambda_{ex}$=550 nM, $\lambda_{em}$=590 nM) was determined using a Tecan Inifinite M1000 PRO and normalized to total protein, as determined using BCA assay (Thermo Scientific).

GST Pulldown Assays and Immunoprecipitation.

Purified GST-Gαi3, GST-tagged IRS1 domains or GST alone were immobilized on glutathione-Sepharose beads (GE Healthcare) for 1 h at room temperature as described before (Garcia-Marcos et al., 2012; Ghosh et al., 2010; Ghosh et al., 2008; Lin et al., 2011). L6 lysates or His-GIV CT protein were added to each tube, and binding reactions were carried out for 4 h at 4° C. with constant tumbling in binding buffer [50 mM Tris-HCl (pH 7.4), 100 mM NaCl, 0.4% (v:v) Nonidet P-40, 10 mM MgCl$_2$, 5 mM EDTA, 2 mM DTT, protease inhibitor mixture]. Beads were washed (4×) with 1 mL of wash buffer [4.3 mM Na$_2$HPO$_4$, 1.4 mM KH$_2$PO$_4$ (pH 7.4), 137 mM NaCl, 2.7 mM KCl, 0.1% (v:v) Tween 20, 10 mM MgCl$_2$, 5 mM EDTA, 2 mM DTT] and bound complexes were eluted by boiling in Laemmli's sample buffer. When GST-Gαi3 was used in the assay, both binding buffer and washing buffer were supplemented with 30 μM GDP and bound proteins were eluted by incubating at 37° C.

For Immunoprecipitation, cell lysates (~2 mg of protein) were incubated for 3 h at 4° C. with 2 μg anti-HA, phospho-InsRβ, anti-GFP mAbs or pre-immune control mouse IgG. Protein G Sepharose beads (GE Healthcare) were added and incubated at 4° C. for an additional 60 min. Beads were washed and bound immune complexes were eluted by boiling in Laemmli's sample buffer (Garcia-Marcos et al., 2011; Ghosh et al., 2010; Ghosh et al., 2008).

dSTORM and FRET Imaging.

Direct Stochastic Optical Reconstruction Microscopy imaging was performed to reveal the interaction endogenous Gαi3 and active InsRβ at molecular level (Huang et al., 2010). Control shRNA and GIV shRNA Cos7 stable cells were starved and stimulated with 100 nM insulin and stained with anti-Gαi3 (1:30) (Calbiochem) and phosho-InRβ antibodies. Slides were sealed in STORM buffer [20% Glucose, 500 μg/ml Glucose Oxidase, 40 μg/ml Catalase and 0.1 M Cysteamine (MEA) dissolved in PBS] and imaged using Nikon Eclipse Ti super resolution microscope (Moores Cancer Center Core Facility).

FRET assays were performed using the intracellular phosphorylation biosensors custom (phocus-2nes) (Sato et al., 2002). Resonance energy transfer from CFP to YFP denotes phosphorylation of the Y941 residue of IRS-1 substrate and binding of the SH2 domain of PI3K revealing activation of the PI3K pathway upon stimulation with insulin. GIV shRNA Cos-7 stable cells were transfected with phocus-2nes and GIV-WT-FLAG or GIV-S1689D-FLAG. Cells were starved and stimulated with insulin, and stained with anti-FLAG antibody following the standard immunofluorescence protocol. Leica laser scanning confocal microscope was used to generate optical slices of 0.5 μm thickness and the Z plane that resolved most of the plasma membrane was imaged through sensitized emission. FRET efficiency was computed on a pixel by pixel basis from normalized ratiometric images obtained in individual channels (donor, acceptor and FRET) (Roszik et al., 2009). Region of Interest (ROI) were drawn along the plasma membrane and analyzed for FRET to determine sub-cellular phosphorylation of IRS1 upon insulin stimulation.

Patient Samples.

Biopsies of vastus lateralis muscle used for GIV phosphorylation analysis were collected in the Special Diagnostic and Treatment Unit (SDTU) of the Veterans Affairs Medical Center (San Diego, Calif.) and the General Clinical Research Center (GCRC) (University of California, San Diego, Calif.). Muscle samples were collected from healthy normal cycling women or women with PCOS before and after pioglitazone (45 mg/d, for 6 months) (Aroda et al., 2009). After collection, muscle tissue was immediately frozen in liquid nitrogen. The experimental protocol was approved by the Human Research Protection Program of the University of California (San Diego, Calif.). Informed written consent was obtained from all subjects after explanation of the protocol.

Data Analysis and Statistics.

All experiments were repeated at least three times, and results were presented either as one representative experiment or as average±S.D or S.E.M. Statistical significance was assessed with two-tailed Student's t-test.

Results and Discussion

Activation of Gαi by GIV-GEF is Required for Glucose Uptake in Skeletal Muscles.

Figures 9A, 9B, 9C, 9D, 9E, 9F:
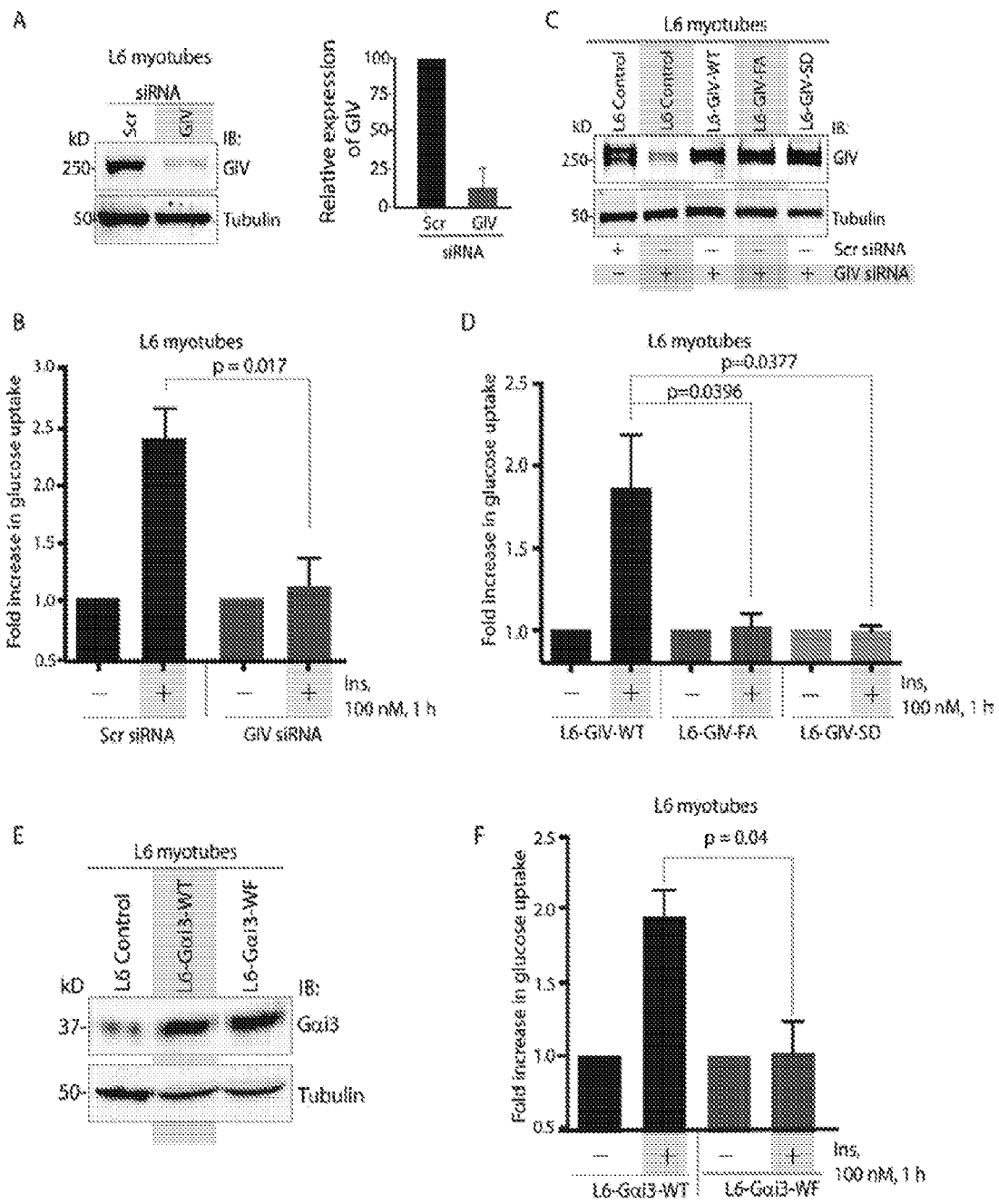
FIGS. 9A-9F. Activation of Gαi by GIV-GEF is essential for glucose uptake in skeletal muscles.

To determine the role of GIV-GEF in insulin resistance, differentiated L6 rat skeletal myotubes were used. The rationale for this choice was guided by two facts: 1) although both adipocytes and skeletal muscles are sites for IR, full-length GIV is expressed more abundantly in skeletal muscles than in mature adipocytes (Uhlen et al, 2010); and 2) a recent study showed that levels of expression of GIV mRNA in skeletal muscle biopsies from normal subjects tracks with insulin sensitivity, as measured by a hyperinsulinemic-euglycemic clamp (Hartung et al, 2013). It was found that depletion of GIV in L6 myotubes (by ~80-85%; FIG. 9A) reduced the efficiency of glucose uptake by ~by 50% (FIG. 9B), as determined by a well-established fluorometric assay (Yamamoto et al, 2006). This defect was rescued by stably expressing siRNA-resistant wild type GIV (GIV-WT), but not the GEF-deficient F1685A mutant of GIV (GIV-FA) which can neither bind, nor activate Gαi (Garcia-Marcos et al, 2009) (FIGS. 9C & 9D). It is noteworthy that the levels of stable expression of GIV-WT or mutants in GIV-depleted L6 myotubes were similar to the levels of endogenous GIV in these cells (FIG. 9C), indicating that the effects observed are not merely due to overexpression of GIV at non-physiologic levels. These findings indicate that GIV is required for glucose uptake in skeletal muscles and that its GEF domain is essential.

Next, it was determined if phosphoinhibition of GIV's GEF at Ser1689 by PKCθ (Lopez-Sanchez et al, 2013) also inhibits glucose uptake. It was found that glucose uptake in cells expressing the constitutively phosphoinhibited S1689D mutant of GIV (GIV-SD) was half as efficient compared to those expressing GIV-WT (FIGS. 9C & 9D), indicating that phosphoinhibition of GIV's GEF function by PKCθ impairs glucose uptake in response to insulin. These findings were reproduced in HeLa cells (FIGS. 16A-16D), indicating that the effect of GIV-GEF we observe on glucose uptake may not be a restricted only to L6 myotubes, but represent a fundamental effect on Insulin response.

To further pinpoint impairment of Gi activation by GIV-GEF as the cause, glucose uptake was monitored in L6 myotubes stably expressing either wild-type (Gαi3-WT) or a dominant negative W258F mutant of Gαi3, henceforth referred to as Gαi3-WF (FIG. 9E), which cannot bind or be activated by GIV, but localizes and interacts with Gβγ, GPCRs, and Gαi regulators similar to Gαi3-WT (Garcia-Marcos et al, 2010). Gαi3 (and not αi1/2) was analyzed because it is the most abundant Gαi subunit expressed in skeletal muscles, as confirmed by proteomics (Hwang et al, 2010). Glucose uptake was reduced in cells expressing Gαi3-WF compared those expressing Gαi3-WT (FIG. 9F), confirming that GIV drives efficient glucose transport after insulin stimulation via its ability to activate Gαi proteins.

GIV Binds Ligand Activated InsRβ and Modulates Multiple Tiers of Metabolic Insulin Signaling Via its GEF Function.

Figures 10A, 10B, 10C, 10D, 10E, 10F, 10G, 10H:
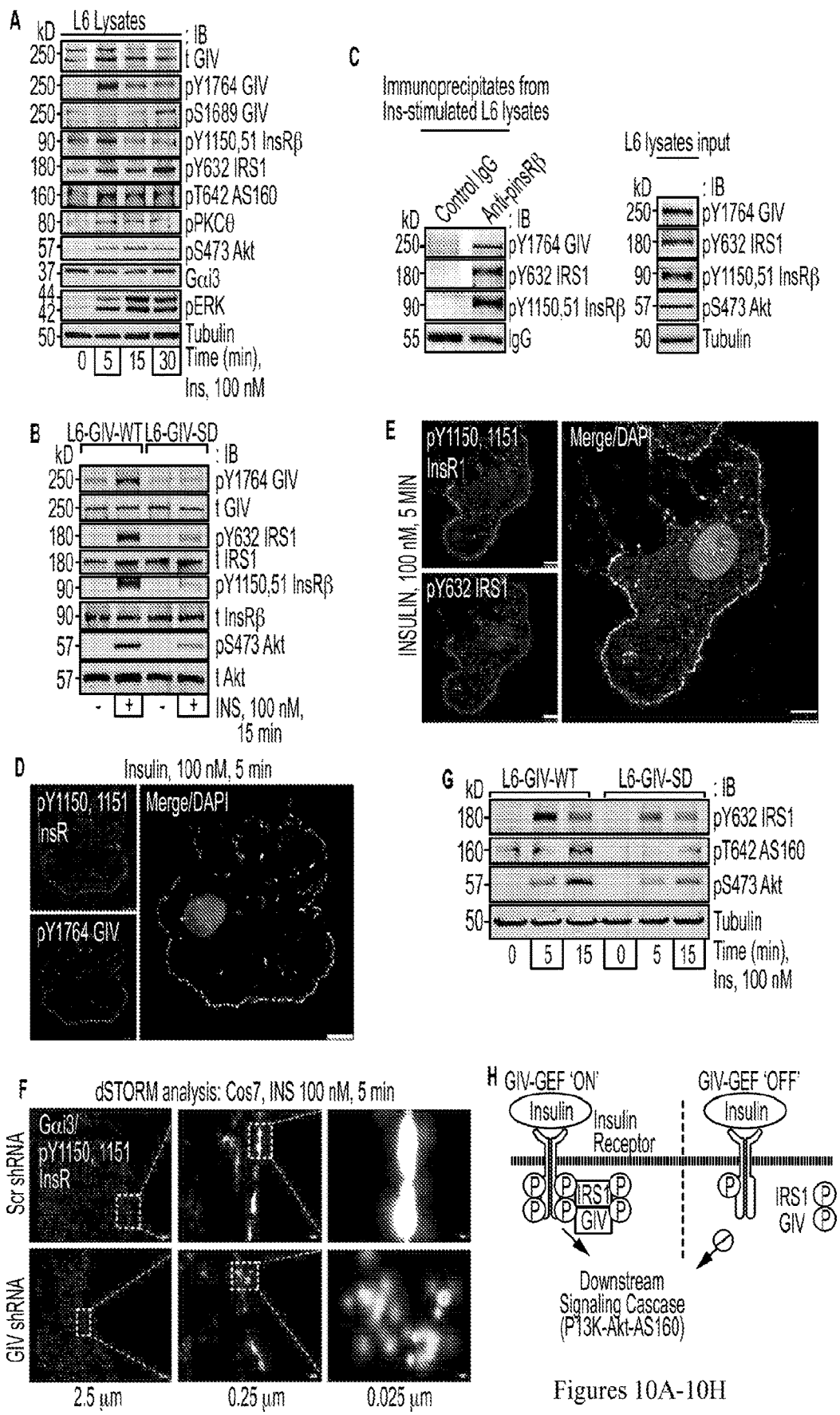
FIGS. 10A-10H. GIV-GEF binds and enhances autophosphorylation of InsRβ and downstream metabolic insulin response.
Figure 17A:
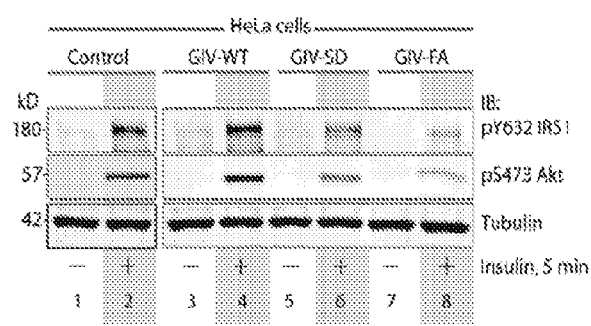
FIGS. 17A-17B. GIV enhances insulin signaling via its GEF function.

To determine how GIV's GEF function affects the insulin signaling cascade, key components of metabolic insulin signaling in L6 myotubes responding to insulin were analyzed. Immunoblotting for phosphoproteins revealed that insulin triggered activation of GIV at 5 min, coincides with peak autophosphorylation of InsRβ, and is followed by sustained phosphoactivation of IRS1 and Akt and phosphoinhibition of the GSV-associated Rab-GAP AS160 (FIG. 10A); the latter is a key trigger step for exocytosis of GSVs (Miinea et al, 2005). Activation of PKCθ was initiated by 5 min and sustained up to 30 min, and inhibitory phosphorylation of GIV at S1689 by PKCθ peaked at 30 min. The time-line of these events is consistent with the previously described role of this phosphoevent in the termination of GIV's GEF activity and disengaging GIV from Gαi (Lopez-Sanchez et al, 2013). A similar analysis comparing L6 myotubes expressing GIV-WT or GIV-SD revealed that phosphoinhibition of GIV's GEF activity by PKCθ affects several of these key upstream events. Compared to L6-GIV-WT cell lines, global suppression of the insulin response was encountered in L6-GIV-SD cells, starting with the most upstream event, i.e., suppressed autophosphorylation of InsRβ at Y1150 and Y1151, which are essential for maximal phosphoactivation of substrate proteins (Flores-Riveros et al, 1989) (FIG. 10B). At the immediate post-receptor level, phosphoactivation of GIV and IRS1 were suppressed and Akt phosphorylation downstream was impaired (FIG. 10B). Similar findings were noted also in paired HeLa-GIV-WT vs HeLa-GIV-SD cells (FIG. 17A).

Figure 17B:
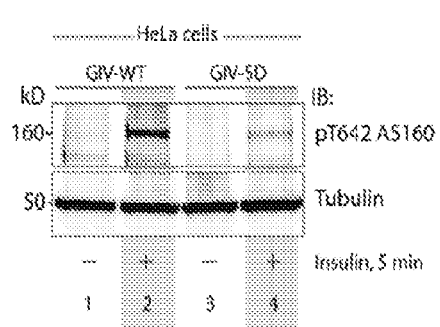

Previous work showed that GIV's C-terminal SH2-like domain directly binds autophosphorylated cytoplasmic tails of multiple RTKs, including InsRβ (Lin et al, 2014; Midde et al, 2015). In L6 myotubes, active GIV[pY1764] coimmunoprecipitated with ligand-activated InsRβ-IRS1 complexes (FIG. 10C). Active GIV[pY1764] also colocalized with the autophosphorylated InsRβ at PM microdomains (FIG. 10D) where activated IRS1 adaptors coexist (FIG. 10E). These findings suggest that the InsRβ-GIV-IRS1 complexes observes in FIG. 10C are likely assembled at the PM. To determine if GIV links Gαi proteins to ligand-activated InsRβ at these PM microdomains, dSTORM imaging was used, which achieves a spatial resolution of ~25 nm, and a high degree of colocalization between endogenous proteins indicates that they are likely to interact (Huang et al, 2010). In control cells, but not in GIV-depleted cells Gαi3 and ligand-activated InsRβ showed a high degree of colocalization along the PM (FIG. 10F), indicating that active InsRβ and Gαi3 come within close proximity of each other exclusively in the presence of GIV-GEF. The impairment of autophosphorylation of InsRβ in GEF-deficient L6-GIV-SD mutant cells, was also accompanied by defects in downstream activation of Akt and phosphoinactivation of its target Rab-GAP, AS160 (FIG. 10G & FIG. 17B). Taken together, these results demonstrate that GIV binds to ligand-activated InsRβ-IRS1 complexes on microdomains at the PM and links Gαi to such complexes. The presence or absence of a functional GIV-GEF, via which GIV links and activates Gi in the vicinity of RTKs, appears to be a key determinant of whether multiple tiers within the metabolic insulin signaling cascade are activated maximally, beginning with the autophosphorylation and activation of InsRβ (FIG. 10H).

GIV Directly Binds and Modulates the Localization and Functional Phosphorylation of IRS1

Figures 11A, 11B, 11C:
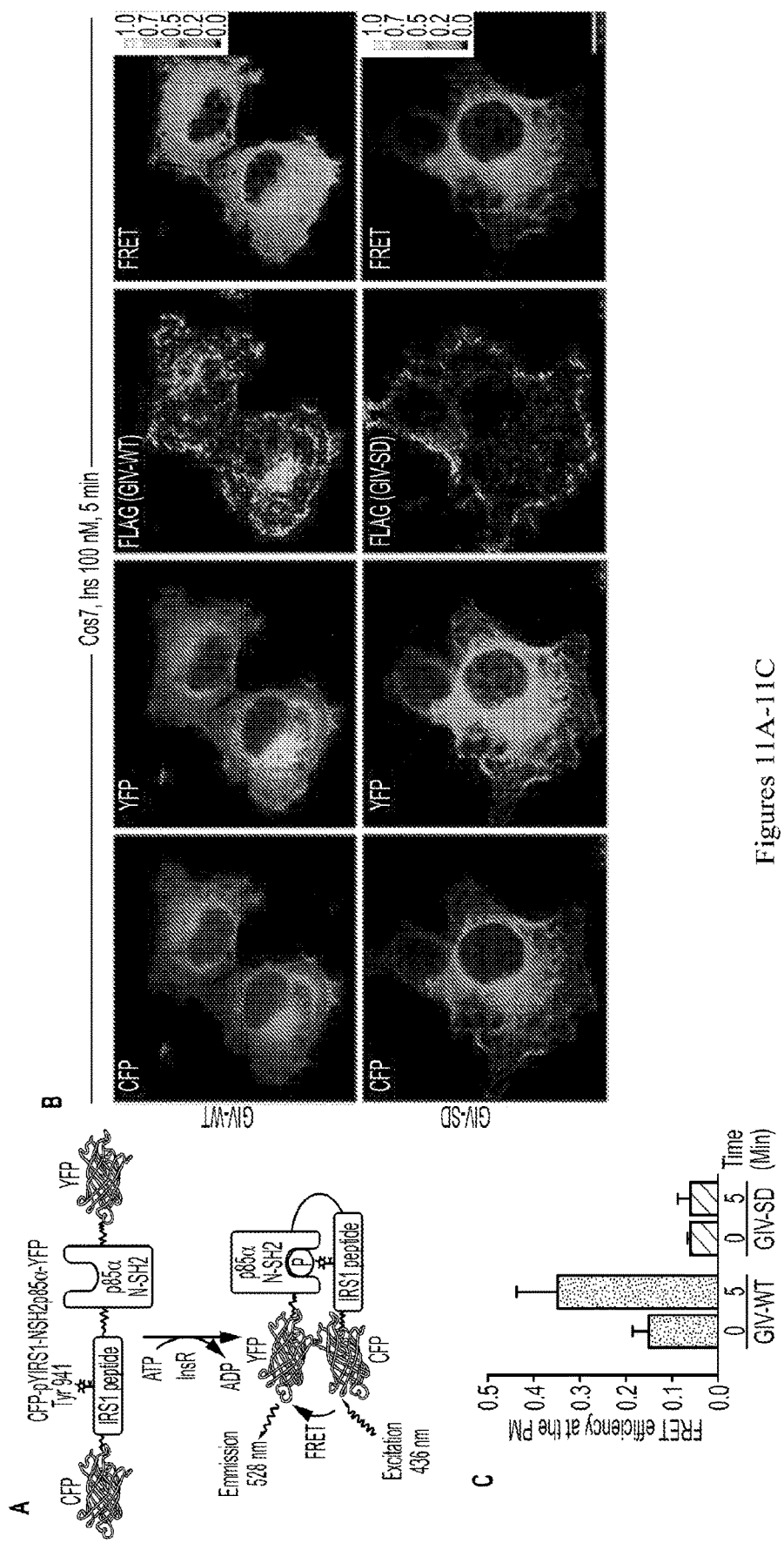
FIGS. 11A-11G. GIV-GEF directly binds and regulates the localization and activation of IRS1.
Figures 11, 11D, 11E, 11F, 11G:
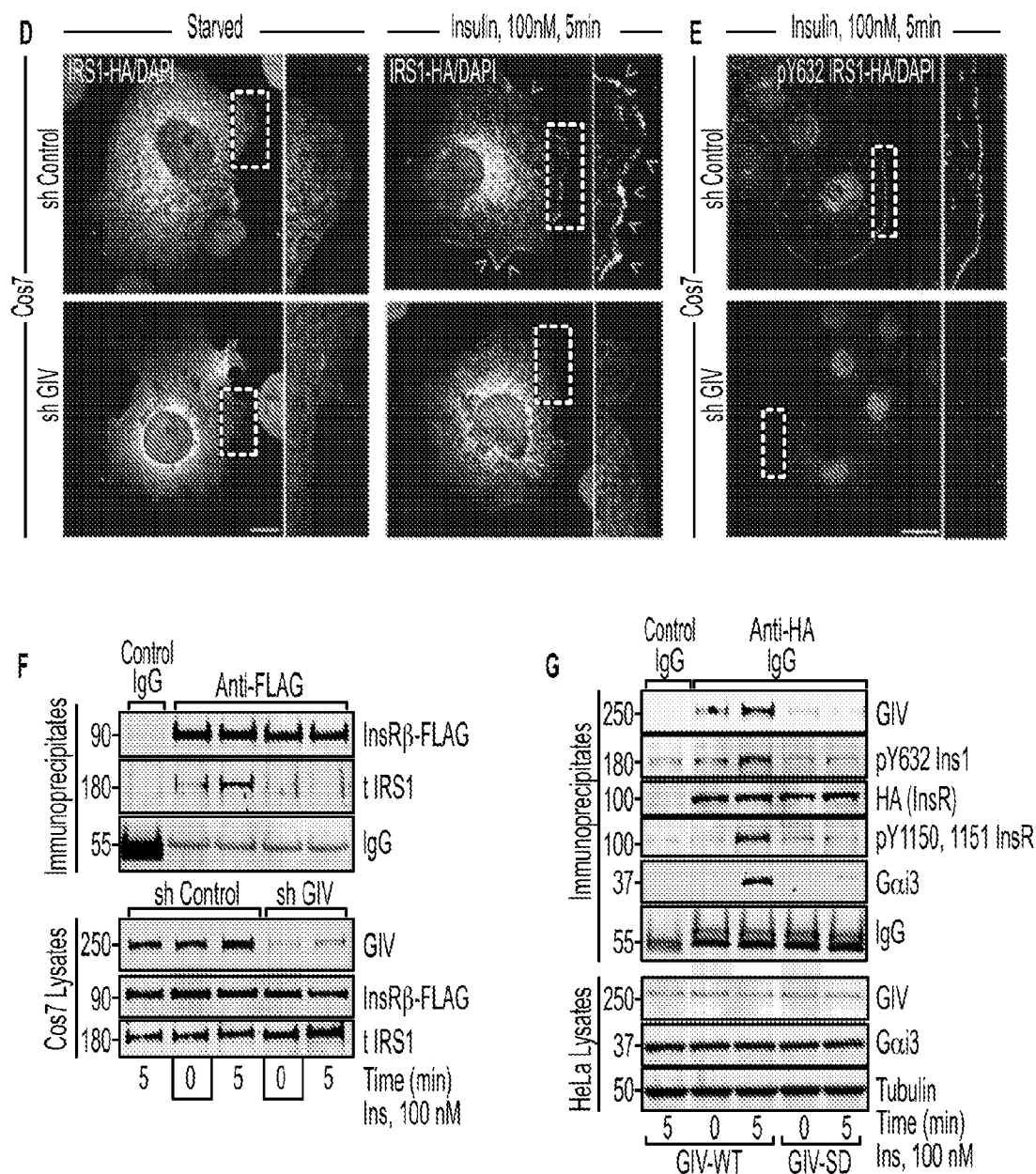
Figure 18A:
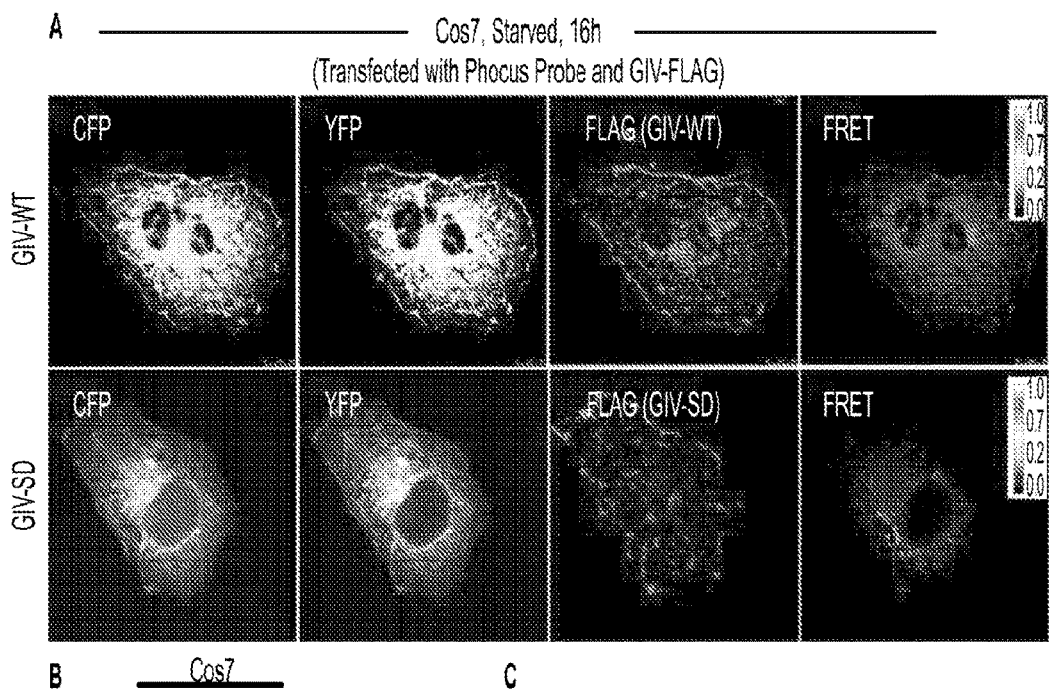
FIGS. 18A-18D. GIV and its GEF function modulates the localization and phosphorylation of IRS1.
Figure 18B:
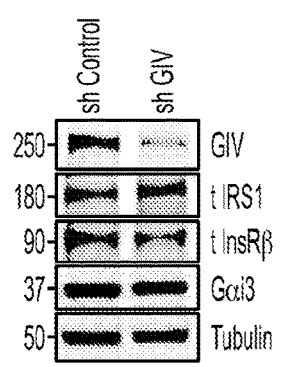
Figure 18C:
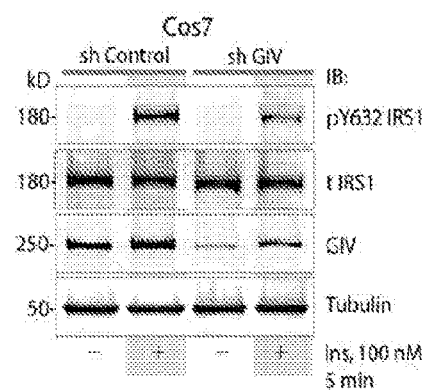

Next, it was further investigated how GI affects the phosphorylation/activation of IRS1, which is a major adaptor for the metabolic insulin responses. Because the hypophosphorylation of IRS1 observed by immunoblotting L6 myotubes and HeLa cells expressing the GEF-deficient, SD phosphomimetic mutant do not provide enough information about the spatial and temporal dynamics of IRS1 phosphodephosphorylation in cells, a genetically encoded fluorescent biosensor, phocus-2nes (Sato et al, 2002) was used in fluorescence resonance energy transfer (FRET) studies. This biosensor shows energy transfer only when Y941 on IRS1 is phosphorylated and presents a docking site for the N—SH2 domain of p85α (PI3K), thereby providing a readout of the function of such phosphorylation (FIG. 11A). In cells expressing GIV-WT, a significant increase in FRET efficiency was observed at/near the PM (F.E. 0.34±0.08) within 5 min after insulin stimulation; however, in cells expressing GIV-SD, that response was blunted (F.E. 0.06±0.03; FIGS. 11B-11C, FIG. 18A), confirming that phosphoinhibition of GIV-GEF impairs functional phosphorylation of IRS1 at the PM. Because functional phosphorylation of IRS1 involves several steps, it was asked if GIV is required for the two earliest ones, i.e., translocation of IRS1 from cytosol to the PM and its subsequent phosphorylation at that location in response to insulin. Compared to control cells, both steps were impaired in GIV-depleted cells (FIGS. 11D-11E, FIGS. 18B-18C). Co-immunoprecipitation studies on control or GIV-depleted cells further confirmed that recruitment of IRS1 to the activated InsRβ was impaired in the absence of GIV (FIG. 11F).

Figure 18D:
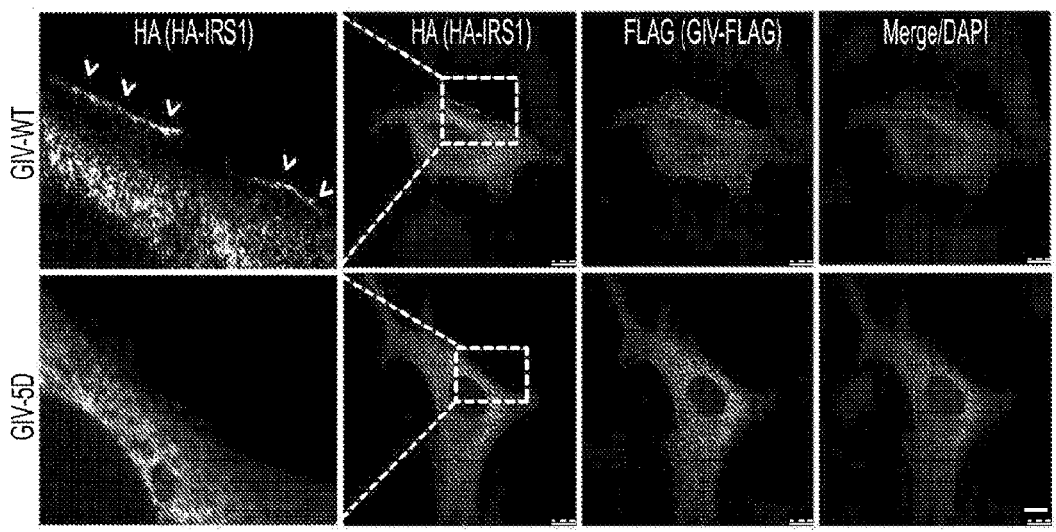

To further pinpoint if GIV's GEF function is essential for the recruitment of IRS1 to ligand-activated InsR, first, insulin-triggered translocation of IRS1 from the cytosol to the PM was studied in Cos7 cells expressing WT or SD GIV mutant (FIG. 18D). It was found that IRS1 localized to the PM in cells expressing GIV-WT, exclusively after ligand stimulation, whereas localization at the PM was suppressed in cells expressing GIV-SD. Next, receptor-bound complexes were analyzed by immunoprecipitation assays in GIV-depleted HeLa cells stably expressing WT or SD GIV mutant (FIG. 11G). In HeLa-GIV-WT cells, ligand stimulation triggered robust autophosphorylation of InsR (pY1150, 1151), which coincided with the recruitment of pYIRS1, GIV and Gαi3 (FIG. 11G). Consistent with the prior observations in L6-GIV-SD cells (FIG. 10B), autophosphorylation of InsR was suppressed also in HeLa-GIV-SD cells, and receptor bound complexes (InsR-GIV-G protein or InsR-IRS1) were decreased. These results not only pinpoint the role of GIV's GEF function in enhancing the recruitment of IRS1 to ligand-activated InsR, but also demonstrate the inhibitory effect of pS1689 GIV on both InsR-IRS1 and InsR-Gαi3 complexes.

Figures 12A, 12B, 12C:
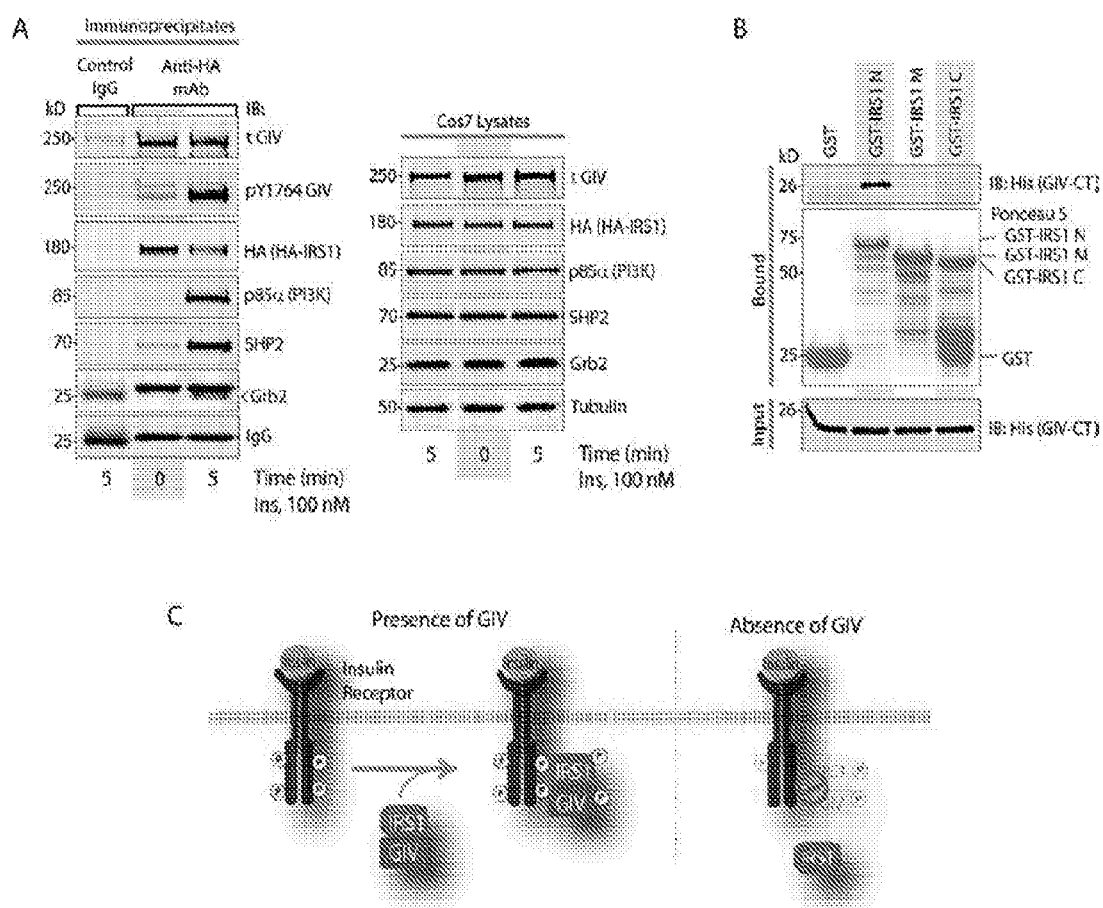
FIGS. 12A-12C. GIV directly and constitutively binds IRS1.
Figures 19A, 19B:
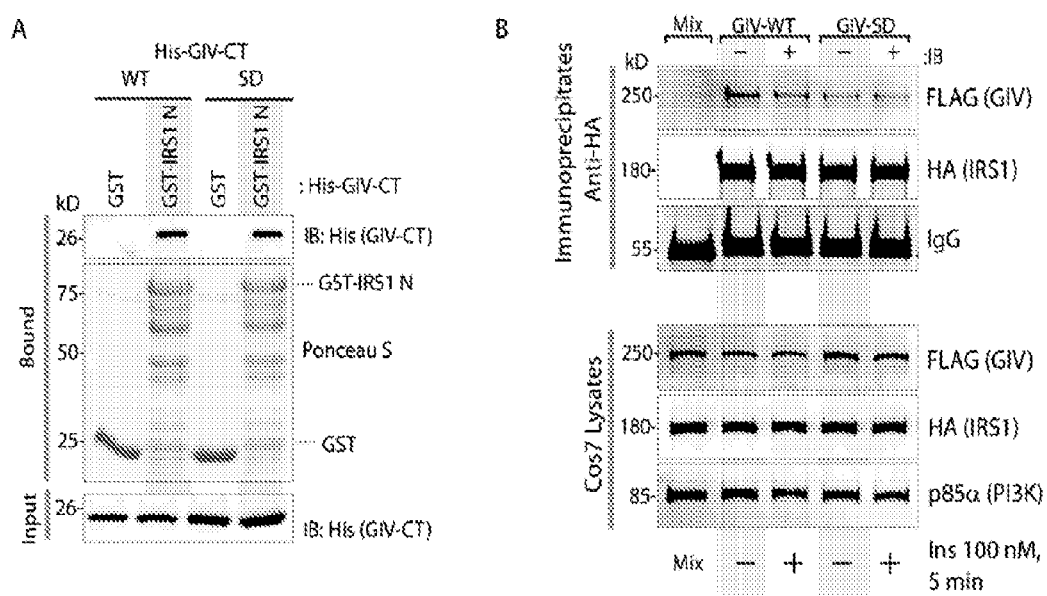
FIGS. 19A-19B. Phopshorylation of GIV at S1689 and inhibition of its GEF function does not affect the GIV-IRS1 interaction.

Because of the global effect of GIV depletion observed on IRS1 localization, recruitment and phosphoactivation, it was determined if GIV binds IRS1. GIV coimmunoprecipitated with IRS1 before and after insulin stimulation (FIG. 12A), indicating that the GIV-IRS1 interaction is constitutive. Pulldown assays with recombinant proteins showed that His-GIV-CT specifically bound the N-terminus of IRS1, demonstrating that the interaction is direct (FIG. 12B). Furthermore, both WT and SD mutant GIV proteins bound IRS1 equally (FIGS. 19A-19B) indicating that phosphorylation of GIV at S1689 by PKCθ does not impair GIV's ability to bind IRS1, and suggests that GIV may bind IRS1 via a domain that is distinct from its GEF module. Despite the fact that GIV-SD retains its ability to bind IRS1, localization and activation of IRS1 were impaired in GIV-SD cells (FIG. 11B-11C, FIG. 18D), suggesting that the GIV-IRS1 interaction may serve a different role independent of the observed effects of phosphoinhibition of GIV-GEF on IRS1 signaling. Therefore, the GIV-IRS1 interaction may serve as a scaffold for the stabilization of InsRβ(RTK)/GIV/IRS1 ternary complexes at the PM, within which GIV's GEF function may modulate the phosphoactivation of IRS1 downstream of growth factors (FIG. 12C).

GIV-GEF is a Target for the Antagonist Actions of Fatty Acids and Insulin Sensitizers.

Figures 13A, 13B, 13C, 13D, 13E, 13F, 13G, 13H, 13I:
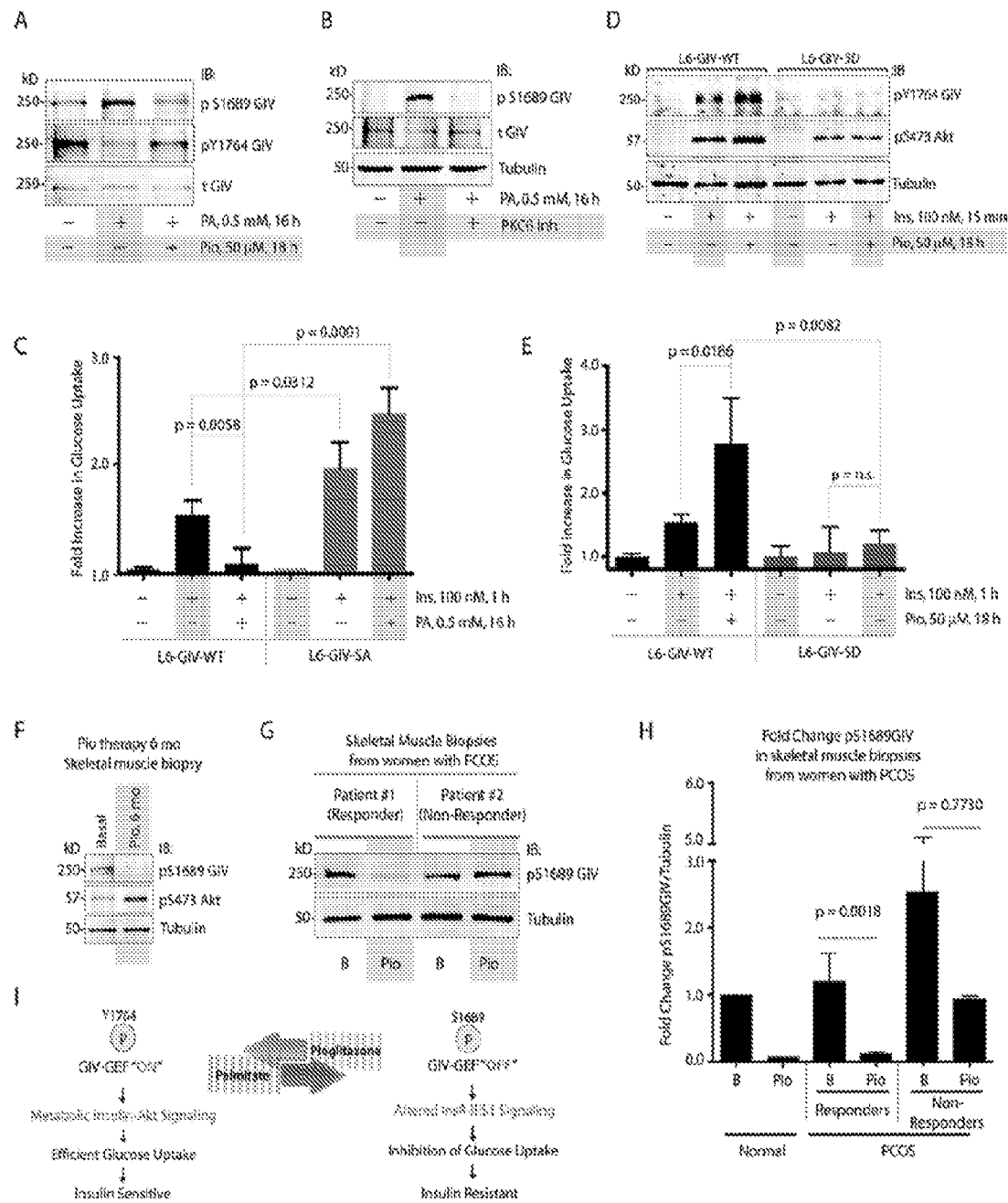
FIGS. 13A-13I. Phosphoinhibition of GIV-GEF by PKCθ is required for Palmitate (PA)-induced IR and dephosphorylation is essential for the action of Pioglitazone (Pio).

Because PKCθ is the kinase that orchestrates lipid-induced insulin resistance (Haasch et al, 2006), it was determined whether fatty acids induce IR in part by phosphoinhibition of GIV-GEF at S1689 by PKCθ. When IR was induced in L6 cells using albumin-conjugated sodium palmitate (PA), which is known to activate PKCθ (Griffin et al, 1999), it was found that phosphorylation of GIV at S1689 was enhanced, GIV's ability to bind Gi was reduced and phosphorylation of GIV at Y1764 was suppressed (FIG. 13A & FIG. 20A) indicating that PA induces phosphoinhibition of GIV-GEF and concomitantly suppresses tyrosine-based signaling via GIV. PA requires PKCθ to exert such phosphoinhibition because inhibition of PKCθ abolished phosphoinhibition of GIV-GEF (FIG. 13B). When PA-treated, insulin-resistant L6 cells were incubated with Pioglitazone (Pio), an insulin sensitizer in the thiazolidinedione class of drugs, phosphorylation of GIV at S1689 was reduced and tyrosine phosphorylation of GIV was enhanced, indicating that Pio antagonized both the effects of PA and effectively reversed the phosphoinhibition of GIV-GEF by PKCθ (FIG. 13A). Consistent with its role as a true insulin sensitizer that improves insulin action in peripheral tissues, Pio also enhanced tyrosine phosphorylation of GIV and Akt signaling triggered by insulin in insulin sensitive L6 cells never exposed to PA (FIGS. 20B-20C).

Next, it was investigated whether phosphoinhibition of GIV-GEF by PKCθ in L6 myotubes plays a role in mediating the antagonistic effects of PA and Pio in the induction and reversal of IR, respectively. PA induced IR in L6-GIV-WT cells, as determined by a blunted glucose-uptake response to insulin (FIG. 13C). However, L6 cells expressing a non-phosphorylatable GIV S1689A mutant (L6-GIV-SA) were resistant to PA, i.e., these cells remained sensitive to insulin regardless of PA treatment and demonstrated higher glucose uptake compared to L6-GIV-WT cells (FIG. 13C). These results demonstrate that the selective inhibition of GIV-GEF by PKCθ via phosphorylation of a single Ser1689 is an essential mechanism by which PA triggers IR in L6 myotubes. As for Pio, it was found that it reinstated insulin signaling in PA-treated, insulin resistant L6-GIV-WT cells, as determined by restored tyrosine phosphorylation of GIV and Akt signaling (FIG. 13D, FIG. 20D). However, L6 cells expressing a constitutively phosphoinhibited GIV SD mutant (L6-GIV-SD) were resistant to Pio, i.e., these cells showed no discernible enhancement of signaling compared to L6-GIV-WT cells (FIG. 13D & FIG. 20D). Furthermore, Pio reversed the PA-induced IR state in L6-GIV-WT cells, but not in L6-GIV-SD cells, as determined by glucose uptake after insulin stimulation (FIG. 13E). Because Pio is known to improve insulin sensitivity in muscle tissue in part by antagonizing the activity of protein kinases such as PKCθ (Markova et al, 2010), these results demonstrate that reversal of phosphoinhibition of GIV-GEF by PKCθ on Ser1689 is an essential mechanism via which Pio reverses IR and sensitizes L6 myotubes to the action of insulin. The inability to reverse such phosphoinhibition (as in the case of the GIV-SD mutant which mimics a constitutive phosphoinhibited state) makes cells non-responsive to the insulin-sensitizing actions of Pio.

The physiologic significance of these observations in cultured L6 myotubes was confirmed by findings in patients with IR, where chronic treatment with Pio reduced the phosphoinhibition of GIV-GEF and enhanced phosphorylation of Akt in skeletal muscles (vastus lateralis) of obese type II diabetic patients (FIG. 13F). Moreover, patients with Polycystic Ovarian Syndrome (PCOS) in whom IR was clinically reversed by Pio therapy, i.e., responders [as determined by 24 h glucose levels and glucose disposal rate (GDR) determined by a hyperinsulinemic/euglycemic clamp] showed a significant reduction in phosphoinhibition of GIV at S1689 in their muscles. By contrast, PCOS patients who failed the Pio treatment trial (i.e., non-responders) had high pre-treatment and/or post-treatment levels of phosphoinhibition of GIV-GEF (FIGS. 13G-13H). Taken together, these results demonstrate that a single phosphoevent (PKCθ-dependent phosphorylation of GIV at S1689), which selectively inhibits GIV-GEF, and therefore abolishes activation of Gi by GIV, is a common pivot point for both PA and Pio to exert their antagonistic actions in IR. Phosphorylation at S1689 is essential for PA to induce IR, whereas dephosphorylation is required for Pio to enhance tyrosine phosphorylation of IRS1 and GIV, restore Akt signaling and reinstate insulin sensitivity (FIG. 13I).

Cell-Permeant GIV-Derived Peptides can Effectively Reverse IR in Skeletal Muscle.

Figures 14A, 14B, 14C, 14D, 14E, 14F, 14G:
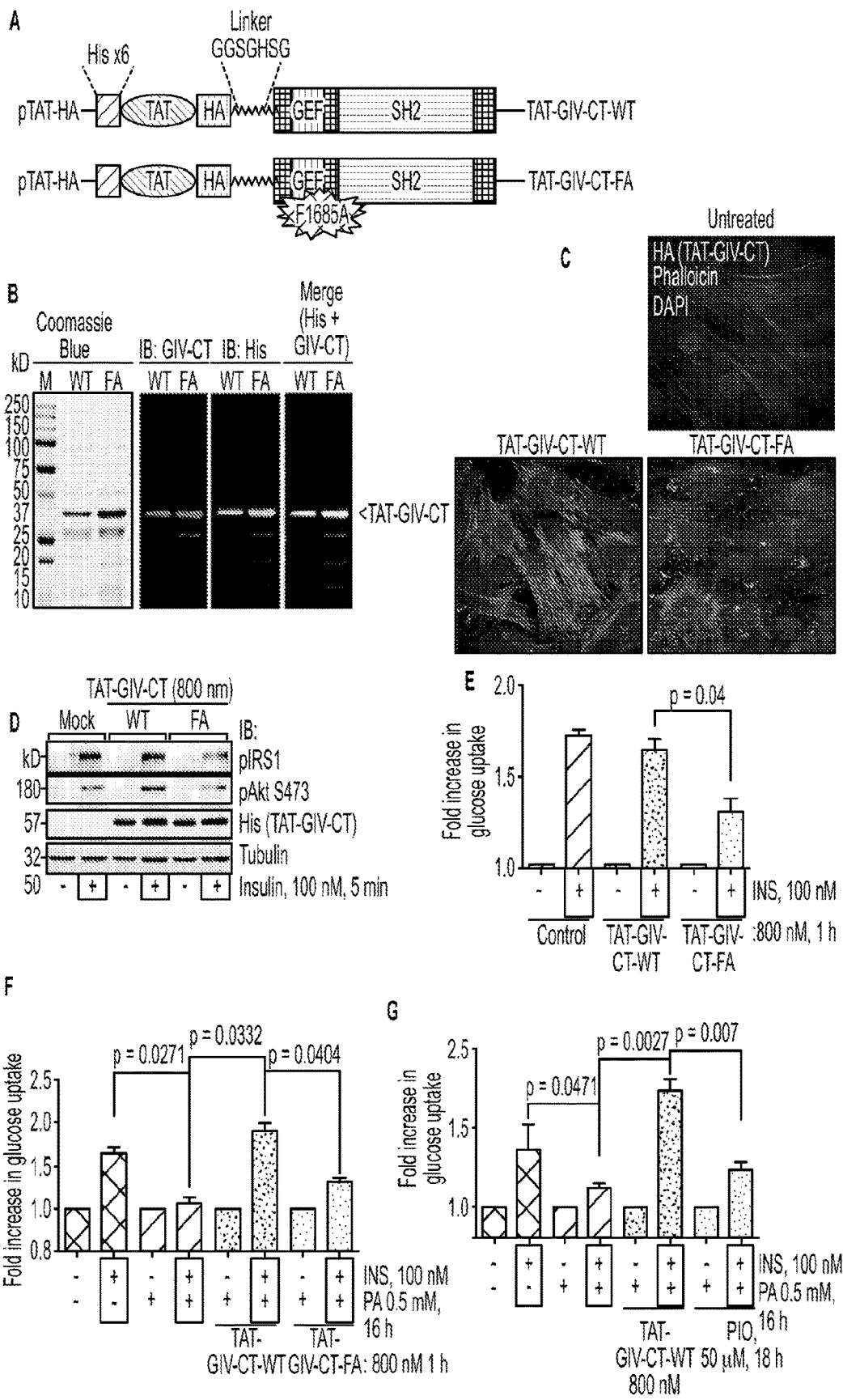
FIGS. 14A-14G. Cell-permeant TAT-GIV-CT-WT, but not FA mutant peptides can effectively reverse lipid-induced IR in skeletal muscles.

To investigate whether GIV-GEF can serve as a therapeutic target for exogenous modulation of IR, a recently validated recombinant, cell permeant TAT-tagged GIV-CT peptides (WT and GEF-deficient FA mutant peptides spanning GIV's GEF and SH2-like domains, FIGS. 14A-14B) was used. These peptides offer a non-genetic approach for exogenous manipulation of GIV-GEF-dependent signaling programs and cellular phenotypes in diverse cells and a variety of pathophysiologic processes (Ma et al, 2015). L6 myotubes homogeneously took up TAT-peptides HO % efficiency of uptake; FIG. 14C). Uptake of GIV-CT-WT peptides was associated with enhancement of stress-fiber formation and phosphorylation of IRS1 and Akt proteins in response to insulin (FIGS. 14C-14D). However, uptake of GIV-CT-FA peptides disrupted the actin stress fibers, as shown previously in other cell lines, and suppressed IRS1 and Akt phosphorylation in response to insulin. Consistent with these signaling programs, insulin-stimulated glucose uptake in the basal state was unaffected by GIV-CT-WT peptides, but was significantly inhibited by GIV-CT-FA peptides (FIG. 14E). GIV-CT-WT, but not the FA mutant peptides effectively reversed PA-induced IR (FIG. 14F), and ~800 nM of WT peptide was as effective as 50 μM Pio in reversing such IR (FIG. 14G). These studies demonstrate that cell-permeant GIV-CT peptides can enhance metabolic insulin signaling and reverse IR effectively in a GEF-dependent way.

Discussion

Figure 15:
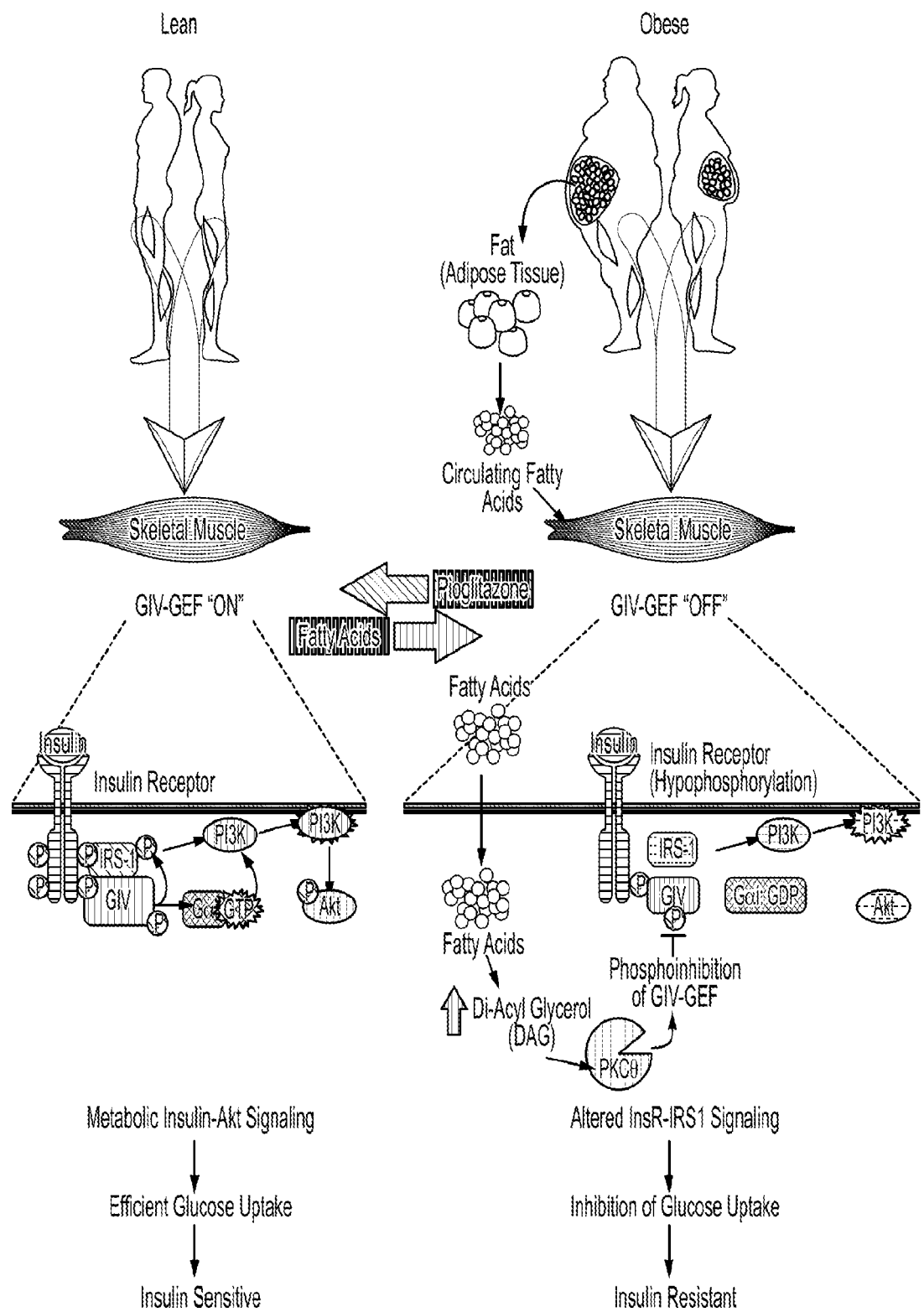
FIG. 15. Schematic summarizing how GIV-GEF is a pivotal node for metabolic insulin response in lean normals (left) and for lipid-induced IR in the obese (right). Left: In lean individuals, insulin triggers tyrosine phosphorylation and activation of GIV (pY1764), GIV's GEF function is "on" and Gαi is activated. Metabolic insulin signaling is enhanced through the InsR/IRS1/PI3K/Akt/AS160 signaling axis, resulting in efficient exocytosis of GSVs and rapid uptake of glucose. Right: In the obese, circulating free fatty-acids trigger the accumulation of diacyl glycerol (DAG) and PKCθ is activated. PKCθ phosphorylates GIV at S1689 and turns "off" its GEF function. Consequently, Gαi remains inactive and the InsR/IRS1/PI3K/Akt/AS160 signaling cascade is suppressed, thereby triggering IR.
Figures 16A, 16B, 16C, 16D:
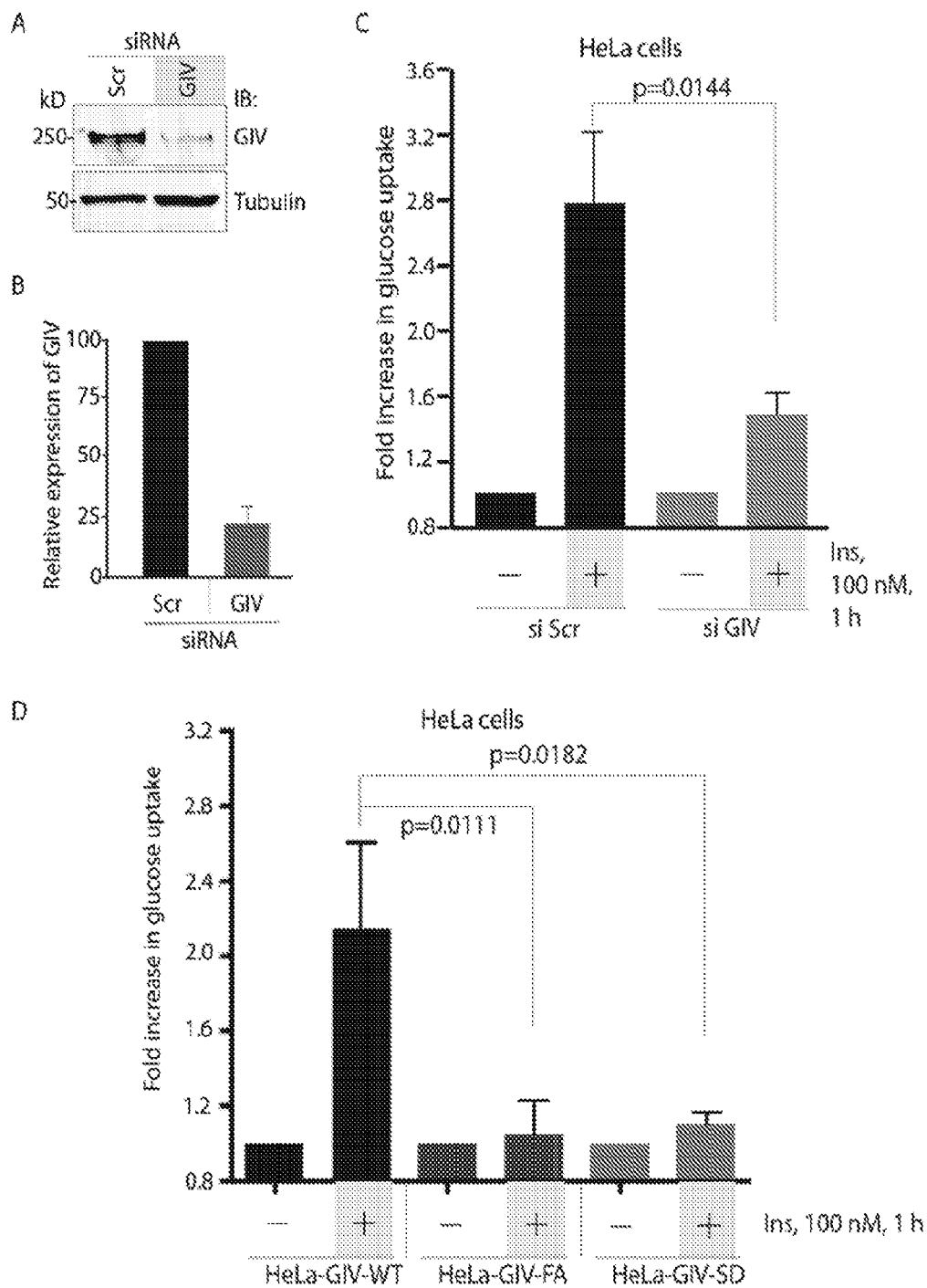
FIGS. 16A-16D. Activation of Gαi by GIV's GEF motif is essential for efficient GLUT4 exocytosis and glucose uptake.

Phosphoinhibition of GIV-GEF by PKCθ triggers lipid-induced insulin resistance; dephosphorylation of GIV-GEF reinstates insulin sensitivity, provided GIV-GEF plays a major role as a dominant conduit for insulin response in the skeletal muscle, and identification of key phosphoevents that allow this GEF to serve as a decisive pivot/node for cellular insulin response in physiology and disease (FIG. 15). In lean individuals, insulin triggers activation of GIV by tyrosine phosphorylation (pY), GIV's GEF function is turned "on" and Gαi is activated, metabolic insulin signaling is initiated through the InsR/IRS1/PI3K/Akt signaling axis, culminating in efficient exocytosis of GSVs and subsequent uptake of glucose. In the obese, circulating free fatty-acids trigger the accumulation of diacyl glycerol (DAG) and activation of PKCθ in skeletal muscle, which in turn phosphorylates GIV's GEF motif at S1689 and selectively turns "off" the GEF function. Consequently, Gαi remains inactive and a majority of the key elements of metabolic insulin signaling are suppressed, thereby triggering IR.

Reversible phosphorylation of GIV at S1689 by PKCθ, and the ability of this single phosphoevent to modulate the InsR-GIV-Gαi signaling axis is a critical determinant of cellular insulin responses. It was demonstrated that this phosphoevent alone is sufficient to mimic fatty-acid-induced IR and that fatty acids require such phosphorylation to induce IR. Although this study dissected the interplay between GIV and PKCθ in lipid-induced IR, because GIV can intercept signaling downstream of multiple classes of receptors (GPCRs and RTKs) and non-RTKs alike [reviewed in (Garcia-Marcos et al, 2015)], and is an enhancer of STAT3 as well as its transcriptional target (Dunkel et al, 2012), it my suggest that GIV is a central node for other major triggers of IR, i.e., inflammation, suppression of adiponectin, leptin resistance, etc, which also require activation of PKCθ (Anderson et al, 2006; Itani et al, 2000; Lin et al, 2000; Shulman, 2000) and/or the JAK-STAT3 pathway (Mashili et al, 2013; Wunderlich et al, 2013).

It was also shown that TZDs like Pioglitazone release the phosphoinhibition on GIV-GEF and restore its function. Such restoration was essential for TZD action because TZDs failed to reverse IR and reinstate insulin sensitivity in cells expressing the constitutively phosphomimic GIV-S1689D mutant. Because chronic TZD therapy does not suppress PKCθ (Markova et al, 2010), the reduction in levels of GIV phosphorylation at S1689 observed after TZD therapy is likely to be a consequence of dephosphorylation by one of the many S/T phosphatases that are activated by TZDs in a PPARγ-dependent manner (Altiok et al, 1997; Cho et al, 2006; Pugazhenthi & Khandelwal, 1998; Sharma et al, 2004). Regardless of the mechanism(s) involved, these results indicate that GIV is a major target of TZDs that can account, in part, for TZD action on skeletal muscle. It is concluded that reversible phosphorylation at S1689 and inhibition of the GEF function, via which GIV activates Gαi, serves as a molecular switch for flipping skeletal muscles between insulin-sensitive and resistant states. Because GIV specifically binds Gαi, and not Gαq/11 (Le-Niculescu et al, 2005), these findings do not account for the previously described role of yet another G protein, Gαq/11 in insulin response (Imamura et al, 1999).

GIV's GEF function modulates several tiers within the metabolic insulin signaling cascade. It was demonstrated that activation of Gαi by GIV impacts many tiers within the insulin signaling cascade and that phosphoinhibition of GIV's GEF function antagonizes them all. It was shown previously that GIV directly binds autophosphorylated cytoplasmic tails of ligand-activated InsR via its C-terminal SH2-like module (Lin et al, 2014). Both SH2-like module and GIV's GEF functions are critical for coupling of G proteins to ligand-activated InsR (Garcia-Marcos et al, 2011; Lin et al, 2014; Midde et al, 2015). Here, it was shown that at the level of the receptor, activation of Gαi via GIV's GEF motif is required for maximal autophosphorylation and activation of InsRβ and recruitment and phosphoactivation of its major substrate, IRS1. The sites of autophosphorylation on InsRβ that GIV enhanced, i.e., Y1150 and Y1151, are required for maximal activation of the InsRβ kinase (White et al, 1988), and a failure to activate InsRβ kinase in skeletal muscles has been implicated in IR (Goodyear et al, 1995; Maegawa et al, 1991; Nolan et al, 1994). Although it is unclear how activation of Gαi by GIV may enhance receptor autophosphorylation, it has been previously shown that activation of Gαi is implicated in the enhancement of InsR autophosphorylation (Kreuzer et al, 2004) and activation of Gαi by GIV's GEF function can similarly enhance autophosphorylation of yet another RTK, EGFR (Ghosh et al, 2010). In both instances, suppression of protein tyrosine phosphatases (PTPs) has been implicated as the mechanism for enhanced receptor autophosphorylation (Lin et al, 2014; Moxham & Malbon, 1996). Because GIV directly binds ligand-activated InsRβ (Lin et al, 2014) and triggers the formation of InsRβ-Gαi complexes at the PM, it suggests that the formation of such InsRβ-GIV-Gαi complexes suppresses the recruitment and/or activation of key PTPases. It is concluded that the GIV-Gαi axis enhances cellular insulin response by increasing Ins kinase activity and autophosphorylation, two upstream events in insulin signaling.

At the immediate post-receptor level, it is demonstrated that GIV binds and modulates the functions of IRS1. Activation of Gαi by GIV enhanced the recruitment of IRS1 to the ligand-activated receptors at the PM, triggered robust tyrosine phosphorylation at Y632 and Y941 on IRS1 and enhanced the formation of IRS1-p85α(PI3K) complexes. Unlike the ligand-dependent nature of InsRβ-GIV (current work) or InsRβ-IRS1 (Sun et al, 1991) interactions, the GIV-IRS1 interaction was constitutive and direct, and this binding involves the C-terminal region of GIV and the N-terminal region of IRS1. The latter contains a phosphotyrosine binding domain (PTB), which is responsible for the direct interaction of IRS1 with InsRβ (Eck et al, 1996). These findings of InsRβ-GIV-IRS1 complexes upon insulin stimulation suggest that GIV may bind IRS1 at a distinct site where the autophosphorylated cytoplasmic tail of InsRβ docks within the PTB. The enhanced recruitment of IRS1 to InsRβ in the presence of GIV suggests that GIV may serve as a signal amplifier at the immediate post-receptor level by facilitating the recruitment of more IRS1 adaptors per activated InsR. Due to recent experimental evidence that questions the exclusivity of IRS1 for InsRβ (Knowlden et al, 2008) and because GIV is capable of binding multiple RTKs (e.g., EGFR, PDGFR, VEGFR) (Lin et al, 2014; Lopez-Sanchez et al, 2014), suggesting that GIV provides the necessary molecular basis for IRS1 to serve as a common conduit for metabolic response observed downstream of receptors other than InsRβ.

Although the precise mechanism of GIV-IRS1 interaction remains uncertain, this interaction adds GIV to the lengthy list of proteins that IRS1 scaffolds within the insulin signaling cascade (White, 2006). The finding that GIV enhanced tyrosine phosphorylation of IRS1 is consistent with the concomitant increase in the kinase activity of InsRβ and enhanced recruitment of IRS1 to the PM, the latter is a pre-requisite for maximal tyrosine phosphorylation of IRS1 (Myers et al, 1995; Voliovitch et al, 1995). The studies presented here conclude that GIV is required for maximal PM-recruitment and tyrosine phosphorylation of IRS1, both key events implicated in metabolic insulin signaling via IRS1. In doing so, and by virtue of its ability to directly bind and bring together several other components of the metabolic insulin response (InsR, IRS1, G proteins, actin, PI3K, Akt) GIV serves as an integral hub at the immediate post-receptor which fine-tunes IRS1-dependent metabolic insulin signaling.

Further downstream, the PI3K-Akt signaling pathway was maximally enhanced in the presence of an intact GIV-GEF, and a major pathway downstream of Akt was triggered, i.e., phosphoinhibition of the Rab-GAP AS160. Prior studies have demonstrated that docking of GSVs at the PM requires activation of Rab proteins (Lansey et al, 2012; Miinea et al, 2005; Sun et al, 2010) in response to insulin (Bai et al, 2007). By triggering the phosphoinhibition of Rab-GAP AS160, GIV's GEF function is likely to affect the exocytosis of GSVs via potentiation of Rab GTPases. The studies presented in this example conclude that GIV functionally interacts with and enhances key signaling events that can also coordinate membrane trafficking within the insulin response cascade, and in doing so, it exemplifies a molecular basis for the observed engagement between these events during insulin-triggered glucose uptake into cells (Leto & Saltiel, 2012).

Although these studies have specifically dissected the role of GIV's GEF function in coordinating key signaling events that comprise the metabolic insulin response, it is notable that the GEF motif merely represents a ~30-35 aa stretch within a 1871 aa long, multimodular protein, which is comprised of several other key functional modules that may take part in other key aspects of glucose uptake. One such well-defined module is GIV's SH2-like domain, which is necessary and sufficient for GIV to directly bind autophosphorylated cytoplasmic tail of InsR; without a functional SH2-like domain, GIV can neither bind InsR, nor facilitate the formation of InsR-G protein complexes (Lin et al, 2014). Another such module, whose boundaries remain to be defined, but appears to be functionally distinct from the GEF module is a region within GIV's C-terminus that directly binds IRS1; it is possible that selective inhibition of GIV-IRS1 interaction may also impair the metabolic insulin response and glucose uptake. The recent findings that GIV regulates cargo trafficking from the ERGIC to the Golgi (Lo et al, 2015) raises the possibility that GIV may also play a role in regulating GLUT4 trafficking from the Golgi to GSVs. Additionally, GIV is also known to regulate clathrin-mediated endocytosis and endocytic trafficking (Beas et al, 2012; Weng et al, 2014), two processes that are closely intertwined with and key determinants of the kinetics of GLUT4 trafficking, glucose uptake and downregulation of insulin receptor signaling. Because the actin cytoskeleton has also been described as a tether for GSVs (Stockli et al, 2011), it is possible that another previously characterized module that enables GIV to remodel the cortical actin cytoskeleton further aids in GSV exocytosis and glucose uptake (Enomoto et al, 2005; Ghosh et al, 2010). Thus, it is likely that many of GIV's modules, and not just its C-terminal GEF motif may play a role in integrating signaling events with vesicular trafficking and cytoskeletal changes to orchestrate glucose uptake after insulin stimulation.

Selective modulation of GIV-GEF emerges as a therapeutic strategy for reversal of IR. It was found that cell-penetrable GIV peptides were as effective as TZDs in their ability to reverse fatty-acid-induced IR in a GEF-dependent way, and thus, activation of Gαi via GIV's GEF mimics the action and matches the potency of TZDs. Because postprandial lipotoxicity can also suppress GIV expression in skeletal muscles (FIGS. 20A-20D), these results using cell-permeant peptides suggest that replenishing GIV-CT (with active GEF) by gene therapy is a viable strategy for the treatment of IR. Other strategies include agonists of GIV's GEF function, antagonists of the inhibitory phosphoevent on GIV triggered by PKCθ, or activation of phosphatases that dephosphorylate GIV—all approaches that may serve as more refined, effective and precise therapeutic strategies to reverse IR in skeletal muscle. GIV expressed in adipocytes is also likely to enhance the metabolic insulin response in adipose tissue, the second major site of IR. However, phosphoinhibition of GIV-GEF by PKCθ is unlikely to be a trigger for IR because this kinase is undetectable in adipocytes (Fleming et al, 1998). Instead, mechanisms such as transcriptional repression, SNPs or post-translational modifications (splice variants) that reduce the levels of full length GIV may play a role. Further studies to determine how IR is triggered in adipocytes, and if the GIV-targeted approaches discussed above can reverse IR also in the adipose tissue are suggested.

REFERENCES

Altiok S, Xu M, Spiegelman BM (1997) PPARgamma induces cell cycle withdrawal: inhibition of E2F/DP DNA-binding activity via down-regulation of PP2A. *Genes & development* 11: 1987-1998.

Anderson K, Fitzgerald M, Dupont M, Wang T, Paz N, Dorsch M, Healy A, Xu Y, Ocain T, Schopf L, Jaffee B, Picarella D (2006) Mice deficient in PKC theta demonstrate impaired in vivo T cell activation and protection from T cell-mediated inflammatory diseases. *Autoimmunity* 39: 469-478.

Aroda V R, Ciaraldi T P, Burke P, Mudaliar S, Clopton P, Phillips S, Chang R J, Henry R R (2009) Metabolic and hormonal changes induced by pioglitazone in polycystic ovary syndrome: a randomized, placebo-controlled clinical trial. *The Journal of clinical endocrinology and metabolism* 94: 469-476.

Bai L, Wang Y, Fan J, Chen Y, Ji W, Qu A, Xu P, James D E, Xu T (2007) Dissecting multiple steps of GLUT4 trafficking and identifying the sites of insulin action. *Cell metabolism* 5: 47-57.

Beas A O, Taupin V, Teodorof C, Nguyen L T, Garcia-Marcos M, Farquhar M G (2012) Galphas promotes EEA1 endosome maturation and shuts down proliferative signaling through interaction with GIV (Girdin). *Molecular biology of the cell* 23: 4623-4634.

Carter A M (2005) Inflammation, thrombosis and acute coronary syndromes. *Diabetes & vascular disease research: official journal of the International Society of Diabetes and Vascular Disease* 2: 113-121.

Chen J F, Guo J H, Moxham C M, Wang H Y, Malbon C C (1997) Conditional, tissue-specific expression of Q205L G alpha i2 in vivo mimics insulin action. *J Mol Med (Berl)* 75: 283-289.

Cho D H, Choi Y J, Jo S A, Ryou J, Kim J Y, Chung J, Jo I (2006) Troglitazone acutely inhibits protein synthesis in endothelial cells via a novel mechanism involving protein phosphatase 2A-dependent p70 S6 kinase inhibition. *American journal of physiology Cell physiology* 291: C317-326.

Ciaraldi T P, Maisel A (1989) Role of guanine nucleotide regulatory proteins in insulin stimulation of glucose transport in rat adipocytes. Influence of bacterial toxins. *The Biochemical journal* 264: 389-396.

Dawson, K., Aviles-Hernandez, A., Cushman, S. W., and Malide, D. (2001). Insulin-regulated trafficking of dual-labeled glucose transporter 4 in primary rat adipose cells. Biochemical and biophysical research communications 287, 445-454.

Dunkel Y, Ong A, Notani D, Mittal Y, Lam M, Mi X, Ghosh P (2012) STAT3 protein up-regulates Galpha-interacting vesicle-associated protein (GIV)/Girdin expression, and GIV enhances STAT3 activation in a positive feedback loop during wound healing and tumor invasion/metastasis. *The Journal of biological chemistry* 287: 41667-41683.

Eck M J, Dhe-Paganon S, Trub T, Nolte R T, Shoelson S E (1996) Structure of the IRS-1 PTB domain bound to the juxtamembrane region of the insulin receptor. *Cell* 85: 695-705.

Enomoto A, Murakami H, Asai N, Morone N, Watanabe T, Kawai K, Murakumo Y, Usukura J, Kaibuchi K, Takahashi M (2005) Akt/PKB regulates actin organization and cell motility via Girdin/APE. *Developmental cell* 9: 389-402.

Fleming I, MacKenzie S J, Vernon R G, Anderson N G, Houslay M D, Kilgour E (1998) Protein kinase C isoforms play differential roles in the regulation of adipocyte differentiation. *The Biochemical journal* 333 (Pt 3): 719-727.

Flores-Riveros J R, Sibley E, Kastelic T, Lane M D (1989) Substrate phosphorylation catalyzed by the insulin receptor tyrosine kinase. Kinetic correlation to autophosphorylation of specific sites in the beta subunit. *The Journal of biological chemistry* 264: 21557-21572.

Garcia-Marcos, M., Kietrsunthorn, P. S., Pavlova, Y., Adia, M. A., Ghosh, P., and Farquhar, M. G. (2012). Functional characterization of the guanine nucleotide exchange factor (GEF) motif of GIV protein reveals a threshold effect in signaling. Proceedings of the National Academy of Sciences of the United States of America 109, 1961-1966.

Garcia-Marcos M, Ear J, Farquhar M G, Ghosh P (2011) A GDI (AGS3) and a GEF (GIV) regulate autophagy by balancing G protein activity and growth factor signals. *Molecular biology of the cell* 22: 673-686.

Garcia-Marcos M, Ghosh P, Ear J, Farquhar M G (2010) A structural determinant that renders G alpha(i) sensitive to activation by GIV/girdin is required to promote cell migration. *The Journal of biological chemistry* 285: 12765-12777.

Garcia-Marcos M, Ghosh P, Farquhar M G (2009) GIV is a nonreceptor GEF for G alpha i with a unique motif that regulates Akt signaling. *Proc Natl Acad Sci USA* 106: 3178-3183.

Garcia-Marcos M, Ghosh P, Farquhar M G (2015) GIV/Girdin transmits signals from multiple receptors by triggering trimeric G protein activation. *The Journal of biological chemistry* 290: 6697-6704.

Ghosh P, Beas A O, Bornheimer S J, Garcia-Marcos M, Forry E P, Johannson C, Ear J, Jung B H, Cabrera B, Carethers J M, Farquhar M G (2010) A G{alpha}i-GIV molecular complex binds epidermal growth factor receptor and determines whether cells migrate or proliferate. *Molecular biology of the cell* 21: 2338-2354.

Ghosh P, Garcia-Marcos M, Bornheimer S J, Farquhar M G (2008) Activation of Galphai3 triggers cell migration via regulation of GIV. *J Cell Biol* 182: 381-393.

Gohla A, Klement K, Nurnberg B (2007) The heterotrimeric G protein G(i3) regulates hepatic autophagy downstream of the insulin receptor. *Autophagy* 3: 393-395.

Goodyear L J, Giorgino F, Sherman L A, Carey J, Smith R J, Dohm G L (1995) Insulin receptor phosphorylation, insulin receptor substrate-1 phosphorylation, and phosphatidylinositol 3-kinase activity are decreased in intact skeletal muscle strips from obese subjects. *The Journal of clinical investigation* 95: 2195-2204.

Griffin M E, Marcucci M J, Cline G W, Bell K, Barucci N, Lee D, Goodyear L J, Kraegen E W, White M F, Shulman G I (1999) Free fatty acid-induced insulin resistance is associated with activation of protein kinase C theta and alterations in the insulin signaling cascade. *Diabetes* 48: 1270-1274.

Haasch D, Berg C, Clampit J E, Pederson T, Frost L, Kroeger P, Rondinone C M (2006) PKCtheta is a key player in the development of insulin resistance. *Biochemical and biophysical research communications* 343: 361-368.

Haga, Y., Ishii, K., and Suzuki, T. (2011). N-glycosylation is critical for the stability and intracellular trafficking of glucose transporter GLUT4. The Journal of biological chemistry 286, 31320-31327.

Hartung A, Ordelheide A M, Staiger H, Melzer M, Haring H U, Lammers R (2013) The Akt substrate Girdin is a regulator of insulin signaling in myoblast cells. *Biochimica et biophysica acta* 1833: 2803-2811.

Hoehn K L, Hohnen-Behrens C, Cederberg A, Wu L E, Turner N, Yuasa T, Ebina Y, James D E (2008) IRS1-independent defects define major nodes of insulin resistance. *Cell metabolism* 7: 421-433.

Huang B, Babcock H, Zhuang X (2010) Breaking the diffraction barrier: super-resolution imaging of cells. *Cell* 143: 1047-1058.

Hwang H, Bowen B P, Lefort N, Flynn C R, De Filippis E A, Roberts C, Smoke C C, Meyer C, Hojlund K, Yi Z, Mandarino L J (2010) Proteomics analysis of human skeletal muscle reveals novel abnormalities in obesity and type 2 diabetes. *Diabetes* 59: 33-42.

Imamura T, Vollenweider P, Egawa K, Clodi M, Ishibashi K, Nakashima N, Ugi S, Adams J W, Brown J H, Olefsky J M (1999) G alpha-q/11 protein plays a key role in insulin-induced glucose transport in 3T3-L1 adipocytes. *Molecular and cellular biology* 19: 6765-6774.

Itani S I, Zhou Q, Portes W J, MacDonald K G, Dohm G L (2000) Involvement of protein kinase C in human skeletal muscle insulin resistance and obesity. *Diabetes* 49: 1353-1358.

Jans, A., Konings, E., Goossens, G. H., Bouwman, F. G., Moors, C. C., Boekschoten, M. V., Afman, L. A., Muller, M., Mariman, E. C., and Blaak, E. E. (2012). PUFAs acutely affect triacylglycerol-derived skeletal muscle fatty acid uptake and increase postprandial insulin sensitivity. The American journal of clinical nutrition 95, 825-836.

Kahn B B, Flier J S (2000) Obesity and insulin resistance. *The Journal of clinical investigation* 106: 473-481.

Kanoh Y, Ishizuka T, Morita H, Ishizawa M, Miura A, Kajita K, Kimura M, Suzuki T, Sakuma H, Yasuda K (2000) Effect of pertussis toxin on insulin-induced signal transduction in rat adipocytes and soleus muscles. *Cellular signalling* 12: 223-232.

Kim J K, Fillmore J J, Sunshine M J, Albrecht B, Higashimori T, Kim D W, Liu Z X, Soos T J, Cline G W, O'Brien W R, Littman D R, Shulman G I (2004) PKC-theta knockout mice are protected from fat-induced insulin resistance. *The Journal of clinical investigation* 114: 823-827.

Kim, J. A., Yeh, D. C., Ver, M., Li, Y., Carranza, A., Conrads, T. P., Veenstra, T. D., Harrington, M. A., and Quon, M. J. (2005). Phosphorylation of Ser24 in the pleckstrin homology domain of insulin receptor substrate-1 by Mouse Pelle-like kinase/interleukin-1 receptor-associated kinase: cross-talk between inflammatory signaling and insulin signaling that may contribute to insulin resistance. The Journal of biological chemistry 280, 23173-23183.

Knowlden J M, Jones H E, Barrow D, Gee J M, Nicholson R I, Hutcheson I R (2008) Insulin receptor substrate-1 involvement in epidermal growth factor receptor and insulin-like growth factor receptor signalling: implication for Gefitinib ('Iressa') response and resistance. *Breast cancer research and treatment* 111: 79-91.

Kreuzer J, Nurnberg B, Krieger-Brauer H I (2004) Ligand-dependent autophosphorylation of the insulin receptor is positively regulated by Gi-proteins. *The Biochemical journal* 380: 831-836.

Krook A, Moller D E, Dib K, O'Rahilly S (1996) Two naturally occurring mutant insulin receptors phosphorylate insulin receptor substrate-1 (IRS-1) but fail to mediate the biological effects of insulin. Evidence that IRS-1 phosphorylation is not sufficient for normal insulin action. *The Journal of biological chemistry* 271: 7134-7140.

Krupinski J, Rajaram R, Lakonishok M, Benovic J L, Cerione R A (1988) Insulin-dependent phosphorylation of GTP-binding proteins in phospholipid vesicles. *The Journal of biological chemistry* 263: 12333-12341.

Lansey M N, Walker N N, Hargett S R, Stevens J R, Keller S R (2012) Deletion of Rab GAP AS160 modifies glucose uptake and GLUT4 translocation in primary skeletal muscles and adipocytes and impairs glucose homeostasis. *American journal of physiology Endocrinology and metabolism* 303: E1273-1286.

Le-Niculescu H, Niesman I, Fischer T, DeVries L, Farquhar M G (2005) Identification and characterization of GIV, a novel Galpha i/s-interacting protein found on COPI, endoplasmic reticulum-Golgi transport vesicles. *The Journal of biological chemistry* 280: 22012-22020.

Le Roith D, Zick Y (2001) Recent advances in our understanding of insulin action and insulin resistance. *Diabetes care* 24: 588-597.

Leto D, Saltiel A R (2012) Regulation of glucose transport by insulin: traffic control of GLUT4. *Nature reviews Molecular cell biology* 13: 383-396.

Li Y, Soos T J, Li X, Wu J, Degennaro M, Sun X, Littman D R, Birnbaum M J, Polakiewicz R D (2004) Protein kinase C Theta inhibits insulin signaling by phosphorylating IRS1 at Ser(1101). *The Journal of biological chemistry* 279: 45304-45307.

Lin C, Ear J, Midde K, Lopez-Sanchez I, Aznar N, Garcia-Marcos M, Kufareva I, Abagyan R, Ghosh P (2014) Structural basis for activation of trimeric Gi proteins by multiple growth factor receptors via GIV/Girdin. *Molecular biology of the cell.*

Lin C, Ear J, Pavlova Y, Mittal Y, Kufareva I, Ghassemian M, Abagyan R, Garcia-Marcos M, Ghosh P (2011) Tyrosine phosphorylation of the Galpha-interacting protein GIV promotes activation of phosphoinositide 3-kinase during cell migration. *Sci Signal* 4: ra64.

Lin X, O'Mahony A, Mu Y, Geleziunas R, Greene W C (2000) Protein kinase C-theta participates in NF-kappaB activation induced by CD3-CD28 costimulation through selective activation of IkappaB kinase beta. *Molecular and cellular biology* 20: 2933-2940.

Lo I C, Gupta V, Midde K K, Taupin V, Lopez-Sanchez I, Kufareva I, Abagyan R, Randazzo P A, Farquhar M G, Ghosh P (2015) Activation of Galphai at the Golgi by GIV/Girdin imposes finiteness in Arf1 signaling. *Developmental cell* 33: 189-203.

Lopez-Sanchez I, Dunkel Y, Roh Y S, Mittal Y, De Minicis S, Muranyi A, Singh S, Shanmugam K, Aroonsakool N, Murray F, Ho S B, Seki E, Brenner D A, Ghosh P (2014) GIV/Girdin is a central hub for profibrogenic signalling networks during liver fibrosis. *Nat Commun* 5: 4451.

Lopez-Sanchez I, Garcia-Marcos M, Mittal Y, Aznar N, Farquhar M G, Ghosh P (2013) Protein kinase C-theta (PKCtheta) phosphorylates and inhibits the guanine exchange factor, GIV/Girdin. *Proc Natl Acad Sci USA* 110: 5510-5515.

Lovejoy, J. C. (2002). The influence of dietary fat on insulin resistance. Current diabetes reports 2, 435-440.

Ma G, Aznar N, Kangrioloulos N, Midde K, Lopez-Sanchez I, Dunkel Y, Sato E., R. G, Ghosh P (2015) Therapeutic Effects of Cell-Permeant GIV peptides that Activate G Proteins downstream of Growth Factors. Accepted, In press, *PNAS*.

Maegawa H, Shigeta Y, Egawa K, Kobayashi M (1991) Impaired autophosphorylation of insulin receptors from abdominal skeletal muscles in nonobese subjects with NIDDM. *Diabetes* 40: 815-819.

Markova I, Zidek V, Musilova A, Simakova M, Mlejnek P, Kazdova L, Pravenec M (2010) Long-term pioglitazone treatment augments insulin sensitivity and PKC-epsilon and PKC-theta activation in skeletal muscles in sucrose fed rats. *Physiological research/Academia Scientiarum Bohemoslovaca* 59: 509-516.

Mashili F, Chibalin A V, Krook A, Zierath J R (2013) Constitutive STAT3 phosphorylation contributes to skeletal muscle insulin resistance in type 2 diabetes. *Diabetes* 62: 457-465.

Midde K K, Aznar N, Laederich M B, Ma G S, Kunkel M T, Newton A C, Ghosh P (2015) Multimodular biosensors reveal a novel platform for activation of G proteins by growth factor receptors. *Proc Natl Acad Sci USA* 112: E937-946.

Miinea C P, Sano H, Kane S, Sano E, Fukuda M, Peranen J, Lane W S, Lienhard G E (2005) AS160, the Akt substrate regulating GLUT4 translocation, has a functional Rab GTPase-activating protein domain. *The Biochemical journal* 391: 87-93.

Moxham C M, Malbon C C (1996) Insulin action impaired by deficiency of the G-protein subunit G ialpha2. *Nature* 379: 840-844.

Myers M G, Jr., Grammer T C, Brooks J, Glasheen E M, Wang L M, Sun X J, Blenis J, Pierce J H, White M F (1995) The pleckstrin homology domain in insulin receptor substrate-1 sensitizes insulin signaling. *The Journal of biological chemistry* 270: 11715-11718.

Nagahara, H., Vocero-Akbani, A. M., Snyder, E. L., Ho, A., Latham, D. G., Lissy, N. A., Becker-Hapak, M., Ezhevsky, S. A., and Dowdy, S. F. (1998). Transduction of full-length TAT fusion proteins into mammalian cells: TAT-p27Kip1 induces cell migration. Nature medicine 4, 1449-1452.

Nolan J J, Freidenberg G, Henry R, Reichart D, Olefsky J M (1994) Role of human skeletal muscle insulin receptor kinase in the in vivo insulin resistance of noninsulin-dependent diabetes mellitus and obesity. *The Journal of clinical endocrinology and metabolism* 78: 471-477.

O'Brien R M, Houslay M D, Milligan G, Siddle K (1987) The insulin receptor tyrosyl kinase phosphorylates holomeric forms of the guanine nucleotide regulatory proteins Gi and Go. *FEBS letters* 212: 281-288.

Pessin J E, Saltiel A R (2000) Signaling pathways in insulin action: molecular targets of insulin resistance. *The Journal of clinical investigation* 106: 165-169.

Pugazhenthi S, Khandelwal R L (1998) Insulin action on protein phosphatase-1 activation is enhanced by the antidiabetic agent pioglitazone in cultured diabetic hepatocytes. *Molecular and cellular biochemistry* 182: 185-191.

Qiao, L. Y., Goldberg, J. L., Russell, J. C., and Sun, X. J. (1999). Identification of enhanced serine kinase activity in insulin resistance. The Journal of biological chemistry 274, 10625-10632.

Roszik, J., Lisboa, D., Szollosi, J., and Vereb, G. (2009). Evaluation of intensity-based ratiometric FRET in image cytometry—approaches and a software solution. Cytometry Part A: the journal of the International Society for Analytical Cytology 75, 761-767.

Rothenberg P L, Kahn C R (1988) Insulin inhibits pertussis toxin-catalyzed ADP-ribosylation of G-proteins. Evidence for a novel interaction between insulin receptors and G-proteins. *The Journal of biological chemistry* 263: 15546-15552.

Rundek T, Gardener H, Xu Q, Goldberg R B, Wright C B, Boden-Albala B, Disla N, Paik M C, Elkind M S, Sacco R L (2010) Insulin resistance and risk of ischemic stroke among nondiabetic individuals from the northern Manhattan study. *Archives of neurology* 67: 1195-1200.

Sakurai-Yageta, M., Recchi, C., Le Dez, G., Sibarita, J. B., Daviet, L., Camonis, J., D'Souza-Schorey, C., and Chavrier, P. (2008). The interaction of IQGAP1 with the exocyst complex is required for tumor cell invasion downstream of Cdc42 and RhoA. The Journal of cell biology 181, 985-998.

Saltiel A R, Kahn C R (2001) Insulin signalling and the regulation of glucose and lipid metabolism. *Nature* 414: 799-806.

Sato M, Ozawa T, Inukai K, Asano T, Umezawa Y (2002) Fluorescent indicators for imaging protein phosphorylation in single living cells. *Nature biotechnology* 20: 287-294.

Schmitz-Peiffer C, Browne C L, Oakes N D, Watkinson A, Chisholm D J, Kraegen E W, Biden T J (1997) Alterations in the expression and cellular localization of protein kinase C isozymes epsilon and theta are associated with insulin resistance in skeletal muscle of the high-fat-fed rat. *Diabetes* 46: 169-178.

Sharma C, Pradeep A, Pestell R G, Rana B (2004) Peroxisome proliferator-activated receptor gamma activation modulates cyclin D1 transcription via beta-catenin-independent and cAMP-response element-binding protein-dependent pathways in mouse hepatocytes. *The Journal of biological chemistry* 279: 16927-16938.

Shulman G I (2000) Cellular mechanisms of insulin resistance. *The Journal of clinical investigation* 106: 171-176.

Song X, Zheng X, Malbon C C, Wang H (2001) Galpha i2 enhances in vivo activation of and insulin signaling to GLUT4. *The Journal of biological chemistry* 276: 34651-34658.

Stockli J, Fazakerley D J, James D E (2011) GLUT4 exocytosis. *Journal of cell science* 124: 4147-4159.

Studier, F. W. (2005). Protein production by auto-induction in high density shaking cultures. Protein expression and purification 41, 207-234.

Sun X J, Rothenberg P, Kahn C R, Backer J M, Araki E, Wilden P A, Cahill D A, Goldstein B J, White M F (1991) Structure of the insulin receptor substrate IRS-1 defines a unique signal transduction protein. *Nature* 352: 73-77.

Sun Y, Bilan P J, Liu Z, Klip A (2010) Rab8A and Rab13 are activated by insulin and regulate GLUT4 translocation in muscle cells. *Proc Natl Acad Sci USA* 107: 19909-19914.

Taniguchi C M, Emanuelli B, Kahn C R (2006) Critical nodes in signalling pathways: insights into insulin action. *Nature reviews Molecular cell biology* 7: 85-96.

Thorburn A W, Gumbiner B, Bulacan F, Wallace P, Henry R R (1990) Intracellular glucose oxidation and glycogen synthase activity are reduced in non-insulin-dependent (type II) diabetes independent of impaired glucose uptake. *The Journal of clinical investigation* 85: 522-529.

Uhlen M, Oksvold P, Fagerberg L, Lundberg E, Jonasson K, Forsberg M, Zwahlen M, Kampf C, Wester K, Hober S, Wernerus H, Bjorling L, Ponten F (2010) Towards a knowledge-based Human Protein Atlas. *Nature biotechnology* 28: 1248-1250.

Voliovitch H, Schindler D G, Hadari Y R, Taylor S I, Accili D, Zick Y (1995) Tyrosine phosphorylation of insulin receptor substrate-1 in vivo depends upon the presence of its pleckstrin homology region. *The Journal of biological chemistry* 270: 18083-18087.

Weng L, Enomoto A, Miyoshi H, Takahashi K, Asai N, Morone N, Jiang P, An J, Kato T, Kuroda K, Watanabe T, Asai M, Ishida-Takagishi M, Murakumo Y, Nakashima H, Kaibuchi K, Takahashi M (2014) Regulation of cargo-selective endocytosis by dynamin 2 GTPase-activating protein girdin. *EMBO J* 33: 2098-2112.

White M F (2006) Regulating insulin signaling and beta-cell function through IRS proteins. *Canadian journal of physiology and pharmacology* 84: 725-737.

White M F, Shoelson S E, Keutmann H, Kahn C R (1988) A cascade of tyrosine autophosphorylation in the beta-subunit activates the phosphotransferase of the insulin receptor. *The Journal of biological chemistry* 263: 2969-2980.

Wunderlich C M, Hovelmeyer N, Wunderlich F T (2013) Mechanisms of chronic JAK-STAT3-SOCS3 signaling in obesity. *Jak-Stat* 2: e23878.

Xiong, X., Xu, Q., Huang, Y., Singh, R. D., Anderson, R., Leof, E., Hu, J., and Ling, K. (2012). An association between type Igamma PI4P 5-kinase and Exo70 directs E-cadherin clustering and epithelial polarization. *Molecular biology of the cell* 23, 87-98.

Yamamoto N, Sato T, Kawasaki K, Murosaki S, Yamamoto Y (2006) A nonradioisotope, enzymatic assay for 2-deoxyglucose uptake in L6 skeletal muscle cells cultured in a 96-well microplate. *Analytical biochemistry* 351: 139-145.

Yu C, Chen Y, Cline G W, Zhang D, Zong H, Wang Y, Bergeron R, Kim J K, Cushman S W, Cooney G J, Atcheson B, White M F, Kraegen E W, Shulman G I (2002) Mechanism by which fatty acids inhibit insulin activation of insulin receptor substrate-1 (IRS-1)-associated phosphatidylinositol 3-kinase activity in muscle. *The Journal of biological chemistry* 277: 50230-50236

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A cell-permeable peptide PTD-GIV-CT comprising (i) a peptide transduction domain (PTD) and (ii) a C-terminus of Gα-Interacting Vesicle associated protein (GIV-CT) or a mutant thereof, wherein said peptide is capable of activating Gi downstream of receptor tyrosine kinases (RTKs), wherein the PTD is connected to the GIV-CT via a linker sequence, and wherein the linker sequence comprises the sequence GGSGHSG (SEQ ID NO: 11).

2. The peptide of claim 1, wherein said peptide is capable of activating Gαi by enhancing nucleotide release via its GEF motif and interact with ligand-activated RTKs via its SH2-like motif.

3. The peptide of claim 1, wherein said peptide is capable of selectively affecting the activation of Gαi1/2/3, but not Gαo.

4. The peptide of claim 1, wherein said peptide is capable of inhibiting Gi downstream of receptor tyrosine kinases (RTKs).

5. The peptide of claim 1, wherein the PTD comprises TAT PTD sequence YGRKKRRQRRR (SEQ ID NO: 4).

6. The peptide of claim 1, wherein the PTD comprises the sequence selected from the group consisting of YARKARRQARR (SEQ ID NO: 5), YARAAARQARA (SEQ ID NO: 6), YARAARRAARR (SEQ ID NO: 7), YARAARRAARA (SEQ ID NO: 8), YARRRRRRRRR (SEQ ID NO: 9), and YAAARRRRRRR (SEQ ID NO: 10).

7. The peptide of claim 1, wherein said peptide further comprises a detection tag sequence.

8. The peptide of claim 7, wherein the detection tag sequence is hemagglutinin (HA) tag.

9. The peptide of claim 1, wherein said peptide further comprises a purification tag sequence.

10. The peptide of claim 9, wherein the purification tag sequence is hexa-histidine (His6) tag.

11. The peptide of claim 1, wherein GIV-CT comprises the sequence corresponding to amino acids 1660-1870 of human GIV protein.

12. The peptide of claim 1, wherein GIV-CT comprises the sequence corresponding to amino acids 1660-1870 of human GIV protein, wherein Ser-1675 is replaced by Asp (S1675D).

13. The peptide of claim 1, wherein GIV-CT comprises the sequence corresponding to amino acids 1660-1870 of human GIV protein, wherein Ser-1689 is replaced by Ala (S1689A).

14. The peptide of claim 1, wherein GIV-CT comprises the sequence corresponding to amino acids 1660-1870 of human GIV protein, wherein Phe-1685 is replaced by Ala (F1685A).

15. The peptide of claim 1, wherein GIV-CT comprises the sequence corresponding to amino acids 1660-1870 of human GIV protein, wherein Ser-1689 is replaced by Asp (S1689D).

16. The peptide of claim 1, wherein GIV-CT comprises the sequence corresponding to amino acids 1660-1870 of human GIV protein, wherein Ser-1675 is replaced by Ala (S1675A).

17. The peptide of claim 1, wherein GIV-CT comprises the sequence corresponding to amino acids 1660-1870 of human GIV protein, wherein Tyr-1764 and Tyr-1798 are replaced by Phe (Y1764F, Y1798F).

18. A pharmaceutical composition comprising the peptide of claim 1.

19. A method for modulating a GIV-dependent cellular signaling pathway in a cell, comprising administering to the cell an effective amount of the peptide of claim 1.

20. The method of claim 19, wherein said GIV-dependent cellular signaling pathway is PTK-Gi pathway for G protein activation.

21. The method of claim 19, wherein the cell is in a subject.

22. A method for enhancing wound healing in a subject in need thereof, comprising administering to said subject an effective amount of the peptide of claim 1.

23. The method of claim 22, wherein said peptide is administered topically to the wound.

24. The method of claim 22, wherein the peptide enhances epithelial cell migration into the wound and/or myofibroblast activation and/or collagen production in the wound.

25. A method for treating insulin resistance (IR) in a subject in need thereof, comprising administering to the subject an effective amount of the peptide of claim 1.

26. A method for enhancing metabolic insulin signaling in a subject comprising administering to the subject an effective amount of the peptide of claim 1, wherein the subject is suffering from a disease selected from the group consisting of obesity, glucose intolerance, hypertension, dyslipidemia, endothelial dysfunction, atherosclerotic CVD, hyperinsulinemia, type II diabetes, metabolic syndrome, and polycystic ovarian syndrome (PCOS).

27. A method for inhibiting tumor metastasis in a subject in need thereof, comprising administering to the subject an effective amount of the peptide of claim 1.

28. A method for treating a tissue fibrotic disease in a subject in need thereof comprising administering to the subject an effective amount of the peptide of claim 1.

29. The method of claim 28, wherein the fibrotic disease is selected from the group consisting of liver cirrhosis, liver fibrosis, non-alcoholic fatty liver disease (NAFLD), non-alcoholic steatohepatitis (NASH), alcoholic fatty liver disease, alcoholic steatohepatitis, hepatic steatosis, skeletal muscle fibrosis, skin fibrosis, scleroderma, skin fibrosis secondary to burns, keloids, hypertrophic post-surgical wounds, renal fibrosis, glomerulosclerosis, interstitial-tubular fibrosis, esophageal or gastro-intestinal fibrosis, bone marrow fibrosis, myelodysplastic syndrome, pulmonary fibrosis, peritoneal fibrosis, pancreatic fibrosis, post-radiation fibrosis, cardiac fibrosis and remodeling after myocardial infarction, brain fibrosis secondary to ischemia or infarcts, post-traumatic brain fibrosis, post-traumatic muscle fibrosis, and synovial/joint fibrosis.

* * * * *

SEQUENCE LISTING

```
<160> NUMBER OF SEQ ID NOS: 15

<210> SEQ ID NO 1
<211> LENGTH: 1870
<212> TYPE: PRT
<213> ORGANISM: Homo sapiens

<400> SEQUENCE: 1

Met Glu Asn Glu Ile Phe Thr Pro Leu Leu Glu Gln Phe Met Thr Ser
1               5                   10                  15

Pro Leu Val Thr Trp Val Lys Thr Phe Gly Pro Leu Ala Ala Gly Asn
            20                  25                  30

Gly Thr Asn Leu Asp Glu Tyr Val Ala Leu Val Asp Gly Val Phe Leu
        35                  40                  45

Asn Gln Val Met Leu Gln Ile Asn Pro Lys Leu Glu Ser Gln Arg Val
    50                  55                  60

Asn Lys Lys Val Asn Asn Asp Ala Ser Leu Arg Met His Asn Leu Ser
65                  70                  75                  80

Ile Leu Val Arg Gln Ile Lys Phe Tyr Tyr Gln Glu Thr Leu Gln Gln
                85                  90                  95

Leu Ile Met Met Ser Leu Pro Asn Val Leu Ile Ile Gly Lys Asn Pro
            100                 105                 110

Phe Ser Glu Gln Gly Thr Glu Glu Val Lys Lys Leu Leu Leu Leu Leu
        115                 120                 125

Leu Gly Cys Ala Val Gln Cys Gln Lys Lys Glu Glu Phe Ile Glu Arg
    130                 135                 140

Ile Gln Gly Leu Asp Phe Asp Thr Lys Ala Ala Val Ala Ala His Ile
145                 150                 155                 160
```

```
Gln Glu Val Thr His Asn Gln Glu Asn Val Phe Asp Leu Gln Trp Met
                165                 170                 175

Glu Val Thr Asp Met Ser Gln Glu Asp Ile Glu Pro Leu Leu Lys Asn
            180                 185                 190

Met Ala Leu His Leu Lys Arg Leu Ile Asp Glu Arg Asp Glu His Ser
        195                 200                 205

Glu Thr Ile Ile Glu Leu Ser Glu Glu Arg Asp Gly Leu His Phe Leu
    210                 215                 220

Pro His Ala Ser Ser Ala Gln Ser Pro Cys Gly Ser Pro Gly Met
225                 230                 235                 240

Lys Arg Thr Glu Ser Arg Gln His Leu Ser Val Glu Leu Ala Asp Ala
                245                 250                 255

Lys Ala Lys Ile Arg Arg Leu Arg Gln Glu Leu Glu Glu Lys Thr Glu
            260                 265                 270

Gln Leu Leu Asp Cys Lys Gln Glu Leu Glu Gln Met Glu Ile Glu Leu
        275                 280                 285

Lys Arg Leu Gln Gln Glu Asn Met Asn Leu Leu Ser Asp Ala Arg Ser
    290                 295                 300

Ala Arg Met Tyr Arg Asp Glu Leu Asp Ala Leu Arg Glu Lys Ala Val
305                 310                 315                 320

Arg Val Asp Lys Leu Glu Ser Glu Val Ser Arg Tyr Lys Glu Arg Leu
                325                 330                 335

His Asp Ile Glu Phe Tyr Lys Ala Arg Val Glu Glu Leu Lys Glu Asp
            340                 345                 350

Asn Gln Val Leu Leu Glu Thr Lys Thr Met Leu Glu Asp Gln Leu Glu
        355                 360                 365

Gly Thr Arg Ala Arg Ser Asp Lys Leu His Glu Leu Glu Lys Glu Asn
    370                 375                 380

Leu Gln Leu Lys Ala Lys Leu His Asp Met Glu Met Glu Arg Asp Met
385                 390                 395                 400

Asp Arg Lys Lys Ile Glu Glu Leu Met Glu Glu Asn Met Thr Leu Glu
                405                 410                 415

Met Ala Gln Lys Gln Ser Met Asp Glu Ser Leu His Leu Gly Trp Glu
            420                 425                 430

Leu Glu Gln Ile Ser Arg Thr Ser Glu Leu Ser Glu Ala Pro Gln Lys
        435                 440                 445

Ser Leu Gly His Glu Val Asn Glu Leu Thr Ser Ser Arg Leu Leu Lys
    450                 455                 460

Leu Glu Met Glu Asn Gln Ser Leu Thr Lys Thr Val Glu Glu Leu Arg
465                 470                 475                 480

Thr Thr Val Asp Ser Val Glu Gly Asn Ala Ser Lys Ile Leu Lys Met
                485                 490                 495

Glu Lys Glu Asn Gln Arg Leu Ser Lys Lys Val Glu Ile Leu Glu Asn
            500                 505                 510

Glu Ile Val Gln Glu Lys Gln Ser Leu Gln Asn Cys Gln Asn Leu Ser
        515                 520                 525

Lys Asp Leu Met Lys Glu Lys Ala Gln Leu Glu Lys Thr Ile Glu Thr
    530                 535                 540

Leu Arg Glu Asn Ser Glu Arg Gln Ile Lys Ile Leu Glu Gln Glu Asn
545                 550                 555                 560

Glu His Leu Asn Gln Thr Val Ser Ser Leu Arg Gln Arg Ser Gln Ile
                565                 570                 575
```

-continued

Ser Ala Glu Ala Arg Val Lys Asp Ile Glu Lys Glu Asn Lys Ile Leu
            580                 585                 590

His Glu Ser Ile Lys Glu Thr Ser Ser Lys Leu Ser Lys Ile Glu Phe
        595                 600                 605

Glu Lys Arg Gln Ile Lys Lys Glu Leu Glu His Tyr Lys Glu Lys Gly
    610                 615                 620

Glu Arg Ala Glu Glu Leu Glu Asn Glu Leu His His Leu Lys Glu
625                 630                 635                 640

Asn Glu Leu Leu Gln Lys Lys Ile Thr Asn Leu Lys Ile Thr Cys Glu
                645                 650                 655

Lys Ile Glu Ala Leu Glu Gln Glu Asn Ser Glu Leu Glu Arg Glu Asn
            660                 665                 670

Arg Lys Leu Lys Lys Thr Leu Asp Ser Phe Lys Asn Leu Thr Phe Gln
        675                 680                 685

Leu Glu Ser Leu Glu Lys Glu Asn Ser Gln Leu Asp Glu Glu Asn Leu
    690                 695                 700

Glu Leu Arg Arg Asn Val Glu Ser Leu Lys Cys Ala Ser Met Lys Met
705                 710                 715                 720

Ala Gln Leu Gln Leu Glu Asn Lys Glu Leu Glu Ser Glu Lys Glu Gln
                725                 730                 735

Leu Lys Lys Gly Leu Glu Leu Leu Lys Ala Ser Phe Lys Lys Thr Glu
            740                 745                 750

Arg Leu Glu Val Ser Tyr Gln Gly Leu Asp Ile Glu Asn Gln Arg Leu
        755                 760                 765

Gln Lys Thr Leu Glu Asn Ser Asn Lys Lys Ile Gln Gln Leu Glu Ser
    770                 775                 780

Glu Leu Gln Asp Leu Glu Met Glu Asn Gln Thr Leu Gln Lys Asn Leu
785                 790                 795                 800

Glu Glu Leu Lys Ile Ser Ser Lys Arg Leu Glu Gln Leu Glu Lys Glu
                805                 810                 815

Asn Lys Ser Leu Glu Gln Glu Thr Ser Gln Leu Glu Lys Asp Lys Lys
            820                 825                 830

Gln Leu Glu Lys Glu Asn Lys Arg Leu Arg Gln Gln Ala Glu Ile Lys
        835                 840                 845

Asp Thr Thr Leu Glu Glu Asn Asn Val Lys Ile Gly Asn Leu Glu Lys
    850                 855                 860

Glu Asn Lys Thr Leu Ser Lys Glu Ile Gly Ile Tyr Lys Glu Ser Cys
865                 870                 875                 880

Val Arg Leu Lys Glu Leu Glu Lys Glu Asn Lys Glu Leu Val Lys Arg
                885                 890                 895

Ala Thr Ile Asp Ile Lys Thr Leu Val Thr Leu Arg Glu Asp Leu Val
            900                 905                 910

Ser Glu Lys Leu Lys Thr Gln Gln Met Asn Asn Asp Leu Glu Lys Leu
        915                 920                 925

Thr His Glu Leu Glu Lys Ile Gly Leu Asn Lys Glu Arg Leu Leu His
    930                 935                 940

Asp Glu Gln Ser Thr Asp Asp Arg Tyr Lys Leu Leu Glu Ser Lys Leu
945                 950                 955                 960

Glu Ser Thr Leu Lys Lys Ser Leu Glu Ile Lys Glu Glu Lys Ile Ala
                965                 970                 975

Ala Leu Glu Ala Arg Leu Glu Glu Ser Thr Asn Tyr Asn Gln Gln Leu
            980                 985                 990

Arg Gln Glu Leu Lys Thr Val Lys  Lys Asn Tyr Glu Ala  Leu Lys Gln

```
                995                 1000                1005
Arg Gln Asp Glu Glu Arg Met Val Gln Ser Ser Pro Pro Ile Ser
    1010                1015                1020

Gly Glu Asp Asn Lys Trp Glu Arg Glu Ser Gln Glu Thr Thr Arg
    1025                1030                1035

Glu Leu Leu Lys Val Lys Asp Arg Leu Ile Glu Val Glu Arg Asn
    1040                1045                1050

Asn Ala Thr Leu Gln Ala Glu Lys Gln Ala Leu Lys Thr Gln Leu
    1055                1060                1065

Lys Gln Leu Glu Thr Gln Asn Asn Asn Leu Gln Ala Gln Ile Leu
    1070                1075                1080

Ala Leu Gln Arg Gln Thr Val Ser Leu Gln Glu Gln Asn Thr Thr
    1085                1090                1095

Leu Gln Thr Gln Asn Ala Lys Leu Gln Val Glu Asn Ser Thr Leu
    1100                1105                1110

Asn Ser Gln Ser Thr Ser Leu Met Asn Gln Asn Ala Gln Leu Leu
    1115                1120                1125

Ile Gln Gln Ser Ser Leu Glu Asn Glu Asn Glu Ser Val Ile Lys
    1130                1135                1140

Glu Arg Glu Asp Leu Lys Ser Leu Tyr Asp Ser Leu Ile Lys Asp
    1145                1150                1155

His Glu Lys Leu Glu Leu Leu His Glu Arg Gln Ala Ser Glu Tyr
    1160                1165                1170

Glu Ser Leu Ile Ser Lys His Gly Thr Leu Lys Ser Ala His Lys
    1175                1180                1185

Asn Leu Glu Val Glu His Arg Asp Leu Glu Asp Arg Tyr Asn Gln
    1190                1195                1200

Leu Leu Lys Gln Lys Gly Gln Leu Glu Asp Leu Glu Lys Met Leu
    1205                1210                1215

Lys Val Glu Gln Glu Lys Met Leu Leu Glu Asn Lys Asn His Glu
    1220                1225                1230

Thr Val Ala Ala Glu Tyr Lys Lys Leu Cys Gly Glu Asn Asp Arg
    1235                1240                1245

Leu Asn His Thr Tyr Ser Gln Leu Leu Lys Glu Thr Glu Val Leu
    1250                1255                1260

Gln Thr Asp His Lys Asn Leu Lys Ser Leu Leu Asn Asn Ser Lys
    1265                1270                1275

Leu Glu Gln Thr Arg Leu Glu Ala Glu Phe Ser Lys Leu Lys Glu
    1280                1285                1290

Gln Tyr Gln Gln Leu Asp Ile Thr Ser Thr Lys Leu Asn Asn Gln
    1295                1300                1305

Cys Glu Leu Leu Ser Gln Leu Lys Gly Asn Leu Glu Glu Glu Asn
    1310                1315                1320

Arg His Leu Leu Asp Gln Ile Gln Thr Leu Met Leu Gln Asn Arg
    1325                1330                1335

Thr Leu Leu Glu Gln Asn Met Glu Ser Lys Asp Leu Phe His Val
    1340                1345                1350

Glu Gln Arg Gln Tyr Ile Asp Lys Leu Asn Glu Leu Arg Arg Gln
    1355                1360                1365

Lys Glu Lys Leu Glu Glu Lys Ile Met Asp Gln Tyr Lys Phe Tyr
    1370                1375                1380

Asp Pro Ser Pro Pro Arg Arg Arg Gly Asn Trp Ile Thr Leu Lys
    1385                1390                1395
```

```
Met Arg Lys Leu Ile Lys Ser Lys Lys Asp Ile Asn Arg Glu Arg
1400                1405                1410

Gln Lys Ser Leu Thr Leu Thr Pro Thr Arg Ser Asp Ser Ser Glu
1415                1420                1425

Gly Phe Leu Gln Leu Pro His Gln Asp Ser Gln Asp Ser Ser Ser
1430                1435                1440

Val Gly Ser Asn Ser Leu Glu Asp Gly Gln Thr Leu Gly Thr Lys
1445                1450                1455

Lys Ser Ser Met Val Ala Leu Lys Arg Leu Pro Phe Leu Arg Asn
1460                1465                1470

Arg Pro Lys Asp Lys Asp Lys Met Lys Ala Cys Tyr Arg Arg Ser
1475                1480                1485

Met Ser Met Asn Asp Leu Val Gln Ser Met Val Leu Ala Gly Gln
1490                1495                1500

Trp Thr Gly Ser Thr Glu Asn Leu Glu Val Pro Asp Asp Ile Ser
1505                1510                1515

Thr Gly Lys Arg Arg Lys Glu Leu Gly Ala Met Ala Phe Ser Thr
1520                1525                1530

Thr Ala Ile Asn Phe Ser Thr Val Asn Ser Ser Ala Gly Phe Arg
1535                1540                1545

Ser Lys Gln Leu Val Asn Asn Lys Asp Thr Thr Ser Phe Glu Asp
1550                1555                1560

Ile Ser Pro Gln Gly Val Ser Asp Asp Ser Ser Thr Gly Ser Arg
1565                1570                1575

Val His Ala Ser Arg Pro Ala Ser Leu Asp Ser Gly Arg Thr Ser
1580                1585                1590

Thr Ser Asn Ser Asn Asn Asn Ala Ser Leu His Glu Val Lys Ala
1595                1600                1605

Gly Ala Val Asn Asn Gln Ser Arg Pro Gln Ser His Ser Ser Gly
1610                1615                1620

Glu Phe Ser Leu Leu His Asp His Glu Ala Trp Ser Ser Ser Gly
1625                1630                1635

Ser Ser Pro Ile Gln Tyr Leu Lys Arg Gln Thr Arg Ser Ser Pro
1640                1645                1650

Val Leu Gln His Lys Ile Ser Glu Thr Leu Glu Ser Arg His His
1655                1660                1665

Lys Ile Lys Thr Gly Ser Pro Gly Ser Glu Val Val Thr Leu Gln
1670                1675                1680

Gln Phe Leu Glu Glu Ser Asn Lys Leu Thr Ser Val Gln Ile Lys
1685                1690                1695

Ser Ser Ser Gln Glu Asn Leu Leu Asp Glu Val Met Lys Ser Leu
1700                1705                1710

Ser Val Ser Ser Asp Phe Leu Gly Lys Asp Lys Pro Val Ser Cys
1715                1720                1725

Gly Leu Ala Arg Ser Val Ser Gly Lys Thr Pro Gly Asp Phe Tyr
1730                1735                1740

Asp Arg Arg Thr Thr Lys Pro Glu Phe Leu Arg Pro Gly Pro Arg
1745                1750                1755

Lys Thr Glu Asp Thr Tyr Phe Ile Ser Ser Ala Gly Lys Pro Thr
1760                1765                1770

Pro Gly Thr Gln Gly Lys Ile Lys Leu Val Lys Glu Ser Ser Leu
1775                1780                1785
```

Ser Arg Gln Ser Lys Asp Ser Asn Pro Tyr Ala Thr Leu Pro Arg
    1790                1795                1800

Ala Ser Ser Val Ile Ser Thr Ala Glu Gly Thr Thr Arg Arg Thr
    1805                1810                1815

Ser Ile His Asp Phe Leu Thr Lys Asp Ser Arg Leu Pro Ile Ser
    1820                1825                1830

Val Asp Ser Pro Pro Ala Ala Ala Asp Ser Asn Thr Thr Ala Ala
    1835                1840                1845

Ser Asn Val Asp Lys Val Gln Glu Ser Arg Asn Ser Lys Ser Arg
    1850                1855                1860

Ser Arg Glu Gln Gln Ser Ser
    1865                1870

<210> SEQ ID NO 2
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Lys Leu Gly Tyr Gly Arg Lys Lys Arg Gln Arg
            35                  40                  45

Arg Arg Gly Gly Ser Thr Met Ser Gly Tyr Pro Tyr Asp Val Pro Asp
    50                  55                  60

Tyr Ala Gly Ser Met Gly Gly Ser Gly His Ser Gly Glu Thr Leu Glu
65                  70                  75                  80

Ser Arg His His Lys Ile Lys Thr Gly Ser Pro Gly Ser Glu Val Val
                85                  90                  95

Thr Leu Gln Gln Phe Leu Glu Glu Ser Asn Lys Leu Thr Ser Val Gln
            100                 105                 110

Ile Lys Ser Ser Ser Gln Glu Asn Leu Leu Asp Glu Val Met Lys Ser
        115                 120                 125

Leu Ser Val Ser Ser Asp Phe Leu Gly Lys Asp Lys Pro Val Ser Cys
130                 135                 140

Gly Leu Ala Arg Ser Val Ser Gly Lys Thr Pro Gly Asp Phe Tyr Asp
145                 150                 155                 160

Arg Arg Thr Thr Lys Pro Glu Phe Leu Arg Pro Gly Pro Arg Lys Thr
                165                 170                 175

Glu Asp Thr Tyr Phe Ile Ser Ser Ala Gly Lys Pro Thr Pro Gly Thr
            180                 185                 190

Gln Gly Lys Ile Lys Leu Val Lys Glu Ser Ser Leu Ser Arg Gln Ser
        195                 200                 205

Lys Asp Ser Asn Pro Tyr Ala Thr Leu Pro Arg Ala Ser Ser Val Ile
210                 215                 220

Ser Thr Ala Glu Gly Thr Thr Arg Arg Thr Ser Ile His Asp Phe Leu
225                 230                 235                 240

Thr Lys Asp Ser Arg Leu Pro Ile Ser Val Asp Ser Pro Pro Ala Ala
                245                 250                 255

Ala Asp Ser Asn Thr Thr Ala Ala Ser Asn Val Asp Lys Val Gln Glu
            260                 265                 270

```
Ser Arg Asn Ser Lys Ser Arg Ser Arg Glu Gln Gln Ser Ser
            275                 280                 285

<210> SEQ ID NO 3
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Lys Leu Gly Tyr Gly Arg Lys Lys Arg Gln Arg
        35                  40                  45

Arg Arg Gly Gly Ser Thr Met Ser Gly Tyr Pro Tyr Asp Val Pro Asp
50                  55                  60

Tyr Ala Gly Ser Met Gly Gly Ser Gly His Ser Gly Glu Thr Leu Glu
65                  70                  75                  80

Ser Arg His His Lys Ile Lys Thr Gly Ser Pro Gly Ser Glu Val Val
                85                  90                  95

Thr Leu Gln Gln Ala Leu Glu Glu Ser Asn Lys Leu Thr Ser Val Gln
            100                 105                 110

Ile Lys Ser Ser Ser Gln Glu Asn Leu Leu Asp Glu Val Met Lys Ser
        115                 120                 125

Leu Ser Val Ser Ser Asp Phe Leu Gly Lys Asp Lys Pro Val Ser Cys
130                 135                 140

Gly Leu Ala Arg Ser Val Ser Gly Lys Thr Pro Gly Asp Phe Tyr Asp
145                 150                 155                 160

Arg Arg Thr Thr Lys Pro Glu Phe Leu Arg Pro Gly Pro Arg Lys Thr
                165                 170                 175

Glu Asp Thr Tyr Phe Ile Ser Ser Ala Gly Lys Pro Thr Pro Gly Thr
            180                 185                 190

Gln Gly Lys Ile Lys Leu Val Lys Glu Ser Ser Leu Ser Arg Gln Ser
        195                 200                 205

Lys Asp Ser Asn Pro Tyr Ala Thr Leu Pro Arg Ala Ser Ser Val Ile
    210                 215                 220

Ser Thr Ala Glu Gly Thr Thr Arg Arg Thr Ser Ile His Asp Phe Leu
225                 230                 235                 240

Thr Lys Asp Ser Arg Leu Pro Ile Ser Val Asp Ser Pro Ala Ala
                245                 250                 255

Ala Asp Ser Asn Thr Thr Ala Ala Ser Asn Val Asp Lys Val Gln Glu
            260                 265                 270

Ser Arg Asn Ser Lys Ser Arg Ser Arg Glu Gln Gln Ser Ser
        275                 280                 285

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      TAT-peptide transduction domain

<400> SEQUENCE: 4
```

```
Tyr Gly Arg Lys Lys Arg Arg Gln Arg Arg Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ala Arg Lys Ala Arg Arg Gln Ala Arg Arg
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Ala Arg Ala Ala Ala Arg Gln Ala Arg Ala
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Ala Arg Ala Ala Arg Arg Ala Ala Arg Arg
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Ala Arg Ala Ala Arg Arg Ala Ala Arg Ala
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Ala Arg Arg Arg Arg Arg Arg Arg Arg Arg
1               5                   10

<210> SEQ ID NO 10
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 10

Tyr Ala Ala Ala Arg Arg Arg Arg Arg Arg
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 11

Gly Gly Ser Gly His Ser Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 12

His His His His His His
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      HA tag

<400> SEQUENCE: 13

Tyr Pro Tyr Asp Val Pro Asp Tyr Ala
1               5

<210> SEQ ID NO 14
<211> LENGTH: 212
<212> TYPE: PRT
<213> ORGANISM: Homo sapiens
<220> FEATURE:
<223> OTHER INFORMATION: GIV-CT

<400> SEQUENCE: 14

Glu Thr Leu Glu Ser Arg His His Lys Ile Lys Thr Gly Ser Pro Gly
1               5                   10                  15

Ser Glu Val Val Thr Leu Gln Gln Phe Leu Glu Glu Ser Asn Lys Leu
            20                  25                  30

Thr Ser Val Gln Ile Lys Ser Ser Gln Glu Asn Leu Leu Asp Glu
        35                  40                  45

Val Met Glu Thr Lys Ser Leu Ser Val Ser Asp Phe Leu Gly Lys
    50                  55                  60

Asp Lys Pro Val Ser Cys Gly Leu Ala Arg Ser Val Ser Gly Lys Thr
65                  70                  75                  80

Pro Gly Asp Phe Tyr Asp Arg Arg Thr Thr Lys Pro Glu Phe Leu Arg
                85                  90                  95
```

```
Pro Gly Pro Arg Lys Thr Glu Asp Thr Tyr Phe Ile Ser Ser Ala Gly
            100                 105                 110

Lys Pro Thr Pro Gly Thr Gln Gly Lys Ile Lys Leu Val Lys Glu Ser
        115                 120                 125

Ser Leu Ser Arg Gln Ser Lys Asp Ser Asn Pro Tyr Ala Thr Leu Pro
        130                 135                 140

Arg Ala Ser Ser Val Ile Ser Thr Ala Glu Gly Thr Thr Arg Arg Thr
145                 150                 155                 160

Ser Ile His Asp Phe Leu Thr Lys Asp Ser Arg Leu Pro Ile Ser Val
                165                 170                 175

Asp Ser Pro Pro Ala Ala Ala Asp Ser Asn Thr Thr Ala Ala Ser Asn
            180                 185                 190

Val Asp Lys Val Gln Glu Ser Arg Asn Ser Lys Ser Arg Ser Arg Glu
        195                 200                 205

Gln Gln Ser Ser
    210

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ggaatgtact atatagcaa                                              19
```